(12) United States Patent
Crine et al.

(10) Patent No.: US 10,000,532 B2
(45) Date of Patent: *Jun. 19, 2018

(54) BONE DELIVERY CONJUGATES AND METHOD OF USING SAME TO TARGET PROTEINS TO BONE

(75) Inventors: Philippe Crine, Outremont (CA); Guy Boileau, Brossard (CA); Isabelle Lemire, Montréal (CA); Thomas P. Loisel, Montréal (CA)

(73) Assignee: Alexion Pharmaceuticals, Inc., New Haven, CT (US)

( * ) Notice: Subject to any disclaimer, the term of this patent is extended or adjusted under 35 U.S.C. 154(b) by 1537 days.

This patent is subject to a terminal disclaimer.

(21) Appl. No.: 12/638,527

(22) Filed: Dec. 15, 2009

(65) Prior Publication Data

US 2010/0221234 A1 Sep. 2, 2010

Related U.S. Application Data

(63) Continuation of application No. 11/111,664, filed on Apr. 21, 2005, now Pat. No. 7,763,712.

(60) Provisional application No. 60/563,828, filed on Apr. 21, 2004, provisional application No. 60/590,347, filed on Jul. 23, 2004, provisional application No. 60/614,984, filed on Oct. 4, 2004.

(51) Int. Cl.
| | |
|---|---|
| *C07K 7/06* | (2006.01) |
| *C07K 14/51* | (2006.01) |
| *C12N 9/16* | (2006.01) |
| *C12N 9/64* | (2006.01) |
| *A61K 47/64* | (2017.01) |
| *A61K 38/00* | (2006.01) |

(52) U.S. Cl.
CPC ............ *C07K 7/06* (2013.01); *A61K 47/645* (2017.08); *C07K 14/51* (2013.01); *C12N 9/16* (2013.01); *C12N 9/6421* (2013.01); *C12N 9/6494* (2013.01); *C12Y 304/24011* (2013.01); *A61K 38/00* (2013.01); *C07K 2319/01* (2013.01); *C07K 2319/23* (2013.01); *C12Y 301/03001* (2013.01)

(58) Field of Classification Search
None
See application file for complete search history.

(56) References Cited

U.S. PATENT DOCUMENTS

| | | | |
|---|---|---|---|
| 6,290,952 B1 | 9/2001 | Poelstra et al. | |
| 6,420,384 B2 | 7/2002 | Weigele et al. | |
| 6,436,386 B1 | 8/2002 | Roberts et al. | |
| 6,455,495 B1 | 9/2002 | Orgel et al. | |
| 6,458,579 B2 | 10/2002 | Hopwood et al. | |
| 6,905,689 B2 | 6/2005 | Schneidinger et al. | |
| 7,179,903 B2 | 2/2007 | McArthur et al. | |
| 7,399,466 B2 | 7/2008 | Boileau | |
| 7,625,564 B2 | 12/2009 | Wang et al. | |
| 7,763,712 B2 | 7/2010 | Crine et al. | |
| 7,803,769 B2 | 9/2010 | Sullivan et al. | |
| 7,943,126 B2 | 5/2011 | Tomatsu et al. | |
| 7,960,529 B2 | 6/2011 | Crine et al. | |
| 2002/0183276 A1 | 12/2002 | Millan et al. | |
| 2003/0158132 A1 | 8/2003 | Kovesdi | |
| 2004/0023916 A1 | 2/2004 | Millan et al. | |
| 2004/0234518 A1 | 11/2004 | Crine et al. | |
| 2005/0276796 A1 | 12/2005 | Tomatsu et al. | |
| 2006/0014687 A1 | 1/2006 | Crine et al. | |
| 2007/0041972 A1 | 2/2007 | Rother et al. | |
| 2007/0042957 A1 | 2/2007 | Burnett et al. | |
| 2007/0081984 A1 | 4/2007 | Tomatsu et al. | |
| 2007/0081986 A1 | 4/2007 | Tomatsu et al. | |
| 2008/0085862 A1 | 4/2008 | Kim et al. | |
| 2008/0181903 A1 | 7/2008 | Bhaskar et al. | |
| 2009/0069243 A1 | 3/2009 | Burnett, Jr. et al. | |
| 2009/0142347 A1 | 6/2009 | Millan et al. | |
| 2009/0238814 A1 | 9/2009 | Tomatsu et al. | |
| 2010/0008979 A1 | 1/2010 | Tomatsu et al. | |
| 2010/0184680 A1 | 7/2010 | Bevec | |
| 2010/0221234 A1 | 9/2010 | Crine et al. | |
| 2010/0240125 A1 | 9/2010 | Crine et al. | |

(Continued)

FOREIGN PATENT DOCUMENTS

| | | |
|---|---|---|
| JP | 8070875 | 3/1996 |
| JP | 2000-327583 | 11/2000 |
| JP | 2002-541776 | 12/2002 |

(Continued)

OTHER PUBLICATIONS

Whyte et al., "Infantile hypophosphatasia: Normalization of circulating bone alkaline phosphatase activity followed by skeletal remineralization", Journal of Pediatrics, vol. 108, No. 1, pp. 82-88 (Jan. 1986).*

Single page of Apr. 23, 2013 IDS document AR—Milan; pdf page 138; Knockout Mouse Models.*

Tomatsu, Declaration Under 37 C.F.R. § 1.132 dated Nov. 27, 2007, filed in U.S. Appl. No. 11/484,870, filed Dec. 3, 2007.

Tomatsu, Declaration Under 37 C.F.R. § 1.132 dated Jun. 1, 2009, filed in U.S. Appl. No. 11/484,870, filed Jun. 2, 2009.

Reply to Final Office Action for U.S. Appl. No. 13/071,445, filed Oct. 25, 2012.

Addison et al., "Pyrophosphate Inhibits Mineralization of Osteoblast Cultures by Binding to Mineral, Up-regulating Osteopontin, and Inhibiting Alkaline Phosphate Activity," *J. Biol. Chem.* 282:15872-15883, 2007.

(Continued)

Primary Examiner — Anand U Desai
(74) Attorney, Agent, or Firm — Clark & Elbing LLP

(57) ABSTRACT

A bone delivery conjugate having a structure selected from the group consisting of: A) X-$D_n$-Y-protein-Z; and B) Z-protein-Y-$D_n$-X, wherein X is absent or is an amino acid sequence of at least one amino acid; Y is absent or is an amino acid sequence of at least one amino acid; Z is absent or is an amino acid sequence of at least one amino acid; and $D_n$ is a poly aspartate wherein n=10 to 16. Compositions comprising same and methods of use thereof.

49 Claims, 18 Drawing Sheets

(56) References Cited

U.S. PATENT DOCUMENTS

2010/0297119 A1  11/2010  Crine et al.
2011/0250187 A1  10/2011  Tomatsu et al.

FOREIGN PATENT DOCUMENTS

| WO | WO 92/020371 | 11/1992 |
|---|---|---|
| WO | WO 98/35703 | 8/1998 |
| WO | WO 00/18954 | 4/2000 |
| WO | WO 00/050580 | 8/2000 |
| WO | WO 00/64486 | 11/2000 |
| WO | WO-01/36620 A2 | 5/2001 |
| WO | WO 02/015918 | 2/2002 |
| WO | WO 02/068579 | 9/2002 |
| WO | WO-2005/007809 A2 | 1/2005 |
| WO | WO 05/103263 | 11/2005 |
| WO | WO 06/039480 | 4/2006 |
| WO | WO-06/060641 A2 | 6/2006 |
| WO | WO 08/138131 | 11/2008 |
| WO | WO 11/134084 | 11/2011 |

OTHER PUBLICATIONS

Anderson et al., "Impaired Calcification Around Matrix Vesicles of Growth Plate and Bone in Alkaline Phosphatase-deficient Mice," *Am. J. Pathol.* 164:841-847, 2004.

Bernardi et al., "Chromatography of Proteins on Hydoxyapatite," *Methods in Enzymology* 27:471-479, 1973.

Bobé et al., "Fas-Mediated Liver Damage in MRL Hemopoietic Chimeras Undergoing Ipr-Mediated Graft-Versus-Host Disease," *J. Immunol.* 159:4197-4204, 1997.

Campbell et al., "Insulin-Like Growth Factor (IGF)-Binding Protein-5-(201-218) Region Regulates Hydroxyapatite and IGF-I Binding," *Am. J. Physiol.* 273:E1005-1013, 1997.

Ciancaglini et al., "Contribution of Matrix Vesicles and Alkaline Phosphatase to Ectopic Bone Formation," *Braz. J. Med. Biol. Res.* 39:603-610, 2006.

Data Sheet for pFUSE-SEAP-hFC, Invivogen, San Diego, CA, 1989.

Di Mauro et al., "Kinetic Characterization of Hypophosphatasia Mutations with Physiological Substrates," *J. Bone Miner. Res.* 17:1383-1391, 2002.

Dumont et al., "Monomeric Fc Fusions: Impact on Pharmacokinetic and Biological Activity of Protein Therapeutics," *BioDrugs* 20:151-160, 2006.

Fujisaki et al., "Osteotropic Drug Delivery System (ODDS) Based on Bisphosphonic Prodrug. I.v. Effects of Osteotropic Estradiol on Bone Mineral Density and Uterine Weight in Ovariectomized Rats," *J. Drug Target.* 5:129-138, 1997.

Fujisawa et al., "Acidic Amino Acid-Rich Sequences as Binding Sites of Osteonectin to Hydroxyapatite Crystals," *Biochim. Biophys. Acta* 1292:53-60, 1996.

Gilbert et al., "Chimeric Peptides of Statherin and Osteopontin that Bind Hydroxyapatite and Mediate Cell Adhesion," *J. Biol. Chem.* 275:16213-16218, 2000.

Halling Linder et al., "Glycosylation Differences Contribute to Distinct Catalytic Properties Among Bone Alkaline Phosphotase Isoforms," *Bone* 45:987-993, 2009.

Henthorn and Whyte, "Missense Mutations of the Tissue Non-Specific Alkaline Phosphatase Gene in Hypophosphatasia," *Clin. Chem.* 38:2501-2505, 1992.

Hosain et al., "Targeted Delivery of Antineoplastic Agent to Bone: Biodistribution Studies of Technetium-99m-Labeled Gem-Bisphosphonate Conjugate of Methotrexate," *J. Nucl. Med.* 37:105-107, 1996.

Hunter et al., "Modulation of Crystal Formation by Bone Phosphoproteins: Structural Specificity of the Osteopontin-Mediated Inhibition of Hydroxyapatite Formation," *Biochem. J.* 300:723-728, 1994.

Ikezawa, "Glycosylphosphatidylinositol (GPI)-anchored Proteins," *Biol. Pharm. Bull.* 25:409-417, 2002.

Kasugai et al., "Selective Drug Delivery System to Bone: Small Peptide (Asp)6 Conjugation," *J. Bone Miner. Res.* 15:936-943, 2000.

Kaufmann et al., "Influence of Low Temperature on Productivity, Proteome and Protein Phosphorylation of CHO Cells," *Biotechnol. Bioeng.* 63:573-582, 1999.

Millán, "Mammalian Alkaline Phosphatases," in *Biology to Applications in Medicine and Biotechnology*, pp. 107-185, 2006 (Wiley-VCH Verlag).

Millán et al., "Enzyme Replacement Therapy for Murine Hypophosphatasia." *J. Bone Miner. Res.* 23: 777-787, 2008 (Epublished ahead of print on Dec. 17, 2007).

Murshed et al., "Unique Coexpression in Osteoblasts of Broadly Expressed Genes Accounts for the Spatial Restriction of ECM Mineralization to Bone," *Genes Dev.* 19:1093-1104, 2005.

Nishioka et al., "Enhancement of Drug Delivery to Bone: Characterization of Human Tissue-Nonspecific Alkaline Phosphatase Tagged with an Acidic Oligopeptide," *Mol. Genet. Metab.* 88:244-255, 2006.

Oda et al., "A General Method for Rapid Purification of Soluble Versions of Glycosylphosphatidylinositol-Anchored Proteins Expressed in Insect Cells: An Application for Human Tissue-Nonspecific Alkaline Phosphatase," *J. Biochem.* 126:694-699, 1999.

Patti et al., "Critical Residues in the Ligand-Binding Site of the *Staphylococcus aureus* Collagen-Binding Adhesin (MSCRAMM)," *J. Biol. Chem.* 270:12005-12011, 1995.

Rezende et al., "Inorganic Pyrophosphate-phosphohydrolitic Activity Associated with Rat Osseous Plate Alkaline Phosphatase," *Cell. Mol. Biol.* (*Noisy-le-grand*) 44:293-302, 1998.

Rowe et al., "MEPE, A New Gene Expressed in Bone Marrow and Tumors Causing Osteomalacia," *Genomics* 67:54-68, 2000.

Salih et al., "Identification of the Phosphorylated Sites of Metabolically 32P-Labeled Osteopontin from Cultured Chicken Osteoblasts," *J. Biol. Chem.* 272:13966-13973, 1997.

Sekido et al., "Novel Drug Delivery System to Bone Using Acidic Oligopeptide: Pharmacokinetic Characteristics and Pharmacological Potential," *J. Drug Target.* 9:111-121, 2001.

Sharom and Lehto, "Glycosylphosphatidylinositol-Anchored Proteins: Structure, Function, and Cleavage by Phosphatidylinositol-Specific Phospholipase C," *Biochem. Cell. Biol.* 8:535-549, 2002.

Shull et al., "Enzyme Replacement in a Canine Model of Hurler Syndrome," *Proc. Natl. Acad. Sci. USA* 91:12937-12941, 1994.

Spears et al., "Deoxyuridylate Effects on Thymidylate Synthase-5-Fluorodeoxyuridylate-Folate Ternary Complex Formation," *Biochem. Pharmacol.* 38:2985-2993, 1989.

Sturtz et al., "A Study of the Delivery-Targeting Concept Applied to Antineoplasic Drugs Active on Human Osteosarcoma. I. Synthesis and Biological Activity in Nude Mice Carrying Human Osteosarcoma Xenografts of Gem-Bisphosphonic Methotrexate Analogues," *Eur. J. Med. Chemistry* 27:825-833, 1992.

Symersky et al., "Structure of the Collagen-Binding Domain From a *Staphylococcus aureus* Adhesin," *Nat. Struct. Biol.* 4:833-838, 1997.

Uludag et al., "Bone Affinity of a Bisphosphonate-Conjugated Protein in Vivo," *Biotechnol. Prog.* 16:1115-1118, 2000.

Weinberg, "An Overview of Infliximab, Etanercept, Efalizumab, and Alefacept as Biologic Therapy for Psoriasis," *Clin. Ther.* 25:2487-2505, 2003.

Weiss et al., "Isolation and Characterization of a cDNA Encoding a Human Liver/Bone/Kidney-type Alkaline Phosphatase," *Proc. Natl. Acad. Sci. USA* 83:7182-7186, 1986.

Weninger et al., "Biochemical and Morphological Effects of Human Hepatic Alkaline-Phosphatase in a Neonate with Hypophosphatasia," *Acta Paediatr. Scand.* 154-160, 1989.

Whyte et al., "Infantile Hypophosphatasia: Enzyme Replacement Therapy by Intravenous Infusion of Alkaline Phosphatase-Rich Plasma From Patients with Paget Bone Disease," *J. Pediatr.* 101:379-386, 1982.

Whyte et al., "Enzyme Replacement Therapy for Infantile Hypophosphatasia Attempted by Intravenous Infusions of Alkaline Phosphatase," *J. Pediatr.* 105:926-933, 1984.

(56) References Cited

OTHER PUBLICATIONS

Whyte et al., "Infantile hypophosphatasia: normalization of circulating bone alkaline phosphatase activity followed by skeletal remineralization. Evidence for an intact structural gene for tissue nonspecific alkaline phosphatase," *J. Pediatr.* 108:82-88, 1986.
Whyte, "Hypophosphatasia and the Role of Alkaline Phosphatase in Skeletal Mineralization," *Endocr. Rev.* 15:439-461, 1994.
Whyte, "Alkaline Phosphatase: Placental and Tissue Non-specific Isoenzymes Hydrolyze Phosphoethanolamine, Inorganic Pyrophosphate, and Pyridoxal 5'-phosphate," *J. Clin. Invest.* 95:1440-1445, 1995.
Whyte et al., "Hypophosphatasia," in *The Metabolic and Molecular Bases for Disease*, p. 5313 only, 2001 (McGraw-Hill Book Company).
Whyte et al., "Heritable Forms of Rickets and Osteomalacia," in *Connective Tissues and Its Heritable Disorders*, pp. 765-787, 2002 (eds. R.M. Royce and B. Steinmann, Wiley-Liss, Inc. Hoboken).
Whyte et al., "Marrow Cell Transplantation for Infantile Hypophosphatasia," *J. Bone Miner. Res.* 18:624-636, 2003.
Yamamoto et al., "Prolonged Survival and Phenotypic Correction of Akp2(-/-) Hypophosphatasia Mice by Lentiviral Gene Therapy," *J Bone Miner Res.* 26:135-142, 2011.
Yokogawa et al., "Selective Delivery of Estradiol to Bone by Aspartic Acid Oligopeptide and Its Effects on Ovariectomized Mice," *Endocrinology* 142:1228-1233, 2001.
Young et al., "Structure, Expression, and Regulation of the Major Noncollagenous Matrix Proteins of Bone," *Clin. Orthop. Relat. Res.* 281:275-294, 1992.
Office Action for U.S. Appl. No. 11/111,664 (dated Oct. 4, 2007).
Office Action for U.S. Appl. No. 11/111,664 (dated May 14, 2008).
Office Action for U.S. Appl. No. 11/111,664 (dated Dec. 4, 2008).
Reply to Office Action for U.S. Appl. No. 11/111,664 (filed Sep. 10, 2008).
Office Action for U.S. Appl. No. 11/484,870 (dated Jan. 25, 2007).
Office Action for U.S. Appl. No. 11/484,870 (dated Jul. 5, 2007).
Office Action for U.S. Appl. No. 11/484,870 (dated Oct. 1, 2007).
Office Action for U.S. Appl. No. 11/484,870 (dated Jun. 25, 2008).
Office Action for U.S. Appl. No. 11/484,870 (dated Feb. 2, 2009).
Office Action for U.S. Appl. No. 11/484,870 (dated Aug. 11, 2009).
Office Action for U.S. Appl. No. 12/405,920 (dated Dec. 17, 2009).
Office Action for U.S. Appl. No. 12/405,920 (dated Aug. 9, 2010).
Office Action for U.S. Appl. No. 12/793,517 (dated Aug. 16, 2010).
Communication from Examining Division for European Application No. EP 05 73 9065 (dated Jun. 18, 2009).
Communication from Examining Division for European Application No. EP 05 73 9065 (dated Jun. 11, 2010).
International Search Report and Written Opinion for International Application No. PCT/CA2005/000615 (dated Aug. 18, 2005).
International Search Report and Written Opinion for International Application No. PCT/CA2008/000923 (dated Sep. 12, 2008).
Supplementary European Search Report for European Application No. EP 05 73 9065 (date of completion of search Nov. 7, 2008, dated Dec. 2, 2008).
Supplementary European Search Report for European Application No. EP 08 75 7088 (date of completion of search Jun. 7, 2010, dated Jun. 21, 2010).
Achord et al., "Human Beta-Glucuronidase: In Vivo Clearance and in Vitro Uptake by a Glycoprotein Recognition System on Reticuloendothelial Cells," *Cell* 15:269-278 (1978).
Altarescu et al., "The Efficacy of Enzyme Replacement Therapy in Patients with Chronic Neuronopathic Gaucher's Disease," *J. Pediatr.* 168:539-547 (2001).
Anderson et al., "Matrix Vesicles in Osteomalacic Hypophosphatasia Bone Contain Apatite-Like Mineral Crystals," *Am. J. Pathol.* 151:1555-1561 (1997).
Barranger and O'Rourke, "Lessons Learned from the Development of Enzyme Therapy for Gaucher Disease," *J. Inherit. Metab. Dis.* 24:89-96 (2001).

Barton et al., "Replacement Therapy for Inherited Enzyme Deficiency—Macrophage-Targeted Glucocerebrosidase for Gaucher's Disease," *N. Engl. J. Med.* 324:1464-1470 (1991) (abstract only).
Boskey et al. "Matrix Vesicles Promote Mineralization in a Gelatin Gel," *Calcif. Tissue Int* 60:309-315 (1997).
Boskey, "Amorphous Calcium Phosphate: The Contention of Bone," *J. Dent Res.* 76:1433-1436 (1997).
Cleland et al., "Emerging Protein Delivery Methods," *Curr. Opin. Biotechnol.* 12:212-219 (2001).
Crawley et al., "Enzyme Replacement Therapy in a Feline Model of Maroteaux-Lamy Syndrome," *J. Clin. Invest.* 97:1864-1873 (1996).
Eng et al., "Safety and Efficacy of Recombinant Human Alpha-Galactosidase A Replacement Therapy in Fabry's Disease," *N. Engl. J. Med.* 345:9-16 (2001).
Furbish et al., "Uptake and Distribution of Placental Glucocerebrosidase in Rat Hepatic Cells and Effects of Sequential Deglycosylation," *Biochim. Biophys. Acta.* 673:425-434 (1981).
Guo et al., "Protein Tolerance to Random Amino Acid Change," *Proc. Natl. Acad. Sci.* 101:9205-9210 (2004).
Hardy et al., "Dissection of a Carboxy-Terminal Region of the Yeast Regulatory Protein RAP1 with Effects on Both Transcriptional Activation and Silencing," *Mol. Cell. Biol.* 12:1209-1217 (1992).
Hult and Berglund, "Engineered Enzymes for Improved Organic Synthesis," *Curr. Opin. Biotechnol.* 14:395-400 (2003).
Kakkis et al., "Enzyme-Replacement Therapy in Mucopolysaccharidosis I," *N. Engl. J. Med.* 344:182-188 (2001).
Leone et al., "Allosteric Modulation of Pyrophosphatase Activity of Rat Osseous Plate Alkaline Phosphatase by Magnesium Ions," *Int. J. Biochem. Cell Biol.* 30:89-97 (1998).
Meyer, "Can Biological Calcification Occur in the Presence of Pyrophosphate?" *Arch. Biochem. Biophys.* 231:1-8 (1984).
Michigami et al., "Common Mutations F310L and T1559del in the Tissue-Nonspecific Alkaline Phosphatase Gene are Related to Distinct Phenotypes in Japanese Patients with Hypophosphatasia," *Eur. J. Pediatr.* 164:277-282 (2005).
Moss et al., "Association of Inorganic-Pyrophosphatase Activity with Human Alkaline-Phosphatase Preparations," *Biochem. J.* 102:53-57 (1967).
Murray, "Lectin-Specific Targeting of Lysosomal Enzymes to Reticuloendothelial Cells," *Methods Enzymol.* 149:25-42 (1987).
Narisawa et al., "Inactivation of Two Mouse Alkaline Phosphatase Genes and Establishment of a Model of Infantile Hypophosphatasia," *Dev. Dyn.* 208:432-446 (1997).
Narisawa et al., "Abnormal Vitamin B6 Metabolism in Alkaline Phosphatase Knock-Out Mice Causes Multiple Abnormalities, but Not the Impaired Bone Mineralization," *J. Pathol.* 193:125-133 (2001).
Ngo et al., "Computational Complexity, Protein Structure Prediction, and the Levinthal Paradox," *The Protein Folding Problem and Tertiary Structure Prediction*, Merz et al. (ed.), 433 and 492-495 (1994).
Pedersen et al., "Removal of N-Terminal Polyhistidine Tags from Recombinant Proteins Using Engineered Aminopeptidases," *Prot. Expr. Purifi.* 15:389-400 (1999).
Russell et al., "Inorganic Pyrophosphate in Plasma in Normal Persons and in Patients with Hypophosphatasia, Osteogenesis Imperfecta, and Other Disorders of Bone," *J. Clin. Invest.* 50:961-969 (1971).
Sands et al., "Enzyme Replacement Therapy for Murine Mucopolysaccharidosis Type VII," *J. Clin. Invest.* 93:2324-2331 (1994).
Stahl et al., "Evidence for Receptor-Mediated Binding of Glycoproteins, Glycoconjugates, and Lysosomal Glycosidases by Alveolar Macrophages," *Proc. Natl. Acad. Sci.* 75:1399-1403 (1978).
Waymire et al., "Mice Lacking Tissue Non-Specific Alkaline Phosphatase Die from Seizures Due to Defective Metabolism of Vitamin B-6," *Nat. Genet.* 11:45-51 (1995).
Weiss et al., "Structure of the Human Liver/Bone/Kidney Alkaline Phosphatase Gene," *J. Biol. Chem.* 263:12002-12010 (1988).
Whyte et al., "Hypophosphatasia," in *The Metabolic and Molecular Bases of Inherited Disease* ($8^{th}$ ed), pp. 5313-5329, 2001 (McGraw-Hill Book Company) (epub pp. 1-41).

(56) References Cited

OTHER PUBLICATIONS

Advisory Action for U.S. Appl. No. 11/484,870 (dated Dec. 20, 2007).
Restriction Requirement for U.S. Appl. No. 12/599,679 (dated Jun. 12, 2012).
Office Action for U.S. Appl. No. 13/071,445 (dated Feb. 6, 2012).
Office Action for U.S. Appl. No. 13/071,445 (dated May 25, 2012).
Communication from Examining Division for European Application No. EP 08 75 7088 (dated Apr. 20, 2011).
Extended European Search Report for European Application No. EP 11 00 0196 (dated Jun. 22, 2011).
Extended European Search Report for European Application No. EP 11 00 4496 (dated Aug. 26, 2011).
International Search Report and Written Opinion for International Application No. PCT/CA2011/050258 (dated Jul. 29, 2011).
Ali et al., "Isolation and characterization of calcifying matrix vesicles from epiphyseal cartilage," *Proc. Natl. Acad. Sci.* 67(3): 1513-1520 (1970).
Anderson and Reynolds, "Pyrophosphate stimulation of calcium uptake into cultured embryonic bones. Fine structure of matrix vesicles and their role in calcification," *Dev. Biol.* 34: 211-227 (1973).
Anderson et al., "Sustained osteomalacia of long bones despite major improvement in other hypophosphatasia-related mineral deficits in tissue nonspecific alkaline phosphatase/nucleotide pyrophosphatase phosphodiesterase 1 double-deficient mice," *Am. J. Pathol.* 166(6): 1711-1720 (2005).
Anderson et al., "The role of matrix vesicles in growth plate development and biomineralization," *Front. Biosci.* 10: 822-837 (2005).
Beertsen et al., "Root development in mice lacking functional tissue non-specific alkaline phosphatase gene: Inhibition of acellular cementum formation," *J. Dent. Res.* 78: 1221-1229 (1999).
Bennett et al., "Extracellular domain-IgG fusion proteins for three human natriuretic peptide receptors," *J. Biol. Chem.* 266(34): 23060-23067 (1991).
Bernard, "Ultrastructural localization of alkaline phosphatase in initial intramembranous osteogenesis," *Clin. Orthop. Relat. Res.* 135: 218-225 (1978).
Bonilla, "Pharmacokinetics of immunoglobulin administered via intravenous or subcutaneous routes," *Immunol. Allergy Clin. N. Am.* 28: 803-819 (2008).
Byers et al., "Effect of enzyme replacement therapy on bone formation in a feline model of mucopolysaccharidosis type VI," *Bone* 21: 425-431 (1997).
Cameron and Ellmers, "Minireview: natriuretic peptides during development of the fetal heart and circulation," *Endocrinology* 144: 2191-2194 (2003).
Clemens et al., "Pharmacokinetics and biological actions of subcutaneously administered human brain natriuretic peptide," *J. Pharmacol. Exp. Ther.* 287: 67-71 (1998).
Declaration of Dr. Philippe Crine for EP08757088.3, executed Jan. 14, 2011 (6 pages).
Engel and Lowe, "Characterization of the hormone binding site of natriuretic peptide receptor-C," *FEBS Letters* 360: 169-172 (1995).
European Search Report for European Application No. EP08757088, dated Jun. 7, 2010 (6 pages).
Farley and Magnusson, "Effects of tunicamycin, mannosamine, and other inhibitors of glycoprotein processing on skeletal alkaline phosphatase in human osteoblast-like cells," *Calcif. Tissue. Int.* 76: 63-74 (2005).
Fedde et al., "Alkaline phosphatase knock-out mice recapitulate the metabolic and skeletal defects of infantile hypophosphatasia," *J. Bone Miner. Res.* 14(12): 2015-2026 (1999).
Garg, *Investigation of the role of FcRn in the absorption, distribution, and elimination of monoclonal antibodies*. Dissertation: State University of New York at Buffalo, 2007 (abstract only).
Greenberg et al., "A homoallelic Gly$^{317}$ → Asp mutation in ALPL causes the perinatal (lethal) form of hypophosphatasia in Canadian mennonites," *Genomics* 17: 215-217 (1993).

Harmey et al., "Concerted regulation of inorganic pyrophosphate and osteopontin by Akp2, Enpp1, and Ank," *Am. J. Pathol.* 164(4): 1199-1209 (2004).
Harmey et al., "Elevated skeletal osteopontin levels contribute to the hypophosphatasia phenotype in Akp2$^{-/-}$ mice," *J. Bone Miner. Res.* 21(9): 1377-1386 (2006).
Hawrylak and Stinson, "The solubilization of tetrameric alkaline phosphatase from human liver and its conversion into various forms by phosphatlidylinositol phospholipase C or proteolysis," *J. Biol. Chem.* 263(28): 14368-14373 (1988).
Henthorn et al., "Different missense mutations at the tissue-nonspecific alkaline phosphatase gene locus in autosomal recessively inherited forms of mild and severe hypophosphatasia," *Proc. Natl. Acad. Sci. USA* 89: 9924-9928 (1992).
Hessle et al., "Tissue-nonspecific alkaline phosphatase and plasma cell membrane glucoprotein-1 are central antagonistic regulators of bone mineralization," *Proc. Natl. Acad. Sci.* 99(14): 9445-9449 (2002).
Jansonius, "Structure, evolution and action of vitamin B$_6$-dependent enzymes," *Curr. Opin. Struct. Biol.* 8: 759-769 (1998).
Jin et al., "Novel analog of atrial natriuretic peptide selective for receptor-A produces increased diuresis and natriuresis in rats," *J. Clin. Invest.* 98(4): 969-976 (1996).
Johnson et al., "Matrix vesicle plasma cell membrane glycoprotein-1 regulates mineralization by murine osteoblastic MC3T3 cells," *J. Bone Miner. Res.* 14(6): 883-892 (1999).
Kochendoerfer, "Protein & peptide drug delivery—third international conference: Minimally invasive delivery methods," *IDrugs* 6(11): 1043-1045 (2003).
Kostenuik et al., "Infrequent delivery of a long-acting PTH-Fc fusion protein has potent anabolic effects on cortical and cancellous bone," *J. Bone Miner. Res.* 22(10): 1534-1547 (2007).
Mahmood et al., "Selection of the first-time dose in humans: Comparison of different approaches based on interspecies scaling of clearance," *J. Clin. Pharmacol.* 43: 692-697 (2003).
Millan, "Mammalian Alkaline Phosphatases," Wiley-WCH Verlag GmbH & Co., Weinheim, Germany, 2006 (322 pages).
Morris et al., "Immunolocalization of alkaline phosphatase in osteoblasts and matrix vesicles of human fetal bone," *Bone Miner.* 19: 287-298 (1992).
Nasu et al., "Abberant interchain disulfide bridge of tissue-nonspecific alkaline phosphatase with an Arg433 → Cys substitution associated with severe hypophosphatasia," *FEBS Journal* 273: 5612-5624 (2006).
NCBI Protein Database Accession No. AAF64516, downloaded on Apr. 16, 2013.
NCBI Protein Database Accession No. AAC33858, downloaded on Apr. 16, 2013.
NCBI Protein Database Accession No. AAH21289, downloaded on Apr. 16, 2013.
NCBI Protein Database Accession No. AAH66116, downloaded on Apr. 16, 2013.
NCBI Protein Database Accession No. AAH90861, downloaded on Apr. 16, 2013.
NCBI Protein Database Accession No. AAI10910, downloaded on Apr. 16, 2013.
NCBI Protein Database Accession No. AAI26166, downloaded on Apr. 16, 2013.
NCBI Protein Database Accession No. AAI18209, downloaded on Apr. 16, 2013.
NCBI Protein Database Accession No. AAN64273, downloaded on Apr. 16, 2013.
NCBI Protein Database Accession No. NP_000469, downloaded on Apr. 16, 2013.
NCBI Protein Database Accession No. NP_001623, downloaded on Apr. 16, 2013.
NCBI Protein Database Accession No. NP_001036028, downloaded on Apr. 16, 2013.
NCBI Protein Database Accession No. NP_001253798, downloaded on Apr. 17, 2013.
NCBI Protein Database Accession No. NP_001622, downloaded on Apr. 16, 2013.

(56) References Cited

OTHER PUBLICATIONS

NCBI Protein Database Accession No. NP_031457, downloaded on Apr. 16, 2013.
NCBI Protein Database Accession No. NP_037191, downloaded on Apr. 16, 2013.
NCBI Protein Database Accession No. NP_112603, downloaded on Apr. 16, 2013.
NCBI Protein Database Accession No. NP_776412, downloaded on Apr. 17, 2013.
NCBI Protein Database Accession No. NP_789828, downloaded on Apr. 16, 2013.
NCBI Protein Database Accession No. P01857, downloaded on Apr. 18, 2013.
NCBI Protein Database Accession No. P05186, downloaded on Apr. 16, 2013.
NCBI Protein Database Accession No. P05187, downloaded on Apr. 16, 2013.
NCBI Protein Database Accession No. P08289, downloaded on Apr. 16, 2013.
NCBI Protein Database Accession No. P09487, downloaded on Apr. 16, 2013.
NCBI Protein Database Accession No. P09242, downloaded on Apr. 16, 2013.
NCBI Protein Database Accession No. P09923, downloaded on Apr. 16, 2013.
NCBI Protein Database Accession No. P10696, downloaded on Apr. 16, 2013.
NCBI Protein Database Accession No. Q29486, downloaded on Apr. 16, 2013.
NCBI Protein Database Accession No. Q9N0V0, downloaded on Apr. 16, 2013.
NCBI Protein Database Accession No. XP-001109717, downloaded on Apr. 17, 2013.
Nosjean et al., "Human tissue non-specific alkaline phosphatases: Sugar-moiety-induced enzymic and antigenic modulations and genetic aspects," *Biochem. J.* 321: 297-303 (1997).
Ramachandran et al., "Treatment of an anabolic bone deficiency in neurofibromatosis with bone morphogenetic proteins and its potential application for congenital pseudarthrosis of the tibia," *J. Bone Joint Surg. Br.* 91-B, Supp. 1, abstract 137 (2009).
Srinivas, et al., "Assessment of dose proportionality, absolute bioavailability, and immunogenicity response of CTLA4Ig (BMS-188667), a novel immunosuppressive agent, following subcutaneous and intravenous administration to rats," *Pharmaceutical Res.* 14(7): 911-916 (1997).

Tye et al., "Delineation of the hydroxyapatite-nucleating domains of bone sialoprotein," *J. Biol. Chem.* 278(10): 7949-7955 (2003).
Urlaub et al., "Deletion of the diploid dihydrofolate reductase locus from cultured mammalian cells," *Cell* 33: 405-412 (1983).
Wang et al., "A mouse model for achondroplasia produced by targeting fibroblast growth factor receptor 3," *Proc. Natl. Acad. Sci.* 96: 4455-4460 (1999).
Wang et al., "Structure-based chemical modification strategy for enzyme replacement treatment of phenylketonuria," *Mol. Gen. and Metab.* 86: 134-140 (2005).
Weiss et al., "A missense mutation in the human liver/ bone/ kidney alkaline phosphatase gene causing a lethal form of hypophosphatasia," *Proc. Natl. Acad. Sci.* 85: 7666-7669 (1988).
Whyte et al., "Enzyme-replacement therapy in life-threatening hypophosphatasia," *N. Engl. J. Med.* 366(10): 904-913 (2012).
Whyte, "Hypophosphatasia: Nature's window on alkaline phosphatase function in man," in *Principles of Bone Biology*, 2$^{nd}$ ed., vol. 2, eds. JJ Bilezikian, LG Raisz, and GA Rodan. London: Academic Press, 2002: 1229-1248.
Whyte et al., "Markedly increased circulating pyridoxal-5'-phosphate levels in hypophosphatasia," *J. Clin. Invest.* 76: 752-756 (1985).
Wroblewski et al., "Pharmacokinetics, metabolic stability, and subcutaneous bioavailability of a genetically engineered analog of DcR3, flint [DcR3(R218Q)], in cynomolgus monkeys and mice," *Drug. Metab. Dispos.* 31: 502-507 (2003).
Yamamoto et al., "Long term phenotypic correction of severe infantile hypophosphatasia in a mouse model by neonatal injection of lentiviral vector," *Molecular Therapy* 17: S67-S68, Abstract 171 (2009).
Zierhut, et al., "Population PK-PD model for Fc-osteoprotegerin in healthy postmenopausal women," *J. Pharmacokinet. Pharmacodyn.* 35: 379-399 (2008).
Zurutuza et al., "Correlations of genotype and phenotype in hypophosphatasia," *Hum. Mol. Genet.* 8(6): 1039-1046 (1999).
International Preliminary Report on Patentability and Written Opinion for International Application No. PCT/CA2011/050258, dated Nov. 15, 2012 (9 pages).
International Search Report and Written Opinion for International Application No. PCT/US12/39004, dated Nov. 2, 2012 (22 pages).
Invitation to Pay Additional Fees for International Application No. PCT/US12/39004, dated Aug. 29, 2012 (2 pages).
Oikawa et al., "Enzyme replacement therapy on hypophosphatasia mouse model," J Inherit Metab Dis. 9 pages (2013).

\* cited by examiner

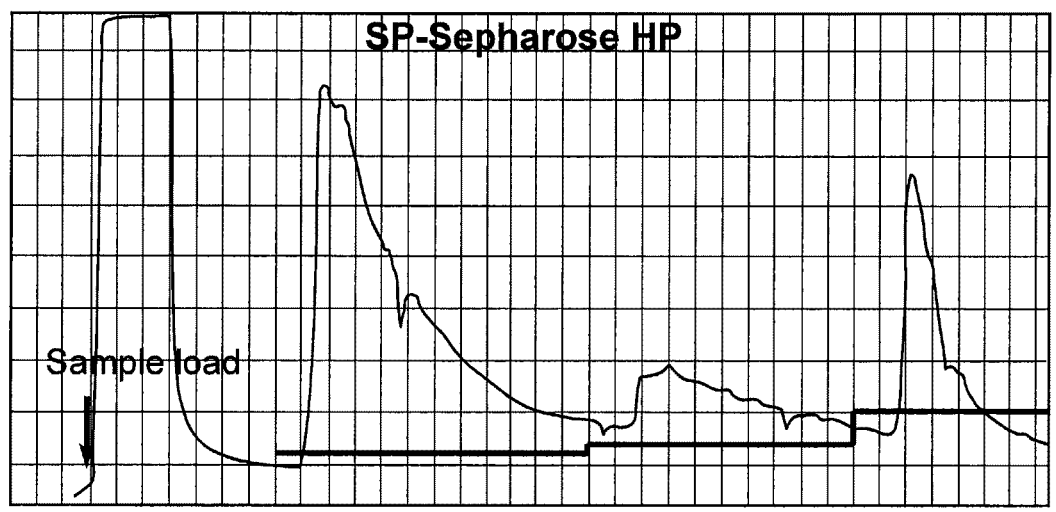
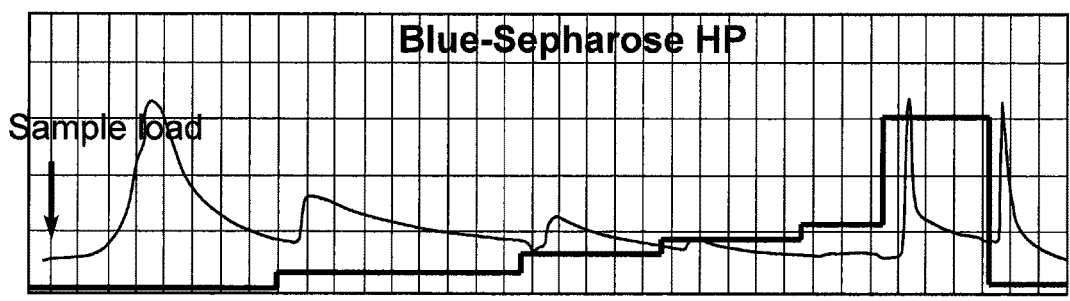
Figure 4

```
atggaagcagaaacagggagcagcgtggagactggaaagaaggccaacagaggcactcgaattgccctgg
tcgtgtttgtcctgacagtgatcgctcaacaaacaaccagtcaaggtctcttatccggagatgacgatga
cgatgacgatgacgatgactccggaagtctccaagctaaacaggagtactgcctgaagccagaatgcatc
gaagcggctgctgccatcttaagtaaagtaaatctgtctgtggatccttgtgataatttcttccggttcg
cttgtgatggctggataagcaataatccaattcccgaagatatgccaagctatggggtttatccttggct
gagacataatgttgacctcaagttgaaggaacttttggagaaatcaatcagtagaaggcgggacaccgaa
gccatacagaaagccaaaatcctttattcatcctgcatgaatgagaaagcgattgaaaaagcagatgcca
agccactgctacacatcctacggcattcacctttccgctggcccgtgcttgaatctaatattggccctga
aggggtttggtcagagagaaagttcagccttctgcagacacttgcaacgtttcgtggtcaatacagcaat
tctgtgttcatccgtttgtatgtgtcccctgatgacaaagcatccaatgaacatatcttgaagctggacc
aagcaacactctccctggccgtgagggaagactaccttgataacagtacagaagccaagtcttatcggga
tgcccttacaagttcatggtggatactgccgtgcttttaggagctaacagttccagagcagagcatgac
atgaagtcagtgctcagattggaaattaagatagctgagataatgattccacatgaaaaccgaaccagcg
aggccatgtacaacaaaatgaacatttctgaactgagtgctatgattccccagttcgactggctgggcta
catcaagaaggtcattgacaccagactctaccccatctgaaagacatcagcccctccgagaatgtggtg
gtccgcgtcccgcagtactttaaagatttgtttaggatattagggtctgagagaaagaagaccattgcca
actatttggtgtggagaatggtttattccagaattccaaaccttagcaggcgctttcagtatagatggct
ggaattctcaagggtaatccaggggaccacaactttgctgcctcaatgggacaaatgtgtaaactttatt
gaaagtgccctcccttatgttgttggaaagatgtttgtagatgtgtacttccaggaagataagaaggaaa
tgatggaggaattggttgagggcgttcgctgggcctttattgacatgctagagaaagaaatgagtggat
ggatgcaggaacgaaaaggaaagccaaagaaaaggcgagagctgttttggcaaaagttggctatccagag
tttataatgaatgatactcatgttaatgaagacctcaaagctatcaagttttcagaagccgactactttg
gcaacgtcctacaaactcgcaagtatttagcacagtctgatttcttctggctaagaaaagccgttccaaa
aacagagtggtttacaaatccgacgactgtcaatgccttctacagtgcatccaccaaccagatccgattt
ccagcaggagagctccagaagcctttcttttggggaacagaatatcctcgatctctgagttatggtgcta
taggagtaattgtcggacatgaatttacacatggatttgataataatggtagaaaatatgataaaaatgg
aaacctggatccttggtggtctactgaatcagaagaaaagtttaaggaaaaaacaaaatgcatgattaac
cagtatagcaactattattggaagaaagctggcttaaatgtcaaggggaagaggaccctgggagaaaata
ttgctgataatggaggcctgcgggaagcttttagggcttacaggaaatggataaatgacagaaggcaggg
acttgaggagcctcttctaccaggcatcacattcaccaacaaccagctcttcttcctgagttatgctcat
gtgaggtgcaattcctacagaccagaagctgcccgagaacaagtccaaattggtgctcacagtcccctc
agtttagggtcaatggtgcaattagtaactttgaagaattccagaaagcttttaactgtccacccaattc
cacgatgaacagaggcatggactcctgccgactctggtag
```

Figure 7

```
MEAETGSSVETGKKANRGTRIALVVFVLTVIAQQTTSQGLLSGDDDDDDDDDSGSLQAKQEYCLKPECI
EAAAAILSKVNLSVDPCDNFFRFACDGWISNNPIPEDMPSYGVYPWLRHNVDLKLKELLEKSISRRRDTE
AIQKAKILYSSCMNEKAIEKADAKPLLHILRHSPFRWPVLESNIGPEGVWSERKFSLLQTLATFRGQYSN
SVFIRLYVSPDDKASNEHILKLDQATLSLAVREDYLDNSTEAKSYRDALYKFMVDTAVLLGANSSRAEHD
MKSVLRLEIKIAEIMIPHENRTSEAMYNKMNISELSAMIPQFDWLGYIKKVIDTRLYPHLKDISPSENVV
VRVPQYFKDLFRILGSERKKTIANYLVWRMVYSRIPNLSRRFQYRWLEFSRVIQGTTTLLPQWDKCVNFI
ESALPYVVGKMFVDVYFQEDKKEMMEELVEGVRWAFIDMLEKENEWMDAGTKRKAKEKARAVLAKVGYPE
FIMNDTHVNEDLKAIKFSEADYFGNVLQTRKYLAQSDFFWLRKAVPKTEWFTNPTTVNAFYSASTNQIRF
PAGELQKPFFWGTEYPRSLSYGAIGVIVGHEFTHGFDNNGRKYDKNGNLDPWWSTESEEKFKEKTKCMIN
QYSNYYWKKAGLNVKGKRTLGENIADNGGLREAFRAYRKWINDRRQGLEEPLLPGITFTNNQLFFLSYAH
VRCNSYRPEAAREQVQIGAHSPPQFRVNGAISNFEEFQKAFNCPPNSTMNRGMDSCRLW
```

Figure 8

```
  1 MEAETGSSVE TGKKANRGTR IALVVFVGGT LVLGTILFLV SQGLLSLQAK QEYCLKPECI
 61 EAAAAILSKV NLSVDPCDNF FRFACDGWIS NNPIPEDMPS YGVYPWLRHN VDLKLKELLE
121 KSISRRRDTE AIQKAKILYS SCMNEKAIEK ADAKPLLHIL RHSPFRWPVL ESNIGPEGVW
181 SERKFSLLQT LATFRGQYSN SVFIRLYVSP DDKASNEHIL KLDQATLSLA VREDYLDNST
241 EAKSYRDALY KFMVDTAVLL GANSSRAEHD MKSVLRLEIK IAEIMIPHEN RTSEAMYNKM
301 NISELSAMIP QFDWLGYIKK VIDTRLYPHL KDISPSENVV VRVPQYFKDL FRILGSERKK
361 TIANYLVWRM VYSRIPNLSR RFQYRWLEFS RVIQGTTTLL PQWDKCVNFI ESALPYVVGK
421 MFVDVYFQED KKEMMEELVE GVRWAFIDML EKENEWMDAG TKRKAKEKAR AVLAKVGYPE
481 FIMNDTHVNE DLKAIKFSEA DYFGNVLQTR KYLAQSDFFW LRKAVPKTEW FTNPTTVNAF
541 YSASTNQIRF PAGELQKPFF WGTEYPRSLS YGAIGVIVGH EFTHGFDNNG RKYDKNGNLD
601 PWWSTESEEK FKEKTKCMIN QYSNYYWKKA GLNVKGKRTL GENIADNGGL REAFRAYRKW
661 INDRRQGLEE PLLPGITFTN NQLFFLSYAH VRCNSYRPEA AREQVQIGAH SPPQFRVNGA
721 ISNSEEFQKA FNCPPNSTMN RGMDSCRLW
```

Figure 10

```
SGDDDDDDDDDDSGSLQAKQEYCLKPECIEAAAAILSKVNLSVDPCDNFFRFACDGWISNNPIPEDMPSY
GVYPWLRHNVDLKLKELLEKSISRRRDTEAIQKAKILYSSCMNEKAIEKADAKPLLHILRHSPFRWPVLE
SNIGPEGVWSERKFSLLQTLATFRGQYSNSVFIRLYVSPDDKASNEHILKLDQATLSLAVREDYLDNSTE
AKSYRDALYKFMVDTAVLLGANSSRAEHDMKSVLRLEIKIAEIMIPHENRTSEAMYNKMNISELSAMIPQ
FDWLGYIKKVIDTRLYPHLKDISPSENVVVRVPQYFKDLFRILGSERKKTIANYLVWRMVYSRIPNLSRR
FQYRWLEFSRVIQGTTTLLPQWDKCVNFIESALPYVVGKMFVDVYFQEDKKEMMEELVEGVRWAFIDMLE
KENEWMDAGTKRKAKEKARAVLAKVGYPEFIMNDTHVNEDLKAIKFSEADYFGNVLQTRKYLAQSDFFWL
RKAVPKTEWFTNPTTVNAFYSASTNQIRFPAGELQKPFFWGTEYPRSLSYGAIGVIVGHEFTHGFDNNGR
KYDKNGNLDPWWSTESEEKFKEKTKCMINQYSNYYWKKAGLNVKGKRTLGENIADNGGLREAFRAYRKWI
NDRRQGLEEPLLPGITFTNNQLFFLSYAHVRCNSYRPEAAREQVQIGAHSPPQFRVNGAISNFEEFQKAF
NCPPNSTMNRGMDSCRLW
```

Figure 11

| | Protein construct | Specific activity (UAF/sec/μg) | Schematic representation |
|---|---|---|---|
| 1 | sPHEX | 12.3 | SLQAK...(SEQ ID NO: 45)  |
| 2 | Fc-sPHEX | 5.75 | TSDKTH... SLQAK...(SEQ ID NO: 46)  |
| 3 | pCDNA3-RSV-NL1furin-sPHEX | N/A | SVSLQAK...(SEQ ID NO: 47)  |
| 4 | D$_{10}$sPHEX | 12.0 | SGDDDDDDDDDDSGSLQAK...(SEQ ID NO: 48)  |
| 5 | D$_6$sPHEX | 8.55 | SDDDDDDYVSLQAK...(SEQ ID NO: 49)  |

▨ : Represents the mutated transmembrane domain of PHEX.

■ : Represents the human IgG1 signal peptide.

▨ : Represents the human IgG1 heavy chain domains hinge, CH2 and CH3.

▨ : 1 N-terminal sequence with the furin cleavage site (RTVVKR↓SV; SEQ ID NO: 50).

| : Furin cleavage site.

| :peptidase signal cleavage site

```
         BamHI
         ~~~~~~
    1    GGATCCACCA TGATTTCACC ATTCTTAGTA CTGGCCATTG GCACCTGCCT TACTAACTCC TTAGTGCCAG
   71    AGAAAGAGAA AGACCCCAAG TACTGGCGAG ACCAAGCGCA AGAGACACTG AAATATGCCC TGGAGCTTCA
  141    GAAGCTCAAC ACCAACGTGG CTAAGAATGT CATCATGTTC CTGGGAGATG GGATGGGTGT CTCCACAGTG
  211    ACGGCTGCCC GCATCCTCAA GGGTCAGCTC CACCACAACC TGGGGAGGA GACCAGGCTG GAGATGGACA
  281    AGTTCCCCTT CGTGGCCCTC TCCAAGACGT ACAACACCAA TGCCCAGGTC CCTGACAGCG CCGGCACCGC
  351    CACCGCCTAC CTGTGTGGGG TGAAGGCCAA TGAGGGCACC GTGGGGGTAA GCGCAGCCAC TGAGCGTTCC
  421    CGGTGCAACA CCACCCAGGG GAACGAGGTC ACCTCCATCC TGCGCTGGGC CAAGGACGCT GGGAAATCTG
  491    TGGGCATTGT GACCACCACG AGAGTGAACC ATGCCACCCC CAGCGCCGCC TACGCCCACT CGGCTGACCG
  561    GGACTGGTAC TCAGACAACG AGATGCCCCC TGAGGCCTTG AGCCAGGGCT GTAAGGACAT CGCCTACCAG
  631    CTCATGCATA ACATCAGGGA CATTGACGTG ATCATGGGGG GTGGCCGGAA ATACATGTAC CCCAAGAATA
  701    AAACTGATGT GGAGTATGAG AGTGACGAGA AAGCCAGGGG CACGAGGCTG GACGGCCTGG ACCTCGTTGA
  771    CACCTGGAAG AGCTTCAAAC CGAGATACAA GCACTCCCAC TTCATCTGGA ACCGCACGGA ACTCCTGACC
  841    CTTGACCCCC ACAATGTGGA CTACCTATTG GGTCTCTTCG AGCCAGGGGA CATGCAGTAC GAGCTGAACA
  911    GGAACAACGT GACGGACCCG TCACTCTCCG AGATGGTGGT GGTGGCCATC CAGATCCTGC GGAAGAACCC
  981    CAAAGGCTTC TTCTTGCTGG TGGAAGGAGG CAGAATTGAC CACGGGCACC ATGAAGGAAA AGCCAAGCAG
 1051    GCCCTGCATG AGGCGGTGGA GATGGACCGG GCCATCGGGC AGGCAGGCAG CTTGACCTCC TCGGAAGACA
 1121    CTCTGACCGT GGTCACTGCG GACCATTCCC ACGTCTTCAC ATTTGGTGGA TACACCCCCC GTGGCAACTC
 1191    TATCTTTGGT CTGGCCCCCA TGCTGAGTGA CACAGACAAG AAGCCCTTCA CTGCCATCCT GTATGGCAAT
 1261    GGGCCTGGCT ACAAGGTGGT GGGCGGTGAA CGAGAGAATG TCTCCATGGT GGACTATGCT CACAACAACT
 1331    ACCAGGCGCA GTCTGCTGTG CCCCTGCGCC ACGAGACCCA CGGCGGGGAG GACGTGGCCG TCTTCTCCAA
 1401    GGGCCCCATG GCGCACCTGC TGCACGGCGT CCACGAGCAG AACTACGTCC CCCACGTGAT GGCGTATGCA
                                                                        XbaI
                                                                        ~~~~~~
 1471    GCCTGCATCG GGGCCAACCT CGGCCACTGT GCTCCTGCCA GCTCGTAGTC TAGA
```

B

```
    1    MISPFLVLAI GTCLTNSLVP EKEKDPKYWR DQAQETLKYA LELQKLNTNV
   51    AKNVIMFLGD GMGVSTVTAA RILKGQLHHN PGEETRLEMD KFPFVALSKT
  101    YNTNAQVPDS AGTATAYLCG VKANEGTVGV SAATERSRCN TTQGNEVTSI
  151    LRWAKDAGKS VGIVTTTRVN HATPSAAYAH SADRDWYSDN EMPPEALSQG
  201    CKDIAYQLMH NIRDIDVIMG GGRKYMYPKN KTDVEYESDE KARGTRLDGL
  251    DLVDTWKSFK PRYKHSHFIW NRTELLTLDP HNVDYLLGLF EPGDMQYELN
  301    RNNVTDPSLS EMVVVAIQIL RKNPKGFFLL VEGGRIDHGH HEGKAKQALH
  351    EAVEMDRAIG QAGSLTSSED TLTVVTADHS HVFTFGGYTP RGNSIFGLAP
  401    MLSDTDKKPF TAILYGNGPG YKVVGGEREN VSMVDYAHNN YQAQSAVPLR
  451    HETHGGEDVA VFSKGPMAHL LHGVHEQNYV PHVMAYAACI GANLGHCAPA
  501    SS
```

```
            BamHI
            ------
   1    GGATCCACCA TGATTTCACC ATTCTTAGTA CTGGCCATTG GCACCTGCCT TACTAACTCC TTAGTGCCAG
  71    AGAAAGAGAA AGACCCCAAG TACTGGCGAG ACCAAGCGCA AGAGACACTG AAATATGCCC TGGAGCTTCA
 141    GAAGCTCAAC ACCAACGTGG CTAAGAATGT CATCATGTTC CTGGGAGATG GGATGGGTGT CTCCACAGTG
 211    ACGGCTGCCC GCATCCTCAA GGGTCAGCTC CACCACAACC CTGGGGAGGA GACCAGGCTG GAGATGGACA
 281    AGTTCCCCTT CGTGGCCCTC TCCAAGACGT ACAACACCAA TGCCCAGGTC CCTGACAGCG CCGGCACCGC
 351    CACCGCCTAC CTGTGTGGGG TGAAGGCCAA TGAGGGCACC GTGGGGGTAA GCGCAGCCAC TGAGCGTTCC
 421    CGGTGCAACA CCACCCAGGG GAACGAGGTC ACCTCCATCC TGCGCTGGGC CAAGGACGCT GGGAAATCTG
 491    TGGGCATTGT GACCACCACG AGAGTGAACC ATGCCACCCC CAGCGCCGCC TACGCCCACT CGGCTGACCG
 561    GGACTGGTAC TCAGACAACG AGATGCCCCC TGAGGCCTTG AGCCAGGGCT GTAAGGACAT CGCCTACCAG
 631    CTCATGCATA ACATCAGGGA CATTGACGTG ATCATGGGGG GTGGCCGGAA ATACATGTAC CCCAAGAATA
 701    AAACTGATGT GGAGTATGAG AGTGACGAGA AAGCCAGGGG CACGAGGCTG GACGGCCTGG ACCTCGTTGA
 771    CACCTGGAAG AGCTTCAAAC CGAGATACAA GCACTCCCAC TTCATCTGGA ACCGCACGGA ACTCCTGACC
 841    CTTGACCCCC ACAATGTGGA CTACCTATTG GGTCTCTTCG AGCCAGGGGA CATGCAGTAC GAGCTGAACA
 911    GGAACAACGT GACGGACCCG TCACTCTCCG AGATGGTGGT GGTGGCCATC CAGATCCTGC GGAAGAACCC
 981    CAAAGGCTTC TTCTTGCTGG TGGAAGGAGG CAGAATTGAC CACGGGCACC ATGAAGGAAA AGCCAAGCAG
1051    GCCCTGCATG AGGCGGTGGA GATGGACCGG GCCATCGGGC AGGCAGGCAG CTTGACCTCC TCGGAAGACA
1121    CTCTGACCGT GGTCACTGCG GACCATTCCC ACGTCTTCAC ATTTGGTGGA TACACCCCCC GTGGCAACTC
1191    TATCTTTGGT CTGGCCCCCA TGCTGAGTGA CACAGACAAG AAGCCCTTCA CTGCCATCCT GTATGGCAAT
1261    GGGCCTGGCT ACAAGGTGGT GGGCGGTGAA CGAGAGAATG TCTCCATGGT GGACTATGCT CACAACAACT
1331    ACCAGGCGCA GTCTGCTGTG CCCCTGCGCC ACGAGACCCA CGGCGGGGAG GACGTGGCCG TCTTCTCCAA
1401    GGGCCCCATG GCGCACCTGC TGCACGGCGT CCACGAGCAG AACTACGTCC CCCACGTGAT GGCGTATGCA
1471    GCCTGCATCG GGGCCAACCT CGGCCACTGT GCTCCTGCCA GCTCGGATGA CGACGATGAT GACGATGATG
            XbaI
            ------
1541    ACGACTAGTC TAGA
```

B

```
   1    MISPFLVLAI GTCLTNSLVP EKEKDPKYWR DQAQETLKYA LELQKLNTNV
  51    AKNVIMFLGD GMGVSTVTAA RILKGQLHHN PGEETRLEMD KFPFVALSKT
 101    YNTNAQVPDS AGTATAYLCG VKANEGTVGV SAATERSRCN TTQGNEVTSI
 151    LRWAKDAGKS VGIVTTTRVN HATPSAAYAH SADRDWYSDN EMPPEALSQG
 201    CKDIAYQLMH NIRDIDVIMG GGRKYMYPKN KTDVEYESDE KARGTRLDGL
 251    DLVDTWKSFK PRYKHSHFIW NRTELLTLDP HNVDYLLGLF EPGDMQYELN
 301    RNNVTDPSLS EMVVVAIQIL RKNPKGFFLL VEGGRIDHGH HEGKAKQALH
 351    EAVEMDRAIG QAGSLTSSED TLTVVTADHS HVFTFGGYTP RGNSIFGLAP
 401    MLSDTDKKPF TAILYGNGPG YKVVGGEREN VSMVDYAHNN YQAQSAVPLR
 451    HETHGGEDVA VFSKGPMAHL LHGVHEQNYV PHVMAYAACI GANLGHCAPA
 501    SSDDDDDDDD DD
```

Figure 17

SEQUENCE LISTING

```
<160> NUMBER OF SEQ ID NOS: 50

<210> SEQ ID NO 1
<211> LENGTH: 2280
<212> TYPE: DNA
<213> ORGANISM: Artificial Sequence
<220> FEATURE:
<223> OTHER INFORMATION: Encoding cleavable conjugate

<400> SEQUENCE: 1
atggaagcag aaacagggag cagcgtggag actggaaaga aggccaacag aggcactcga      60
attgccctgg tcgtgtttgt cctgacagtg atcgctcaac aaacaaccag tcaaggtctc     120
ttatccggag atgacgatga cgatgacgat gacgatgact ccggaagtct ccaagctaaa     180
caggagtact gcctgaagcc agaatgcatc gaagcggctc tgccatctt aagtaaagta     240 aatctgtctg tggatccttg tgataatttc ttccggttcg cttgtgatgg ctggataagc     300
aataatccaa ttcccgaaga tatgccaagc tatgggtttt atccttggct gagacataat     360
gttgacctca agttgaagga acttttggag aaatcaatca gtagaaggcg ggacaccgaa     420
gccatacaga aagccaaaat cctttattca tcctgcatga atgagaaagc gattgaaaaa     480
gcagatgcca agccactgct acacatccta cggcattcac ctttccgctg gcccgtgctt     540
gaatctaata ttggccctga aggggtttgg tcagagagaa agttcagcct tctgcagaca     600
cttgcaacgt tcgtggtca atacagcaat tctgtgttca tccgtttgta tgtgtccct     660 gatgacaaag catccaatga acatatcttg aagctggacc aagcaacact ctccctggcc     720
gtgagggaag actaccttga taacagtaca gaagccaagt cttatcggga tgcccttac     780 aagttcatgg tggatactgc cgtgcttta ggagctaaca gttccagagc agagcatgac     840
atgaagtcag tgctcagatt ggaaattaag atagctgaga taatgattcc acatgaaaac     900
cgaaccagcg aggccatgta caacaaaatg aacatttctg aactgagtgc tatgattccc     960
cagttcgact ggctgggcta catcaagaag gtcattgaca ccagactcta cccccatctg    1020
aaagacatca gcccctccga gaatgtggtg gtccgcgtcc cgcagtactt aaagatttg    1080 tttaggatat tagggtctga gagaagaag accattgcca actatttggt gtggagaatg    1140
gtttattcca gaattccaaa ccttagcagg cgctttcagt atagatggct ggaattctca    1200
```

-continued

```
agggtaatcc aggggaccac aactttgctg cctcaatggg acaaatgtgt aaactttatt   1260
gaaagtgccc tcccttatgt tgttggaaag atgtttgtag atgtgtactt ccaggaagat   1320
aagaaggaaa tgatggagga attggttgag ggcgttcgct gggcctttat tgacatgcta   1380
gagaaagaaa atgagtggat ggatgcagga acgaaaagga aagccaaaga aaaggcgaga   1440
gctgttttgg caaaagttgg ctatccagag tttataatga atgatactca tgttaatgaa   1500
gacctcaaag ctatcaagtt ttcagaagcc gactactttg caacgtcct acaaactcgc    1560 aagtatttag cacagtctga tttcttctgg ctaagaaaag ccgttccaaa aacagagtgg   1620
tttacaaatc cgacgactgt caatgccttc tacagtgcat ccaccaacca gatccgattt   1680
ccagcaggag agctccagaa gcctttcttt tggggaacag aatatcctcg atctctgagt   1740
tatggtgcta taggagtaat tgtcggacat gaatttacac atggatttga taataatggt   1800
agaaaatatg ataaaaatgg aaacctggat ccttggtggt ctactgaatc agaagaaaag   1860
tttaaggaaa aaacaaaatg catgattaac cagtatagca actattattg gaagaaagct   1920
ggcttaaatg tcaaggggaa gaggaccctg ggagaaaata ttgctgataa tggaggcctg   1980
cgggaagctt ttagggctta caggaaatgg ataaatgaca gaaggcaggg acttgaggag   2040
cctcttctac caggcatcac attcaccaac aaccagctct tcttcctgag ttatgctcat   2100
gtgaggtgca attcctacag accagaagct gcccgagaac aagtccaaat tggtgctcac   2160
agtccccctc agtttagggt caatggtgca attagtaact ttgaagaatt ccagaaagct   2220
tttaactgtc cacccaattc cacgatgaac agaggcatgg actcctgccg actctggtag   2280
```

<210> SEQ ID NO 2
<211> LENGTH: 759
<212> TYPE: PRT
<213> ORGANISM: Artificial Sequence
<220> FEATURE:
<223> OTHER INFORMATION: Cleavable PHEX conjugate

<400> SEQUENCE: 2

```
Met Glu Ala Glu Thr Gly Ser Ser Val Glu Thr Gly Lys Lys Ala Asn
1               5                   10                  15

Arg Gly Thr Arg Ile Ala Leu Val Val Phe Val Leu Thr Val Ile Ala
                20                  25                  30

Gln Gln Thr Thr Ser Gln Gly Leu Leu Ser Gly Asp Asp Asp Asp
            35                  40                  45

Asp Asp Asp Asp Asp Ser Gly Ser Leu Gln Ala Lys Gln Glu Tyr Cys
        50                  55                  60

Leu Lys Pro Glu Cys Ile Glu Ala Ala Ala Ile Leu Ser Lys Val
65                  70                  75                  80

Asn Leu Ser Val Asp Pro Cys Asp Asn Phe Phe Arg Phe Ala Cys Asp
                85                  90                  95

Gly Trp Ile Ser Asn Asn Pro Ile Pro Glu Asp Met Pro Ser Tyr Gly
                100                 105                 110

Val Tyr Pro Trp Leu Arg His Asn Val Asp Leu Lys Leu Lys Glu Leu
            115                 120                 125

Leu Glu Lys Ser Ile Ser Arg Arg Asp Thr Glu Ala Ile Gln Lys
        130                 135                 140

Ala Lys Ile Leu Tyr Ser Ser Cys Met Asn Glu Lys Ala Ile Glu Lys
145                 150                 155                 160

Ala Asp Ala Lys Pro Leu Leu His Ile Leu Arg His Ser Pro Phe Arg
                165                 170                 175
```

-continued

```
Trp Pro Val Leu Glu Ser Asn Ile Gly Pro Glu Gly Val Trp Ser Glu
            180                 185                 190

Arg Lys Phe Ser Leu Leu Gln Thr Leu Ala Thr Phe Arg Gly Gln Tyr
            195                 200                 205

Ser Asn Ser Val Phe Ile Arg Leu Tyr Val Ser Pro Asp Asp Lys Ala
            210                 215                 220

Ser Asn Glu His Ile Leu Lys Leu Asp Gln Ala Thr Leu Ser Leu Ala
225                 230                 235                 240

Val Arg Glu Asp Tyr Leu Asp Asn Ser Thr Glu Ala Lys Ser Tyr Arg
                245                 250                 255

Asp Ala Leu Tyr Lys Phe Met Val Asp Thr Ala Val Leu Leu Gly Ala
            260                 265                 270

Asn Ser Ser Arg Ala Glu His Asp Met Lys Ser Val Leu Arg Leu Glu
            275                 280                 285

Ile Lys Ile Ala Glu Ile Met Ile Pro His Glu Asn Arg Thr Ser Glu
            290                 295                 300

Ala Met Tyr Asn Lys Met Asn Ile Ser Glu Leu Ser Ala Met Ile Pro
305                 310                 315                 320

Gln Phe Asp Trp Leu Gly Tyr Ile Lys Lys Val Ile Asp Thr Arg Leu
                325                 330                 335

Tyr Pro His Leu Lys Asp Ile Ser Pro Ser Glu Asn Val Val Val Arg
            340                 345                 350

Val Pro Gln Tyr Phe Lys Asp Leu Phe Arg Ile Leu Gly Ser Glu Arg
            355                 360                 365

Lys Lys Thr Ile Ala Asn Tyr Leu Val Trp Arg Met Val Tyr Ser Arg
            370                 375                 380

Ile Pro Asn Leu Ser Arg Arg Phe Gln Tyr Arg Trp Leu Glu Phe Ser
385                 390                 395                 400

Arg Val Ile Gln Gly Thr Thr Thr Leu Leu Pro Gln Trp Asp Lys Cys
                405                 410                 415

Val Asn Phe Ile Glu Ser Ala Leu Pro Tyr Val Val Gly Lys Met Phe
            420                 425                 430

Val Asp Val Tyr Phe Gln Glu Asp Lys Lys Glu Met Met Glu Glu Leu
            435                 440                 445

Val Glu Gly Val Arg Trp Ala Phe Ile Asp Met Leu Glu Lys Glu Asn
450                 455                 460

Glu Trp Met Asp Ala Gly Thr Lys Arg Lys Ala Lys Glu Lys Ala Arg
465                 470                 475                 480

Ala Val Leu Ala Lys Val Gly Tyr Pro Glu Phe Ile Met Asn Asp Thr
                485                 490                 495

His Val Asn Glu Asp Leu Lys Ala Ile Lys Phe Ser Gly Ala Asp Tyr
            500                 505                 510

Phe Gly Asn Val Leu Gln Thr Arg Lys Tyr Leu Ala Gln Ser Asp Phe
            515                 520                 525

Phe Trp Leu Arg Lys Ala Val Pro Lys Thr Glu Trp Phe Thr Asn Pro
            530                 535                 540

Thr Thr Val Asn Ala Phe Tyr Ser Ala Ser Thr Asn Gln Ile Arg Phe
545                 550                 555                 560

Pro Ala Gly Glu Leu Gln Lys Pro Phe Phe Trp Gly Thr Glu Tyr Pro
                565                 570                 575

Arg Ser Leu Ser Tyr Gly Ala Ile Gly Val Ile Val Gly His Glu Phe
            580                 585                 590
```

```
Thr His Gly Phe Asp Asn Asn Gly Arg Lys Tyr Asp Lys Asn Gly Asn
            595                 600                 605

Leu Asp Pro Trp Trp Ser Thr Glu Ser Glu Lys Phe Lys Glu Lys
610                 615                 620

Thr Lys Cys Met Ile Asn Gln Tyr Ser Asn Tyr Tyr Trp Lys Lys Ala
625                 630                 635                 640

Gly Leu Asn Val Lys Gly Lys Arg Thr Leu Gly Glu Asn Ile Ala Asp
            645                 650                 655

Asn Gly Gly Leu Arg Glu Ala Phe Arg Ala Tyr Arg Lys Trp Ile Asn
                660                 665                 670

Asp Arg Arg Gln Gly Leu Glu Glu Pro Leu Leu Pro Gly Ile Thr Phe
            675                 680                 685

Thr Asn Asn Gln Leu Phe Phe Leu Ser Tyr Ala His Val Arg Cys Asn
            690                 695                 700

Ser Tyr Arg Pro Glu Ala Ala Arg Glu Gln Val Gln Ile Gly Ala His
705                 710                 715                 720

Ser Pro Pro Gln Phe Arg Val Asn Gly Ala Ile Ser Asn Phe Glu Glu
                725                 730                 735

Phe Gln Lys Ala Phe Asn Cys Pro Pro Asn Ser Thr Met Asn Arg Gly
            740                 745                 750

Met Asp Ser Cys Arg Leu Trp
            755

<210> SEQ ID NO 3
<211> LENGTH: 749
<212> TYPE: PRT
<213> ORGANISM: Homo sapiens

<400> SEQUENCE: 3

Met Glu Ala Glu Thr Gly Ser Ser Val Glu Thr Gly Lys Lys Ala Asn
1               5                   10                  15

Arg Gly Thr Arg Ile Ala Leu Val Val Phe Val Gly Gly Thr Leu Val
            20                  25                  30

Leu Gly Thr Ile Leu Phe Leu Val Ser Gln Gly Leu Leu Ser Leu Gln
            35                  40                  45

Ala Lys Gln Glu Tyr Cys Leu Lys Pro Glu Cys Ile Glu Ala Ala Ala
50                  55                  60

Ala Ile Leu Ser Lys Val Asn Leu Ser Val Asp Pro Cys Asp Asn Phe
65                  70                  75                  80

Phe Arg Phe Ala Cys Asp Gly Trp Ile Ser Asn Asn Pro Ile Pro Glu
                85                  90                  95

Asp Met Pro Ser Tyr Gly Val Tyr Pro Trp Leu Arg His Asn Val Asp
            100                 105                 110

Leu Lys Leu Lys Glu Leu Leu Glu Lys Ser Ile Ser Arg Arg Arg Asp
            115                 120                 125

Thr Glu Ala Ile Gln Lys Ala Lys Ile Leu Tyr Ser Ser Cys Met Asn
            130                 135                 140

Glu Lys Ala Ile Glu Lys Ala Asp Ala Lys Pro Leu Leu His Ile Leu
145                 150                 155                 160

Arg His Ser Pro Phe Arg Trp Pro Val Leu Glu Ser Asn Ile Gly Pro
                165                 170                 175

Glu Gly Val Trp Ser Glu Arg Lys Phe Ser Leu Leu Gln Thr Leu Ala
            180                 185                 190

Thr Phe Arg Gly Gln Tyr Ser Asn Ser Val Phe Ile Arg Leu Tyr Val
            195                 200                 205
```

-continued

```
Ser Pro Asp Asp Lys Ala Ser Asn Glu His Ile Leu Lys Leu Asp Gln
    210                 215                 220

Ala Thr Leu Ser Leu Ala Val Arg Glu Asp Tyr Leu Asp Asn Ser Thr
225                 230                 235                 240

Glu Ala Lys Ser Tyr Arg Asp Ala Leu Tyr Lys Phe Met Val Asp Thr
                245                 250                 255

Ala Val Leu Leu Gly Ala Asn Ser Ser Arg Ala Glu His Asp Met Lys
            260                 265                 270

Ser Val Leu Arg Leu Glu Ile Lys Ile Ala Glu Ile Met Ile Pro His
        275                 280                 285

Glu Asn Arg Thr Ser Glu Ala Met Tyr Asn Lys Met Asn Ile Ser Glu
    290                 295                 300

Leu Ser Ala Met Ile Pro Gln Phe Asp Trp Leu Gly Tyr Ile Lys Lys
305                 310                 315                 320

Val Ile Asp Thr Arg Leu Tyr Pro His Leu Lys Asp Ile Ser Pro Ser
                325                 330                 335

Glu Asn Val Val Val Arg Val Pro Gln Tyr Phe Lys Asp Leu Phe Arg
            340                 345                 350

Ile Leu Gly Ser Glu Arg Lys Lys Thr Ile Ala Asn Tyr Leu Val Trp
        355                 360                 365

Arg Met Val Tyr Ser Arg Ile Pro Asn Leu Ser Arg Arg Phe Gln Tyr
    370                 375                 380

Arg Trp Leu Glu Phe Ser Arg Val Ile Gln Gly Thr Thr Thr Leu Leu
385                 390                 395                 400

Pro Gln Trp Asp Lys Cys Val Asn Phe Ile Glu Ser Ala Leu Pro Tyr
                405                 410                 415

Val Val Gly Lys Met Phe Val Asp Val Tyr Phe Gln Glu Asp Lys Lys
            420                 425                 430

Glu Met Met Glu Glu Leu Val Glu Gly Val Arg Trp Ala Phe Ile Asp
        435                 440                 445

Met Leu Glu Lys Glu Asn Glu Trp Met Asp Ala Gly Thr Lys Arg Lys
    450                 455                 460

Ala Lys Glu Lys Ala Arg Ala Val Leu Ala Lys Val Gly Tyr Pro Glu
465                 470                 475                 480

Phe Ile Met Asn Asp Thr His Val Asn Glu Asp Leu Lys Ala Ile Lys
                485                 490                 495

Phe Ser Glu Ala Asp Tyr Phe Gly Asn Val Leu Gln Thr Arg Lys Tyr
            500                 505                 510

Leu Ala Gln Ser Asp Phe Phe Trp Leu Arg Lys Ala Val Pro Lys Thr
        515                 520                 525

Glu Trp Phe Thr Asn Pro Thr Thr Val Asn Ala Phe Tyr Ser Ala Ser
    530                 535                 540

Thr Asn Gln Ile Arg Phe Pro Ala Gly Glu Leu Gln Lys Pro Phe Phe
545                 550                 555                 560

Trp Gly Thr Glu Tyr Pro Arg Ser Leu Ser Tyr Gly Ala Ile Gly Val
                565                 570                 575

Ile Val Gly His Glu Phe Thr His Gly Phe Asp Asn Asn Gly Arg Lys
            580                 585                 590

Tyr Asp Lys Asn Gly Asn Leu Asp Pro Trp Trp Ser Thr Glu Ser Glu
        595                 600                 605

Glu Lys Phe Lys Glu Lys Thr Lys Cys Met Ile Asn Gln Tyr Ser Asn
    610                 615                 620
```

```
Tyr Tyr Trp Lys Lys Ala Gly Leu Asn Val Lys Gly Lys Arg Thr Leu
625                 630                 635                 640

Gly Glu Asn Ile Ala Asp Asn Gly Gly Leu Arg Glu Ala Phe Arg Ala
            645                 650                 655

Tyr Arg Lys Trp Ile Asn Asp Arg Arg Gln Gly Leu Glu Glu Pro Leu
            660                 665                 670

Leu Pro Gly Ile Thr Phe Thr Asn Asn Gln Leu Phe Phe Leu Ser Tyr
            675                 680                 685

Ala His Val Arg Cys Asn Ser Tyr Arg Pro Glu Ala Ala Arg Glu Gln
            690                 695                 700

Val Gln Ile Gly Ala His Ser Pro Pro Gln Phe Arg Val Asn Gly Ala
705                 710                 715                 720

Ile Ser Asn Ser Glu Glu Phe Gln Lys Ala Phe Asn Cys Pro Pro Asn
            725                 730                 735

Ser Thr Met Asn Arg Gly Met Asp Ser Cys Arg Leu Trp
            740                 745

<210> SEQ ID NO 4
<211> LENGTH: 718
<212> TYPE: PRT
<213> ORGANISM: Artificial Sequence
<220> FEATURE:
<223> OTHER INFORMATION: Soluble PHEX conjugate

<400> SEQUENCE: 4

Ser Gly Asp Asp Asp Asp Asp Asp Asp Asp Ser Gly Ser Leu
1               5                   10                  15

Gln Ala Lys Gln Glu Tyr Cys Leu Lys Pro Glu Cys Ile Glu Ala Ala
            20                  25                  30

Ala Ala Ile Leu Ser Lys Val Asn Leu Ser Val Asp Pro Cys Asp Asn
            35                  40                  45

Phe Phe Arg Phe Ala Cys Asp Gly Trp Ile Ser Asn Asn Pro Ile Pro
50                  55                  60

Glu Asp Met Pro Ser Tyr Gly Val Tyr Pro Trp Leu Arg His Asn Val
65                  70                  75                  80

Asp Leu Lys Leu Lys Glu Leu Leu Glu Lys Ser Ile Ser Arg Arg Arg
            85                  90                  95

Asp Thr Glu Ala Ile Gln Lys Ala Lys Ile Leu Tyr Ser Ser Cys Met
            100                 105                 110

Asn Glu Lys Ala Ile Glu Lys Ala Asp Ala Lys Pro Leu Leu His Ile
            115                 120                 125

Leu Arg His Ser Pro Phe Arg Trp Pro Val Leu Glu Ser Asn Ile Gly
            130                 135                 140

Pro Glu Gly Val Trp Ser Glu Arg Lys Phe Ser Leu Leu Gln Thr Leu
145                 150                 155                 160

Ala Thr Phe Arg Gly Gln Tyr Ser Asn Ser Val Phe Ile Arg Leu Tyr
            165                 170                 175

Val Ser Pro Asp Asp Lys Ala Ser Asn Glu His Ile Leu Lys Leu Asp
            180                 185                 190

Gln Ala Thr Leu Ser Leu Ala Val Arg Glu Asp Tyr Leu Asp Asn Ser
            195                 200                 205

Thr Glu Ala Lys Ser Tyr Arg Asp Ala Leu Tyr Lys Phe Met Val Asp
            210                 215                 220

Thr Ala Val Leu Leu Gly Ala Asn Ser Ser Arg Ala Glu His Asp Met
225                 230                 235                 240
```

-continued

```
Lys Ser Val Leu Arg Leu Glu Ile Lys Ile Ala Glu Ile Met Ile Pro
            245                 250                 255

His Glu Asn Arg Thr Ser Glu Ala Met Tyr Asn Lys Met Asn Ile Ser
        260                 265                 270

Glu Leu Ser Ala Met Ile Pro Gln Phe Asp Trp Leu Gly Tyr Ile Lys
    275                 280                 285

Lys Val Ile Asp Thr Arg Leu Tyr Pro His Leu Lys Asp Ile Ser Pro
290                 295                 300

Ser Glu Asn Val Val Arg Val Pro Gln Tyr Phe Lys Asp Leu Phe
305                 310                 315                 320

Arg Ile Leu Gly Ser Glu Arg Lys Lys Thr Ile Ala Asn Tyr Leu Val
                325                 330                 335

Trp Arg Met Val Tyr Ser Arg Ile Pro Asn Leu Ser Arg Arg Phe Gln
            340                 345                 350

Tyr Arg Trp Leu Glu Phe Ser Arg Val Ile Gln Gly Thr Thr Thr Leu
        355                 360                 365

Leu Pro Gln Trp Asp Lys Cys Val Asn Phe Ile Glu Ser Ala Leu Pro
    370                 375                 380

Tyr Val Gly Lys Met Phe Val Asp Val Tyr Phe Gln Glu Asp Lys
385                 390                 395                 400

Lys Glu Met Met Glu Glu Leu Val Glu Gly Val Arg Trp Ala Phe Ile
                405                 410                 415

Asp Met Leu Glu Lys Glu Asn Glu Trp Met Asp Ala Gly Thr Lys Arg
            420                 425                 430

Lys Ala Lys Glu Lys Ala Arg Ala Val Leu Ala Lys Val Gly Tyr Pro
        435                 440                 445

Glu Phe Ile Met Asn Asp Thr His Val Asn Glu Asp Leu Lys Ala Ile
    450                 455                 460

Lys Phe Ser Glu Ala Asp Tyr Phe Gly Asn Val Leu Gln Thr Arg Lys
465                 470                 475                 480

Tyr Leu Ala Gln Ser Asp Phe Phe Trp Leu Arg Lys Ala Val Pro Lys
                485                 490                 495

Thr Glu Trp Phe Thr Asn Pro Thr Thr Val Asn Ala Phe Tyr Ser Ala
            500                 505                 510

Ser Thr Asn Gln Ile Arg Phe Pro Ala Gly Glu Leu Gln Lys Pro Phe
        515                 520                 525

Phe Trp Gly Thr Glu Tyr Pro Arg Ser Leu Ser Tyr Gly Ala Ile Gly
    530                 535                 540

Val Ile Val Gly His Glu Phe Thr His Gly Phe Asp Asn Asn Gly Arg
545                 550                 555                 560

Lys Tyr Asp Lys Asn Gly Asn Leu Asp Pro Trp Trp Ser Thr Glu Ser
                565                 570                 575

Glu Glu Lys Phe Lys Glu Lys Thr Lys Cys Met Ile Asn Gln Tyr Ser
            580                 585                 590

Asn Tyr Tyr Trp Lys Lys Ala Gly Leu Asn Val Lys Gly Lys Arg Thr
        595                 600                 605

Leu Gly Glu Asn Ile Ala Asp Asn Gly Gly Leu Arg Glu Ala Phe Arg
    610                 615                 620

Ala Tyr Arg Lys Trp Ile Asn Asp Arg Arg Gln Gly Leu Glu Glu Pro
625                 630                 635                 640

Leu Leu Pro Gly Ile Thr Phe Thr Asn Asn Gln Leu Phe Phe Leu Ser
                645                 650                 655

Tyr Ala His Val Arg Cys Asn Ser Tyr Arg Pro Glu Ala Ala Arg Glu
```

Gln Val Gln Ile Gly Ala His Ser Pro Pro Gln Phe Arg Val Asn Gly
              675                 680                 685

Ala Ile Ser Asn Phe Glu Glu Phe Gln Lys Ala Phe Asn Cys Pro Pro
          690                 695                 700

Asn Ser Thr Met Asn Arg Gly Met Asp Ser Cys Arg Leu Trp
705                 710                 715

<210> SEQ ID NO 5
<211> LENGTH: 1524
<212> TYPE: DNA
<213> ORGANISM: Artificial Sequence
<220> FEATURE:
<223> OTHER INFORMATION: Encoding soluble alkaline phosphatase

<400> SEQUENCE: 5

| | | |
|---|---|---|
| ggatccacca tgatttcacc attcttagta ctggccattg caccctgcct tactaactcc | 60 |
| ttagtgccag agaaagagaa agaccccaag tactggcgag accaagcgca agagacactg | 120 |
| aaatatgccc tggagcttca gaagctcaac accaacgtgg ctaagaatgt catcatgttc | 180 |
| ctgggagatg ggatgggtgt ctccacagtg acggctgccc gcatcctcaa gggtcagctc | 240 |
| caccacaacc ctggggagga gaccaggctg gagatggaca agttcccctt cgtggccctc | 300 |
| tccaagacgt acaacaccaa tgcccaggtc cctgacagcg ccggcaccgc caccgcctac | 360 |
| ctgtgtgggg tgaaggccaa tgagggcacc gtggggtaa gcgcagccac tgagcgttcc | 420 |
| cggtgcaaca ccacccaggg gaacgaggtc acctccatcc tgcgctgggc caaggacgct | 480 |
| gggaaatctg tgggcattgt gaccaccacg agagtgaacc atgccacccc cagcgccgcc | 540 |
| tacgcccact cggctgaccg ggactggtac tcagacaacg agatgccccc tgaggccttg | 600 |
| agccagggct gtaaggacat cgcctaccag ctcatgcata acatcaggga cattgacgtg | 660 |
| atcatggggg gtggccggaa atacatgtac cccaagaata aaactgatgt ggagtatgag | 720 |
| agtgacgaga agccaggggg cacgaggctg gacggcctgg acctcgttga cacctggaag | 780 |
| agcttcaaac cgagatacaa gcactccac ttcatctgga accgcacgga actcctgacc | 840 |
| cttgaccccc acaatgtgga ctacctattg ggtctcttcg agccagggga catgcagtac | 900 |
| gagctgaaca ggaacaacgt gacggacccg tcactctccg agatggtggt ggtggccatc | 960 |
| cagatcctgc ggaagaaccc caaaggcttc ttcttgctgg tggaaggagg cagaattgac | 1020 |
| cacgggcacc atgaaggaaa agccaagcag gccctgcatg aggcggtgga gatggaccgg | 1080 |
| gccatcgggc aggcaggcag cttgacctcc tcggaagaca ctctgaccgt ggtcactgcg | 1140 |
| gaccattccc acgtcttcac atttggtgga tacaccccc gtggcaactc tatctttggt | 1200 |
| ctggcccca tgctgagtga cacagacaag aagcccttca ctgccatcct gtatggcaat | 1260 |
| gggcctggct acaaggtggt gggcggtgaa cgagagaatg tctccatggt ggactatgct | 1320 |
| cacaacaact accaggcgca gtctgctgtg ccctgcgcc acgagaccca cggcggggag | 1380 |
| gacgtggccg tcttctccaa gggccccatg gcgcacctgc tgcacggcgt ccacgagcag | 1440 |
| aactacgtcc cccacgtgat ggcgtatgca gcctgcatcg gggccaacct cggccactgt | 1500 |
| gctcctgcca gctcgtagtc taga | 1524 |

<210> SEQ ID NO 6
<211> LENGTH: 502
<212> TYPE: PRT
<213> ORGANISM: Artificial Sequence
<220> FEATURE:

<223> OTHER INFORMATION: Soluble alkaline phosphatase

<400> SEQUENCE: 6

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Glu Thr Leu Lys Tyr Ala Leu Glu Leu Gln Lys Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Ser Arg Cys Asn Thr Thr Gln Gly
130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Arg Asp Ile Asp Val Ile Met Gly Gly Gly Arg Lys
    210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg Tyr Lys His Ser His Phe Ile Trp Asn Arg
            260                 265                 270

Thr Glu Leu Leu Thr Leu Asp Pro His Asn Val Asp Tyr Leu Leu Gly
        275                 280                 285

Leu Phe Glu Pro Gly Asp Met Gln Tyr Glu Leu Asn Arg Asn Asn Val
    290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Arg Ala Ile Gly Gln Ala Gly Ser Leu Thr Ser Ser
        355                 360                 365

Glu Asp Thr Leu Thr Val Val Thr Ala Asp His Ser His Val Phe Thr
    370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
            405                 410                 415

Asn Gly Pro Gly Tyr Lys Val Val Gly Gly Glu Arg Glu Asn Val Ser
        420                 425                 430

Met Val Asp Tyr Ala His Asn Asn Tyr Gln Ala Gln Ser Ala Val Pro
        435                 440                 445

Leu Arg His Glu Thr His Gly Gly Glu Asp Val Ala Val Phe Ser Lys
        450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser
                500

<210> SEQ ID NO 7
<211> LENGTH: 1554
<212> TYPE: DNA
<213> ORGANISM: Artificial Sequence
<220> FEATURE:
<223> OTHER INFORMATION: Encoding soluble alkaline phosphatase conjugate

<400> SEQUENCE: 7
ggatccacca tgatttcacc attcttagta ctggccattg gcacctgcct tactaactcc      60
ttagtgccag agaaagagaa agaccccaag tactggcgag accaagcgca agagacactg    120
aaatatgccc tggagcttca gaagctcaac accaacgtgg ctaagaatgt catcatgttc    180
ctgggagatg ggatgggtgt ctccacagtg acggctgccc gcatcctcaa gggtcagctc    240
caccacaacc tggggagga gaccaggctg gagatggaca gttccccctt cgtggccctc    300
tccaagacgt acaacaccaa tgcccaggtc cctgacagcg ccggcaccgc caccgcctac    360
ctgtgtgggg tgaaggccaa tgagggcacc gtggggtaa cgcagccac tgagcgttcc    420 cggtgcaaca ccacccaggg gaacgaggtc acctccatcc tgcgctgggc caaggacgct    480
gggaaatctg tggcattgt gaccaccacg agagtgaacc atgccacccc cagcgccgcc    540
tacgcccact cggctgaccg ggactggtac tcagacaacg agatgccccc tgaggccttg    600
agccagggct gtaaggacat cgcctaccag ctcatgcata acatcaggga cattgacgtg    660
atcatggggg gtgccggaa atacatgtac cccaagaata aaactgatgt ggagtatgag    720
agtgacgaga agccaggggc acgaggctg acggcctgg acctcgttga cacctggaag    780
agcttcaaac cgagatacaa gcactccac ttcatctgga accgcacgga actcctgacc    840
cttgaccccc acaatgtgga ctacctattg ggtctcttcg agccagggga catgcagtac    900
gagctgaaca ggaacaacgt gacggacccg tcactctccg agatggtggt ggtggccatc    960
cagatcctgc ggaagaaccc caaaggcttc ttcttgctgg tggaaggagg cagaattgac   1020
cacgggcacc atgaaggaaa agccaagcag gccctgcatg aggcggtgga gatgaccgg   1080 gccatcgggc aggcaggcag cttgacctcc tcggaagaca ctctgaccgt ggtcactgcg   1140
gaccattccc acgtcttcac atttggtgga tacaccccccc gtggcaactc tatctttggt   1200 ctggcccca tgctgagtga cacagacaag aagcccttca ctgccatcct gtatggcaat   1260
gggcctggct acaaggtggt gggcggtgaa cgagagaatg tctccatggt ggactatgct   1320
cacaacaact accaggcgca gtctgctgtg ccctgcgcc acgagaccca cggcggggag   1380
gacgtggccg tcttctccaa gggccccatg gcgcacctgc tgcacggcgt ccacgagcag   1440

```
aactacgtcc cccacgtgat ggcgtatgca gcctgcatcg gggccaacct cggccactgt    1500
gctcctgcca gctcggatga cgacgatgat gacgatgatg acgactagtc taga          1554
```

<210> SEQ ID NO 8
<211> LENGTH: 512
<212> TYPE: PRT
<213> ORGANISM: Artificial Sequence
<220> FEATURE:
<223> OTHER INFORMATION: Soluble alkaline phosphatase conjugate

<400> SEQUENCE: 8

```
Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Glu Thr Leu Lys Tyr Ala Leu Glu Leu Gln Lys Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Ser Arg Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Arg Asp Ile Asp Val Ile Met Gly Gly Gly Arg Lys
    210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg Tyr Lys His Ser His Phe Ile Trp Asn Arg
            260                 265                 270

Thr Glu Leu Leu Thr Leu Asp Pro His Asn Val Asp Tyr Leu Leu Gly
        275                 280                 285

Leu Phe Glu Pro Gly Asp Met Gln Tyr Glu Leu Asn Arg Asn Asn Val
    290                 295                 300

Thr Asp Pro Ser Leu Ser Glu Met Val Val Val Ala Ile Gln Ile Leu
305                 310                 315                 320

Arg Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350
```

```
Val Glu Met Asp Arg Ala Ile Gly Gln Ala Gly Ser Leu Thr Ser Ser
        355                 360                 365
Glu Asp Thr Leu Thr Val Val Thr Ala Asp His Ser His Val Phe Thr
    370                 375                 380
Phe Gly Gly Tyr Thr Pro Arg Gly Asn Ser Ile Phe Gly Leu Ala Pro
385                 390                 395                 400
Met Leu Ser Asp Thr Asp Lys Lys Pro Phe Thr Ala Ile Leu Tyr Gly
                405                 410                 415
Asn Gly Pro Gly Tyr Lys Val Val Gly Gly Glu Arg Glu Asn Val Ser
            420                 425                 430
Met Val Asp Tyr Ala His Asn Asn Tyr Gln Ala Gln Ser Ala Val Pro
        435                 440                 445
Leu Arg His Glu Thr His Gly Gly Glu Asp Val Ala Val Phe Ser Lys
    450                 455                 460
Gly Pro Met Ala His Leu Leu His Gly Val His Glu Gln Asn Tyr Val
465                 470                 475                 480
Pro His Val Met Ala Tyr Ala Ala Cys Ile Gly Ala Asn Leu Gly His
                485                 490                 495
Cys Ala Pro Ala Ser Ser Asp Asp Asp Asp Asp Asp Asp Asp Asp Asp
            500                 505                 510
```

<210> SEQ ID NO 9
<211> LENGTH: 25
<212> TYPE: DNA
<213> ORGANISM: Artificial Sequence
<220> FEATURE:
<223> OTHER INFORMATION: Oligonucleotide

<400> SEQUENCE: 9
gatccgatga cgatgacgat gacgc         25

<210> SEQ ID NO 10
<211> LENGTH: 25
<212> TYPE: DNA
<213> ORGANISM: Artificial Sequence
<220> FEATURE:
<223> OTHER INFORMATION: Oligonucleotide

<400> SEQUENCE: 10
ggccgcgtca tcgtcatcgt catcg         25

<210> SEQ ID NO 11
<211> LENGTH: 37
<212> TYPE: DNA
<213> ORGANISM: Artificial Sequence
<220> FEATURE:
<223> OTHER INFORMATION: Oligonucleotide

<400> SEQUENCE: 11
gatccgatga cgatgacgat gacgatgacg atgacgc         37

<210> SEQ ID NO 12
<211> LENGTH: 37
<212> TYPE: DNA
<213> ORGANISM: Artificial Sequence
<220> FEATURE:
<223> OTHER INFORMATION: Oligonucleotide

<400> SEQUENCE: 12
ggccgcgtca tcgtcatcgt catcgtcatc gtcatcg         37

<210> SEQ ID NO 13
<211> LENGTH: 55
<212> TYPE: DNA
<213> ORGANISM: Artificial Sequence
<220> FEATURE:
<223> OTHER INFORMATION: Oligonucleotide

<400> SEQUENCE: 13
gatccgatga cgatgacgat gacgatgacg atgacgatga cgatgacgat gacgc    55

<210> SEQ ID NO 14
<211> LENGTH: 55
<212> TYPE: DNA
<213> ORGANISM: Artificial Sequence
<220> FEATURE:
<223> OTHER INFORMATION: Oligonucleotide

<400> SEQUENCE: 14
ggccgcgtca tcgtcatcgt catcgtcatc gtcatcgtca tcgtcatcgt catcg    55

<210> SEQ ID NO 15
<211> LENGTH: 61
<212> TYPE: DNA
<213> ORGANISM: Artificial Sequence
<220> FEATURE:
<223> OTHER INFORMATION: Oligonucleotide

<400> SEQUENCE: 15
gatccgatga cagtagtgag tcatctgaca gtggcagttc aagtgagagc gatggtgacg    60
c    61

<210> SEQ ID NO 16
<211> LENGTH: 61
<212> TYPE: DNA
<213> ORGANISM: Artificial Sequence
<220> FEATURE:
<223> OTHER INFORMATION: Oligonucleotide

<400> SEQUENCE: 16
ggccgcgtca ccatcgctct cacttgaact gccactgtca gatgactcac tactgtcatc    60
g    61

<210> SEQ ID NO 17
<211> LENGTH: 52
<212> TYPE: DNA
<213> ORGANISM: Artificial Sequence
<220> FEATURE:
<223> OTHER INFORMATION: Oligonucleotide

<400> SEQUENCE: 17
gatccgattc atctgaagag aaattttgc gtagaattgg aagattcggt gc    52

<210> SEQ ID NO 18
<211> LENGTH: 52
<212> TYPE: DNA
<213> ORGANISM: Artificial Sequence
<220> FEATURE:
<223> OTHER INFORMATION: Oligonucleotide

<400> SEQUENCE: 18
ggccgcaccg aatcttccaa ttctacgcaa aaatttctct tcagatgaat cg    52

<210> SEQ ID NO 19
<211> LENGTH: 58

<212> TYPE: DNA
<213> ORGANISM: Artificial Sequence
<220> FEATURE:
<223> OTHER INFORMATION: Oligonucleotide

<400> SEQUENCE: 19
gatcctgtta tgaatcacat gaaagcatgg aatcttatga acttaatccc ttcattgc    58

<210> SEQ ID NO 20
<211> LENGTH: 58
<212> TYPE: DNA
<213> ORGANISM: Artificial Sequence
<220> FEATURE:
<223> OTHER INFORMATION: Oligonucleotide

<400> SEQUENCE: 20
ggccgcaatg aagggattaa gttcataaga ttccatgctt tcatgtgatt cataacag    58

<210> SEQ ID NO 21
<211> LENGTH: 46
<212> TYPE: DNA
<213> ORGANISM: Artificial Sequence
<220> FEATURE:
<223> OTHER INFORMATION: Oligonucleotide

<400> SEQUENCE: 21
gatcccagaa tgctgtgtcc tctgaagaaa ccaatgactt taaagc    46

<210> SEQ ID NO 22
<211> LENGTH: 46
<212> TYPE: DNA
<213> ORGANISM: Artificial Sequence
<220> FEATURE:
<223> OTHER INFORMATION: Oligonucleotide

<400> SEQUENCE: 22
ggccgcttta aagtcattgg tttcttcaga ggacacagca ttctgg    46

<210> SEQ ID NO 23
<211> LENGTH: 64
<212> TYPE: DNA
<213> ORGANISM: Artificial Sequence
<220> FEATURE:
<223> OTHER INFORMATION: Oligonucleotide

<400> SEQUENCE: 23
gatccggcag tagtgactca tccgaagaaa tggagatga cagttcagaa gaggaggagg    60
aagc    64

<210> SEQ ID NO 24
<211> LENGTH: 64
<212> TYPE: DNA
<213> ORGANISM: Artificial Sequence
<220> FEATURE:
<223> OTHER INFORMATION: Oligonucleotide

<400> SEQUENCE: 24
ggccgcttcc tcctcctctt ctgaactgtc atctccattt tcttcggatg agtcactact    60
gccg    64

<210> SEQ ID NO 25
<211> LENGTH: 61
<212> TYPE: DNA
<213> ORGANISM: Artificial Sequence
<220> FEATURE:

```
<223> OTHER INFORMATION: Oligonucleotide

<400> SEQUENCE: 25
gatcccgcaa aggattctac aagagaaagc agtgcaaacc ttcccgtggc cgcaagcgtg    60
c                                                                   61

<210> SEQ ID NO 26
<211> LENGTH: 61
<212> TYPE: DNA
<213> ORGANISM: Artificial Sequence
<220> FEATURE:
<223> OTHER INFORMATION: Oligonucleotide

<400> SEQUENCE: 26
ggccgcacgc ttgcggccac gggaaggttt gcactgcttt ctcttgtaga atcctttgcg    60
g                                                                   61

<210> SEQ ID NO 27
<211> LENGTH: 32
<212> TYPE: DNA
<213> ORGANISM: Artificial Sequence
<220> FEATURE:
<223> OTHER INFORMATION: Oligonucleotide

<400> SEQUENCE: 27
agtcgggatc cggaacaagc agcgtgttct ac                                  32

<210> SEQ ID NO 28
<211> LENGTH: 39
<212> TYPE: DNA
<213> ORGANISM: Artificial Sequence
<220> FEATURE:
<223> OTHER INFORMATION: Oligonucleotide

<400> SEQUENCE: 28
agatcgcggc cgctcaattg tgcacggtgt gattaaagg                           39

<210> SEQ ID NO 29
<211> LENGTH: 36
<212> TYPE: DNA
<213> ORGANISM: Artificial Sequence
<220> FEATURE:
<223> OTHER INFORMATION: Oligonucleotide

<400> SEQUENCE: 29
ccggagatga cgatgacgat gacgatgacg atgact                              36

<210> SEQ ID NO 30
<211> LENGTH: 36
<212> TYPE: DNA
<213> ORGANISM: Artificial Sequence
<220> FEATURE:
<223> OTHER INFORMATION: Oligonucleotide

<400> SEQUENCE: 30
tctactgcta ctgctactgc tactgctact gaggcc                              36

<210> SEQ ID NO 31
<211> LENGTH: 18
<212> TYPE: PRT
<213> ORGANISM: Artificial Sequence
<220> FEATURE:
<223> OTHER INFORMATION: Human fragment of MEPE

<400> SEQUENCE: 31
```

Asp Asp Ser Ser Glu Ser Ser Asp Ser Gly Ser Ser Ser Glu Ser Asp
1               5                   10                  15

Gly Asp

<210> SEQ ID NO 32
<211> LENGTH: 15
<212> TYPE: PRT
<213> ORGANISM: Artificial Sequence
<220> FEATURE:
<223> OTHER INFORMATION: Human fragment of Statherin

<400> SEQUENCE: 32

Asp Ser Ser Glu Glu Lys Phe Leu Arg Arg Ile Gly Arg Phe Gly
1               5                   10                  15

<210> SEQ ID NO 33
<211> LENGTH: 17
<212> TYPE: PRT
<213> ORGANISM: Artificial Sequence
<220> FEATURE:
<223> OTHER INFORMATION: Human fragment of MGP

<400> SEQUENCE: 33

Cys Tyr Glu Ser His Glu Ser Met Glu Ser Tyr Glu Leu Asn Pro Phe
1               5                   10                  15

Ile

<210> SEQ ID NO 34
<211> LENGTH: 13
<212> TYPE: PRT
<213> ORGANISM: Artificial Sequence
<220> FEATURE:
<223> OTHER INFORMATION: Human fragment of OPN

<400> SEQUENCE: 34

Gln Asn Ala Val Ser Ser Glu Glu Thr Asn Asp Phe Lys
1               5                   10

<210> SEQ ID NO 35
<211> LENGTH: 18
<212> TYPE: PRT
<213> ORGANISM: Artificial Sequence
<220> FEATURE:
<223> OTHER INFORMATION: Human fragment of BSP2

<400> SEQUENCE: 35

Gly Ser Ser Asp Ser Ser Glu Glu Asn Gly Asp Asp Ser Ser Glu Glu
1               5                   10                  15

Glu Glu

<210> SEQ ID NO 36
<211> LENGTH: 18
<212> TYPE: PRT
<213> ORGANISM: Artificial Sequence
<220> FEATURE:
<223> OTHER INFORMATION: Human fragment of IGFBP5

<400> SEQUENCE: 36

Arg Lys Gly Phe Tyr Lys Arg Lys Gln Cys Lys Pro Ser Arg Gly Arg
1               5                   10                  15

Lys Arg

<210> SEQ ID NO 37

-continued

```
<211> LENGTH: 151
<212> TYPE: PRT
<213> ORGANISM: Artificial Sequence
<220> FEATURE:
<223> OTHER INFORMATION: Collagen binding domain of staphilococcus
      aureus collagen adhesin M81736

<400> SEQUENCE: 37

Gly Thr Ser Ser Val Phe Tyr Tyr Lys Thr Gly Asp Met Leu Pro Glu
1               5                   10                  15

Asp Thr Thr His Val Arg Trp Phe Leu Asn Ile Asn Asn Glu Lys Ser
            20                  25                  30

Tyr Val Ser Lys Asp Ile Thr Ile Lys Asp Gln Ile Gln Gly Gly Gln
        35                  40                  45

Gln Leu Asp Leu Ser Thr Leu Asn Ile Asn Val Thr Gly Thr His Ser
    50                  55                  60

Asn Tyr Tyr Ser Gly Gln Ser Ala Ile Thr Asp Phe Glu Lys Ala Phe
65              70                  75                  80

Pro Gly Ser Lys Ile Thr Val Asp Asn Thr Lys Asn Thr Ile Asp Val
            85                  90                  95

Thr Ile Pro Gln Gly Tyr Gly Ser Tyr Asn Ser Phe Ser Ile Asn Tyr
        100                 105                 110

Lys Thr Lys Ile Thr Asn Glu Gln Gln Lys Glu Phe Val Asn Asn Ser
    115                 120                 125

Gln Ala Trp Tyr Gln Glu His Gly Lys Glu Glu Val Asn Gly Lys Ser
130                 135                 140

Phe Asn His Thr Val His Asn
145                 150

<210> SEQ ID NO 38
<211> LENGTH: 41
<212> TYPE: DNA
<213> ORGANISM: Artificial Sequence
<220> FEATURE:
<223> OTHER INFORMATION: Oligonucleotide primer

<400> SEQUENCE: 38
cagtcaaggt ctcttatccg gaagtctcca agctaaacag g                        41

<210> SEQ ID NO 39
<211> LENGTH: 41
<212> TYPE: DNA
<213> ORGANISM: Artificial Sequence
<220> FEATURE:
<223> OTHER INFORMATION: Oligonucleotide primer

<400> SEQUENCE: 39
ctgtttagct tggagacttc cggataagag accttgactg g                        41

<210> SEQ ID NO 40
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 40
gataaagcag gtcttggggt gcacc                                          25

<210> SEQ ID NO 41
<211> LENGTH: 25
<212> TYPE: DNA
```

```
<213> ORGANISM: Artificial Sequence
<220> FEATURE:
<223> OTHER INFORMATION: Oligonucleotide primer

<400> SEQUENCE: 41
gttggcatct gtcacgggct tgtgg                                          25

<210> SEQ ID NO 42
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 42
tggatccacc atgatttcac cattcttagt ac                                  32

<210> SEQ ID NO 43
<211> LENGTH: 35
<212> TYPE: DNA
<213> ORGANISM: Artificial Sequence
<220> FEATURE:
<223> OTHER INFORMATION: Oligonucleotide primer

<400> SEQUENCE: 43
ttctagacta cgagctggca ggagcacagt ggccg                               35

<210> SEQ ID NO 44
<211> LENGTH: 65
<212> TYPE: DNA
<213> ORGANISM: Artificial Sequence
<220> FEATURE:
<223> OTHER INFORMATION: Oligonucleotide primer

<400> SEQUENCE: 44
ttctagacta gtcgtcatca tcgtcatcat cgtcgtcatc cgagctggca ggagcacagt    60
ggccg                                                                65

<210> SEQ ID NO 45
<211> LENGTH: 5
<212> TYPE: PRT
<213> ORGANISM: Artificial Sequence
<220> FEATURE:
<223> OTHER INFORMATION: Fragment surrounding cleavage site

<400> SEQUENCE: 45

Ser Leu Gln Ala Lys
1               5

<210> SEQ ID NO 46
<211> LENGTH: 11
<212> TYPE: PRT
<213> ORGANISM: Artificial Sequence
<220> FEATURE:
<223> OTHER INFORMATION: Fragment surrounding cleavage site

<400> SEQUENCE: 46

Thr Ser Asp Lys Thr His Ser Leu Gln Ala Lys
1               5                   10

<210> SEQ ID NO 47
<211> LENGTH: 7
<212> TYPE: PRT
<213> ORGANISM: Artificial Sequence
<220> FEATURE:
<223> OTHER INFORMATION: Fragment surrounding cleavage site
```

```
<400> SEQUENCE: 47

Ser Val Ser Leu Gln Ala Lys
1               5

<210> SEQ ID NO 48
<211> LENGTH: 19
<212> TYPE: PRT
<213> ORGANISM: Artificial Sequence
<220> FEATURE:
<223> OTHER INFORMATION: Fragment surrounding cleavage site

<400> SEQUENCE: 48

Ser Gly Asp Asp Asp Asp Asp Asp Asp Asp Asp Ser Gly Ser Leu
1               5                   10                  15

Gln Ala Lys

<210> SEQ ID NO 49
<211> LENGTH: 14
<212> TYPE: PRT
<213> ORGANISM: Artificial Sequence
<220> FEATURE:
<223> OTHER INFORMATION: Fragment surrounding cleavage site

<400> SEQUENCE: 49

Ser Asp Asp Asp Asp Asp Asp Tyr Val Ser Leu Gln Ala Lys
1               5                   10

<210> SEQ ID NO 50
<211> LENGTH: 8
<212> TYPE: PRT
<213> ORGANISM: Artificial Sequence
<220> FEATURE:
<223> OTHER INFORMATION: Fragment surrounding cleavage site

<400> SEQUENCE: 50

Arg Thr Val Val Lys Arg Ser Val
1               5
```

BONE DELIVERY CONJUGATES AND METHOD OF USING SAME TO TARGET PROTEINS TO BONE

CROSS REFERENCE TO RELATED APPLICATIONS

This application is a continuation of U.S. application Ser. No. 11/111,664, filed Apr. 21, 2005, which claims the benefit of the filing dates of U.S. Provisional Application Nos. 60/563,828 filed Apr. 21, 2004, 60/590,347 filed Jul. 23, 2004, and 60/614,984 filed Oct. 4, 2004, each of which is incorporated herein by reference.

REFERENCE TO A SEQUENCE LISTING

A Sequence Listing is provided in this patent document as a .txt file entitled, "50694_002005_Amended_Sequence_Listing_ST25.txt", created May 14, 2010 (size 45.3 kB). The content of this file is hereby incorporated by reference.

FIELD OF THE INVENTION

The present invention relates to bone delivery conjugates and method of using same to target proteins to bone. More specifically, the present invention relates to bone delivery compositions comprising peptide motifs, engineered within the structure of a protein through recombinant DNA technology to promote binding to bone matrix.

BACKGROUND OF THE INVENTION

Technological advances in molecular biology, recombinant protein production and large scale protein purification have allowed the production of large amounts of proteins now used as biopharmaceuticals. For example, monoclonal antibodies and soluble forms of the TNF-a receptor have been used in the treatment of autoimmune diseases such as Crohn's disease or severe forms of psoriasis (1). Another example of use of recombinant protein is enzyme replacement therapy (ERT). ERT has been used to treat lysosomal storage diseases. This group of genetic disorders is characterized by the loss of function of lysosome enzymes resulting in severe somatic, and sometimes neuronal, pathologies. In ERT for these diseases, the patients are infused with large doses of normal enzymes. These infused enzymes are then internalized from circulation via cell surface receptors (mannose-6 phosphate receptor) and enter the endocytic pathway on their way to their site of action, the lysosome. Not all attempts to treat genetic disorders through ERT have been successful.

Hypophosphatasia is a rare, heritable type of rickets or osteomalacia that occurs with an incidence of 1 per 100,000 births for the more severe form of the disease. Milder forms are more prevalent. In this inborn metabolism defect, mutations inactivate the gene that encodes the tissue-nonspecific isoenzyme of alkaline phosphatase. It is characterized biochemically by subnormal alkaline phosphatase activity in serum. Alkaline phosphatase deficiency in osteoblasts and chondrocytes impairs skeletal mineralization, leading to rickets or osteomalacia.

There is a very broad range of expressivity of hypophosphatasia, spanning from a perinatal form often causing stillbirth from an unmineralized skeleton, to a milder form featuring only premature loss of teeth. Severely affected infants and children inherit hypophosphatasia as an autosomal recessive trait. There are four main forms of the disease: perinatal, infantile, childhood and adult. Perinatal hypophosphatasia manifests during gestation and most affected newborns survive only briefly. Infantile hypophosphatasia becomes clinically apparent before 6 months of age. About 50% of patients die within a year. Childhood hypophosphatasia varies greatly in severity but most of these patients will suffer from skeletal symptoms throughout their life. Adult hypophosphatasia appears during middle age, with symptoms such as painful recurrent stress fractures having poor healing.

Osteoblasts and chondrocytes are normally rich in tissue-nonspecific alkaline phosphatase where it is attached to the cell surface. In hypophosphatasia, the lack of alkaline phosphatase activity results in the extracellular accumulation of three phosphorus-compounds believed to be substrates of the enzyme: phosphoethanolamine (PEA), inorganic pyrophosphate (PPi) and pyridoxal 5'-phosphate (PLP). PPi is an inhibitor of hydroxyapatite crystal growth, and PPi build-up in the disease accounts for the impaired skeletal mineralization. Consequently, providing active enzyme to patients suffering from hypophosphatasia will decrease extracellular PPi levels and improve skeletal mineralization.

Currently, there is no established medical therapy for hypophosphatasia. Trials of enzyme replacement using intravenous infusions of alkaline phosphatase have failed. It appears that alkaline phosphatase activity must be increased not in circulation but in the skeleton itself. This hypothesis was confirmed recently by bone marrow transplantation. Unfortunately, the benefits of the transplantation lasted only for a short period of time due to poor engraftment.

There is a therefore a need to provide enzyme replacement therapy approach to provide active enzyme to the skeleton of patients suffering from hypophosphatasia.

Bone-targeted proteins could be useful not only for the treatment or prevention of hypophosphatasia (loss of function of alkaline phosphatase) but also for the treatment or prevention of other genetic diseases characterized by defective enzymatic activity involved in bone metabolism, such as X-linked hypophosphatemic rickets (XLH) (loss of function of phosphate regulating gene with homology to endopeptidases on the X chromosome (PHEX)).

XLH is the most prevalent of the familial hypophosphatemias (OMIM 307800, 307810). It is characterized by reduced phosphate reuptake in the kidney, hypophosphatemia, normocalcemia, normal to low plasma 1,25-dihydroxyvitamin D3 (1,25(OH)$_2$D, calcitriol) levels, normal parathyroid gland function and elevated plasma alkaline phosphatase activity. These changes are associated with growth retardation, lower extremity deformity, radiologic and histomorphometric evidence of rickets and osteomalacia. This disease appears to result from combined renal defects in tubular phosphate reabsorption and vitamin D metabolism, as well as a functional disorder in bone and teeth. XLH results from inactivating mutations in the PHEX gene, a member of the zinc metallopeptidase family of type II integral membrane glycoproteins. These mutations prevent the expression of a functional PHEX enzyme at the cell surface of osteoblasts. As of now, treatment of XLH patients is restricted to supplementation with oral inorganic phosphate (Pi) supplements in four or five divided doses per day, and co-administration of 1,25(OH)$_2$D to compensate for the inappropriate synthesis of 1,25(OH)$_2$D. Such high doses of phosphate frequently cause gastrointestinal intolerances, particularly diarrhea, leading to patient non-compliance. On the one hand, the phosphate load carries the risk of provoking secondary hyperparathyroidism (which may be severe enough to necessitate parathyroidectomy) while on the other hand, administration of excess 1,25(OH)$_2$D may lead to hypercalciuria, hypercalcemia and nephrocalcinosis.

Useful ERT for XLH would therefore seek to replace the defective PHEX enzyme in XLH patients with a functional enzyme obtained through recombinant DNA technology. As the normal PHEX enzyme is anchored in osteoblast plasma membrane by a hydrophobic peptide, the natural form of PHEX cannot be produced and purified in sufficient quantities to be used in a pharmaceutical preparation. To circumvent the problem, a soluble form of recombinant PHEX (or sPHEX) was engineered and produced in cell cultures, purified and formulated for intravenous (IV) administration (WO 00/50580). sPHEX was then injected in Hyp mice, a mouse model for XLH, as described in co-pending U.S. application Ser. No. 10/362,259. Improvement of several bone related serum parameter were observed including a reduction of the abnormally high levels of serum alkaline phosphatase. Although these experiments were successful, it was believed that the efficacy of therapeutic sPHEX might be enhanced if the recombinant protein was modified so as to promote its binding to bone minerals.

There is therefore a need for means to successfully target proteins to bone matrix.

Biphosphonates are known to present high affinity binding to hydroxyapatite (HA), and has been used to target small molecules (4) and proteins (5) to bones. However this strategy requires chemical modifications of the purified proteins, and presents several disadvantages including possible interference with protein activity and additional purification steps.

Another strategy to target small molecules to bone has been to conjugate these entities to acidic peptides such as poly-Asp (6). This strategy was developed after the observation that several proteins synthesized by osteoblasts, the bone forming cells, bind to bone matrix through sequences particularly rich in acidic amino acid residues (Asp and Glu). This is the case of osteopontin (7) and bone sialoprotein, two noncollagenous proteins. Hence acidic peptides ($E_{2-10}$ and $D_{2-10}$) were used to target small molecules (i.e. methotrexate, FITC, Fmoc, biotin, estradiol) to hydroxyapatite in vitro. Acidic peptides ($E_6$ and $D_{6-10}$) were used to target small molecules (i.e. FITC, Fmoc, estradiol) to hydroxyapatite in vivo. Finally, $E_6$ was shown to confer to BSA, hemoglobin and IgG the ability to bind hydroxyapatite in vitro. In all the above cases, linking of the acidic sequence was performed chemically.

The present invention seeks to meet these needs and other needs.

The present description refers to a number of documents, the content of which is herein incorporated by reference in their entirety.

SUMMARY OF THE INVENTION

The present invention shows that large and complex molecules such as proteins can be fused with acidic peptides to successfully target bone in vivo.

According to a specific embodiment of the present invention there is provided a bone delivery conjugate having a structure selected from the group consisting of: A) X-Dn-Y-protein-Z; and B) Z-protein-Y-Dn-X, wherein X is absent or is an amino acid sequence of at least one amino acid; Y is absent or is an amino acid sequence of at least one amino acid; Z is absent or is an amino acid sequence of at least one amino acid; and Dn is a poly aspartate wherein n=10 to 16. In another specific embodiment of the present invention, the protein in the bone delivery conjugate is a soluble phosphate regulating gene with homology to endopeptidases on the X chromosome (sPHEX). In another specific embodiment of the present invention, the structure of the conjugate is: X-Dn-Y-sPHEX-Z. In another specific embodiment of the present invention, the sPHEX has a sequence selected from the group consisting of amino acids 46 to 749 of FIG. 10; 47 to 749 of FIG. 10; 48 to 749 of FIG. 10; 49 to 749 of FIG. 10; 50 to 749 of FIG. 10; 51 to 749 of FIG. 10; 52 to 749 of FIG. 10; 53 to 749 of FIG. 10; and 54 to 749 of FIG. 10. In a specific embodiment of these bone delivery conjugates, n is 10. In another specific embodiment of this bone delivery conjugate, n is 11. In another specific embodiment of this bone delivery conjugate, n is 12. In another specific embodiment of this bone delivery conjugate, n is 13. In another specific embodiment of this bone delivery conjugate, n is 14. In another specific embodiment of this bone delivery conjugate, n is 15. In another specific embodiment of this bone delivery conjugate, n is 16. In a more specific embodiment of the present invention, the sPHEX consists of the sequence of amino acids 46 to 749 of FIG. 10 and n=10.

In another specific embodiment of the present invention, the protein in the conjugate is a soluble alkaline phosphatase (sALP). In another specific embodiment, the structure of the conjugate is: Z-sALP-X-Dn-Y. In another specific embodiment, sALP is encoded by the sequence as set forth in FIG. 16A. In another specific embodiment, sALP has the sequence as set forth in FIG. 16B. In a specific embodiment of these bone delivery conjugates, n is 10. In another specific embodiment of this bone delivery conjugate, n is 11. In another specific embodiment of this bone delivery conjugate, n is 12. In another specific embodiment of this bone delivery conjugate, n is 13. In another specific embodiment of this bone delivery conjugate, n is 14. In another specific embodiment of this bone delivery conjugate, n is 15. In another specific embodiment of this bone delivery conjugate, n is 16. In a more specific embodiment, n=10.

There is also provided an isolated nucleic acid molecule comprising a polynucleotide sequence selected from the group consisting of: a polynucleotide encoding a polypeptide comprising an amino acid sequence as set forth in FIG. 8; a polynucleotide encoding a polypeptide comprising an amino acid sequence as set forth in FIG. 11; a polynucleotide comprising the nucleotide sequence as set forth in FIG. 7; a nucleotide sequence completely complementary to any of the nucleotide sequences in (a), (b) or (c); and a nucleotide sequence which hybridizes under high stringency conditions to any of the nucleotide sequences in (a), (b), (c) or (d), wherein the high stringency conditions comprise: pre-hybridization and hybridization in 6×SSC, 5×Denhardt's reagent, 0.5% SDS and 100 mg/ml of denatured fragmented salmon sperm DNA at 68° C.; and washes in 2×SSC and 0.5% SDS at room temperature for 10 min; in 2×SSC and 0.1% SDS at room temperature for 10 min; and in 0.1×SSC and 0.5% SDS at 65° C. three times for 5 minutes.

There is also provided a recombinant vector comprising said sequence. There is also provided a recombinant host cell comprising said vector.

There is also provided an isolated nucleic acid molecule comprising a polynucleotide sequence selected from the group consisting of: a polynucleotide comprising the nucleotide sequence as set forth in FIG. 17A; a polynucleotide encoding a polypeptide comprising an amino acid sequence as set forth in FIG. 17B; a nucleotide sequence completely complementary to any of the nucleotide sequences in (a) or (b); and a nucleotide sequence which hybridizes under high stringency conditions to any of the nucleotide sequences in (a), (b) or (c), wherein the high stringency conditions comprise: pre-hybridization and hybridization in 6×SSC, 5×Denhardt's reagent, 0.5% SDS and 100 mg/ml of denatured fragmented salmon sperm DNA at 68° C.; and washes in 2×SSC and 0.5% SDS at room temperature for 10 min; in 2×SSC and 0.1% SDS at room temperature for 10 min; and in 0.1×SSC and 0.5% SDS at 65° C. three times for 5 minutes.

There is also provided an isolated nucleic acid molecule encoding a functional soluble PHEX comprising a polynucleotide sequence selected from the group consisting of: a polynucleotide encoding a sPHEX comprising amino acids 54 to 749 as set forth in FIG. 10; a polynucleotide encoding a sPHEX comprising amino acids 53 to 749 as set forth in FIG. 10; a polynucleotide encoding a sPHEX comprising amino acids 52 to 749 as set forth in FIG. 10; a polynucleotide encoding a sPHEX comprising amino acids 51 to 749 as set forth in FIG. 10; a polynucleotide encoding a sPHEX comprising amino acids 50 to 749 as set forth in FIG. 10; a polynucleotide encoding a sPHEX comprising amino acids 49 to 749 as set forth in FIG. 10; a polynucleotide encoding a sPHEX comprising amino acids 48 to 749 as set forth in FIG. 10; a polynucleotide encoding a sPHEX comprising amino acids 47 to 749 as set forth in FIG. 10; a polynucleotide encoding a sPHEX comprising amino acids 46 to 749 as set forth in FIG. 10; a nucleotide sequence completely complementary to any of the nucleotide sequences in (a) to (i): and a nucleotide sequence which hybridizes under high stringency conditions to any of the nucleotide sequences in (a) to (j), wherein the high stringency conditions comprise: pre-hybridization and hybridization in 6×SSC, 5×Denhardt's reagent, 0.5% SDS and 100 mg/ml of denatured fragmented salmon sperm DNA at 68° C.; and washes in 2×SSC and 0.5% SDS at room temperature for 10 min; in 2×SSC and 0.1% SDS at room temperature for 10 min; and in 0.1×SSC and 0.5% SDS at 65° C. three times for 5 minutes. In another embodiment, the isolated nucleic acid molecule further comprises at its 5' end, a polynucleotide encoding a poly-aspartate selected from the group consisting of $D_{10}$ to $D_{16}$.

There is also provided an isolated sPHEX polypeptide comprising a sequence selected from the group consisting of: amino acids 54 to 749 as set forth in FIG. 10; amino acids 53 to 749 as set for in FIG. 10; amino acids 52 to 749 as set for in FIG. 10; amino acids 51 to 749 as set for in FIG. 10; amino acids 50 to 749 as set for in FIG. 10; amino acids 49 to 749 as set for in FIG. 10; amino acids 48 to 749 as set for in FIG. 10; amino acids 47 to 749 as set for in FIG. 10; and amino acids 46 to 749 as set for in FIG. 10.

There is also provided a bone delivery composition comprising a bone delivery conjugate of the present invention, and a pharmaceutically acceptable carrier.

There is also provided a method of delivering a protein to bone tissue of a mammal comprising administering to said mammal an effective amount of a bone delivery conjugate as recited of the present invention.

There is also provided a method of delivering sPHEX to bone tissue of a mammal comprising administering to said mammal an effective amount of a bone delivery conjugate of the present invention.

There is also provided a method of delivering ALP to bone tissue of a mammal in need thereof comprising administering to said mammal an effective amount of a bone delivery conjugate of the present invention.

There is also provided a method of treating a condition or disease related to a bone defect characterized by a lack of or an insufficient amount of functional phosphate regulating gene with homology to endopeptidases on the X chromosome (PHEX) comprising administering to a mammal in need thereof a conjugate of the present invention, said conjugate being in a pharmaceutically acceptable carrier. In specific embodiments, the condition or disease is X-linked hypophosphatemic rickets (XLH).

There is also provided a method of treating a condition or disease related to a bone defect characterized by a lack of or an insufficient amount of functional alkaline phosphatase comprising administering to a mammal in need thereof a conjugate of the present invention, said conjugate being in a pharmaceutically acceptable carrier. In specific embodiments, the condition or disease is hypophosphatasia.

There is also provided a method of screening peptides for use in a bone delivery protein-peptide conjugate comprising the steps of: fusing a candidate peptide to a reporter protein to form a protein-peptide conjugate; contacting the conjugate with bone tissue or mineral phase of bone; and wherein the candidate peptide is selected when the presence of the reporter protein on bone tissue or mineral phase of bone is higher when it is conjugated with the candidate peptide than when it is not.

According to a specific embodiment of the present invention there is provided a bone delivery conjugate of a protein fused to a peptide selected from the group consisting of deca-aspartate ($D_{10}$) to hexadeca-aspartate ($D_{16}$).

In specific embodiments of conjugates of the present invention, the sPHEX is fused at its N-terminal to $D_{10}$. In another specific embodiment, the sPHEX is fused at its N-terminal to $D_{11}$. In another specific embodiment, the sPHEX is fused at its N-terminal to $D_{12}$. In another specific embodiment, the sPHEX is fused at its N-terminal to $D_{13}$. In another specific embodiment, the sPHEX is fused at its N-terminal to $D_{14}$. In another specific embodiment, the sPHEX is fused at its N-terminal to $D_{15}$. In another specific embodiment, the sPHEX is fused at its N-terminal to $D_{16}$.

According to specific embodiments of conjugates of the present invention, the sALP is fused at its C-terminal to $D_{10}$. In another specific embodiment, the sALP is fused at its C-terminal to $D_{11}$. In another specific embodiment, the sALP is fused at its C-terminal to $D_{12}$. In another specific embodiment, the sALP is fused at its C-terminal to $D_{13}$. In another specific embodiment, the sALP is fused at its C-terminal to $D_{14}$. In another specific embodiment, the sALP is fused at its C-terminal to $D_{15}$. In another specific embodiment, the sALP is fused at its C-terminal to $D_{16}$.

It is understood that any functional soluble protein may be used in the conjugate of the present invention. Although results for conjugates comprising one specific sPHEX or sALP of the present invention are presented herein, it is understood that any other functional sPHEX or sALP may be so used.

sPHEX

As used herein sPHEX means any soluble biologically active fragment of PHEX or mutein thereof. Those of skill in the art may prepare expression constructs other than those expressly described herein for optimal production of sPHEX in suitable cell lines transfected therewith. Moreover, skilled artisans may design fragments of cDNA encoding soluble biologically active fragments and muteins of the naturally occurring PHEX which possess the same or similar biological activity to the naturally occurring full-length enzyme.

To create a recombinant source for sPHEX, a large series of expression vectors may be constructed and tested for expression of a PHEX cDNA. Based on transient transfection experiments, as well as stable transfections, an expression construct may be identified that provides a particularly high level of expression.

Without being so limited, any sPHEX comprising at least a native PHEX ectodomain portion starting with the cysteine at position 54 of the sequence presented at FIG. 10 is encompassed by the present invention.

The conjugates according to specific embodiments of the present invention thus are any sPHEX comprising this 54-749 fragment of the native PHEX, preferably the 53-749 native fragment, more preferably the native 52-749 fragment, more preferably the native 51-749 fragment, more preferably the 50-749 native fragment, more preferably the 49-749 native fragment, more preferably the 48-749 native fragment, more preferably the 47-749 native fragment, and more preferably the 46-749 native fragment, along with a poly-aspartate selected from the group consisting of $D_{10}$ to $D_{15}$ fused immediately upstream of this fragment.

The conjugate may further optionally comprise one or more additional amino acids 1) upstream from the poly-aspartate; and/or 2) between the poly-aspartate and the native fragment or functional equivalent. These amino acids may be any amino acid. According to specific embodiments, they may be selected independently from the group consisting of any amino acid except for cysteine, proline and tryptophan namely those amino acids known to induce disulfide bond formation or changes in conformation.

These amino acids may be present in the conjugate when for instance the cloning strategy used to produce it introduces them in these locations.

According to specific cloning strategies, amino acids located upstream of the poly-aspartate in the recombinant cleavable PHEX can be selected according to known parameters so as to provide an adequate substrate for specific enzymes of the secretory pathway (e.g. furin or signal peptidase) of the host cell that will be used to cleave the produced recombinant cleavable PHEXs into a secreted bone targeting sPHEX. The likelihood of a designed sequence being cleaved by the signal peptidase of the host cell can be predicted by an appropriate computer algorithm such as that described in Bendtsen et al. (J Mol Biol. 2004 Jul. 16; 340(4):783-95) and available on the Web which takes into account parameters including the following: the amino acids at position -3 and -1 from the cleavage site by the signal peptidase desirably have small and non charged side chains. Preferably, at position -1: Ala, Ser, Gly, Cys, Thr and occasionally Gln, Pro, and Leu. Similarly those at position -3 should preferably be: Ala, Ser, Gly, Cys, Thr, Ile, Leu, Val. Moreover, amino acids in position -6 and -4 from the cleavage site are desirably those capable of inducing the formation of a beta-turn (such as Pro) residues.

The present invention hence encompasses conjugates comprising additional amino acids that may be selected on the basis of the cloning strategy used to produce a cleavable recombinant PHEX. Hence the cleavable recombinant PHEX disclosed in Examples 3 and 4 below contains such additional amino acids upstream of the poly-aspartate and between the poly-aspartate and the native ectodomain sequence. Also, the present invention encompasses a conjugate comprising the secPHEX disclosed in co-pending application no. WO 02/15918 prepared by fusing NL-1 N-terminal fragment comprising a furin site to the PHEX native ectodomain with the vector pcDNA3/RSV/NL-1-PHEX, and a secPHEX comprising an immunoglobulin fragment at its N-terminal. More particularly, FIG. 12 schematically presents the structure of secPHEXs that comprise additional amino acids upstream of the native 46-749 PHEX ectodomain fragment. Constructs no. 1 to 3 and 5 could be fused to a poly-aspartate and be used as conjugates of the present invention. Construct no. 4 constitutes a conjugate of the present invention: it comprises a $D_{10}$ poly-aspartate and a native ectodomain fragment.

The conjugates of the present invention further also encompass sPHEXs comprising deletions at their C-terminal non detrimental to their enzymatic activity.

Furthermore, the present invention comprises conjugates wherein the poly-aspartate would be attached at the C-terminal of the native PHEX ectodomain fragment.

sALP

ALP is a membrane-bound protein anchored through a glycolipid to its C-terminal. This glycolipid anchor (GPI) is added post translationally after removal of a hydrophobic C-terminal end which serves both as transitional membrane anchor and as a signal for the addition of the GPI. Hence the sALP used in Example 6 herein is constituted of an ALP wherein the first amino acid of the hydrophobic C-terminal sequence, namely alanine, is replaced by a stop codon. The soluble ALP so formed contains all amino acids of the native and thus active anchored form of ALP.

The sALP conjugates according to specific embodiments of the present invention thus are any sALP along with a poly-aspartate selected from the group consisting of $D_{10}$ to $D_{16}$ fused immediately downstream of this fragment.

The conjugate may further optionally comprise one or more additional amino acids 1) upstream from the poly-aspartate; and/or 2) between the poly-aspartate and the native sALP fragment or functional equivalent. This is the case for instance when the cloning strategy used to produce the bone targeting conjugate introduces exogenous amino acids in these locations. However the exogenous amino acids should be selected so as not to provide an additional transamination site. The likelihood of a designed sequence being cleaved by the transaminase of the host cell can be predicted as described by Ikezawa (Biol Pharm. Bull. 2002, 25(4) 409-417).

The conjugates of the present invention further also encompass sALPs comprising deletions at their N-terminal non detrimental to their enzymatic activity.

Furthermore, the present invention comprises conjugates wherein the poly-aspartate would be attached at the N-terminal of the native ALP anchored fragment or its biologically active fragment.

The term "recombinant protein" is used herein to refer to a protein encoded by a genetically manipulated nucleic acid inserted into a prokaryotic or eukaryotic host cell. The nucleic acid is generally placed within a vector, such as a plasmid or virus, as appropriate for the host cell. Although E. coli has been used as a host for expressing the conjugates of the present invention in the Examples presented herein, a person of ordinary skill in the art will understand that a number of other hosts may be used to produce recombinant proteins according to methods that are routine in the art. Representative methods are disclosed in Maniatis, et al. Cold Springs Harbor Laboratory (1989). "Recombinant cleavable protein" as used herein is meant to refer to a recombinant protein that may be cleaved by a host's enzyme so as to produce a secreted/soluble protein.

The term "ectodomain fragment" is meant herein when used in relation to PHEX is meant to refer to PHEX's fragment that is located outside of the cellular membrane when found in its native form.

The term "bone tissue" is used herein to refer to tissue synthesized by osteoblasts composed of an organic matrix containing mostly collagen and mineralized by the deposition of hydroxyapatite crystals.

The fusion proteins comprised in the bone delivery conjugates of the present invention are useful for therapeutic treatment of bone defective conditions by providing an effective amount of the fusion protein to the bone. The fusion protein is provided in the form of a pharmaceutical composition in any standard pharmaceutically acceptable carrier, and is administered by any standard procedure, for example by intravenous injection.

The term "pharmaceutically acceptable carrier" is used herein to refer, when parenteral administration is elected as the route of administration, to pharmaceutically acceptable sterile aqueous or non-aqueous solvents, suspensions or emulsions. Examples of non-aqueous solvents are propylene glycol, polyethylene glycol, vegetable oil, fish oil, and injectable organic esters. Aqueous solvents include water; water-alcohol solutions; physiological saline; buffered medical parenteral vehicles including sodium chloride solution, Ringer's dextrose solution, dextrose plus sodium chloride solution, fluid and nutrient replenishers; electrolyte replenishers; Ringer's solution containing lactose, or fixed oils.

The term "effective amount" is used herein to refer to the minimal amount of a pharmaceutical composition that should be administered to a mammal in order to achieve a significant therapeutic effect. The dosages will depend on many factors including the mode of administration. Typically, the amount of protein contained within a single dose will be an amount that effectively prevents, delays or treats bone related undesired condition without inducing significant toxicity. In particular, an effective amount of the conjugate and compositions of the present invention will comprise an amount of fusion protein which will cause a significant alleviation of clinical symptoms of the condition.

The effective amount may be given daily, weekly, monthly or fractions thereof. Typically, a pharmaceutical composition of the invention can be administered in an amount from about 0.001 mg up to about 500 mg per kg of body weight per day (e.g., 10 mg, 50 mg, 100 mg, or 250 mg). Dosages may be provided in either a single or multiple dosage regimen. For example, in some embodiments the effective amount is a dose that ranges from about 1 mg to about 25 grams of the conjugate to be targeted to bone per day, from about 50 mg to about 10 grams of the conjugate to be targeted to bone per day, from about 100 mg to about 5 grams of the conjugate to be targeted to bone per day, about 1 gram of the conjugate to be targeted to bone per day, about 1 mg to about 25 grams of the conjugate to be targeted to bone per week, about 50 mg to about 10 grams of the conjugate to be targeted to bone per week, about 100 mg to about 5 grams of the conjugate to be targeted to bone every other day, and about 1 gram of the conjugate to be targeted to bone once a week.

These are simply guidelines since the actual dose must be carefully selected and titrated by the attending physician based upon clinical factors unique to each patient. The optimal daily dose will be determined by methods known in the art and will be influenced by factors such as the age of the patient and other clinically relevant factors. In addition, patients may be taking medications for other diseases or conditions. The other medications may be continued during the time that the protein for delivery to bone is given to the patient, but it is particularly advisable in such cases to begin with low doses to determine if adverse side effects are experienced.

The term "high stringency conditions" are meant to refer to conditions enabling sequences with a high homology to bind. Without being so limited, examples of such conditions are listed In the handbook "*Molecular cloning, a laboratory manual*, second edition of 1989 from Sambrook et al.: 6×SSC or 6×SSPE, Denhardt's reagent or not, 0.5% SDS and the temperature used for obtaining high stringency conditions is most often in around 68° C. (see pages 9.47 to 9.55 of Sambrook) for nucleic acid of 300 to 1500 nucleotides. Although the optimal temperature to be used for a specific nucleic acid probe may be empirically calculated, and although there is room for alternatives in the buffer conditions selected, within these very well known condition ranges, the nucleic acid captured will not vary significantly. Indeed, Sambrook clearly indicates that the "choice depends to a large extent on personal preference" (see page 9.47). Sambrook specifies that the formula to calculate the optimal temperature which varies according to the fraction of guanine and cytosine in the nucleic acid probe and the length of the probe (10 to 20° C. lower than $T_m$ wherein $T_m$=81.5° C.+16.6($\log_{10}$[Na$^+$])+0.41(fraction G+C)−0.63 (% formamide−(600/l)) (see pages 9.50 and 9.51 of Sambrook).

Other objects, advantages and features of the present invention will become more apparent upon reading of the following non-restrictive description of preferred embodiments thereof, given by way of example only with reference to the accompanying drawings.

BRIEF DESCRIPTION OF THE DRAWINGS

In the appended drawings:

FIG. 4 presents a chromatographic profile of 280 nm detection of PHEX flow for the SP-Sepharose™ HP (A) and the blue-Sepharose HP (B). Straight line represents buffer ratio;

FIG. 7 shows the nucleotide sequence (SEQ ID NO: 1) of a recombinant DNA sequence encoding a protein cleavable so as to produce $D_{10}$-sPHEX;

FIG. 8 shows the amino acid sequence encoded by the $D_{10}$-sPHEX of FIG. 7 (SEQ ID NO: 2);

FIG. 10 shows the amino acid sequence of a native (or membrane-bound) PHEX (SEQ ID NO: 3);

FIG. 11 shows the amino acid sequence (SEQ ID NO: 4) of a $D_{10}$-sPHEX conjugate produced by cleavage of the recombinant cleavable protein of FIG. 8;

FIG. 12 schematically illustrates the structure and activities of various secPHEX constructs. Sequences around or following cleavage sites in these constructs no. 1-5 are also shown (SEQ ID NOs: 45-49, respectively). The furin cleavage site for construct no. 3 is also shown (SEQ ID NO: 50);

FIG. 16 shows A. the nucleotidic sequence (SEQ ID NO: 5) of a soluble alkaline phosphatase; and B. the amino acid sequence (SEQ ID NO: 6) of that soluble alkaline phosphatase;

FIG. 17 shows A. the nucleotidic sequence (SEQ ID NO: 7) encoding a conjugate of the present invention, namely sALP-$D_{10}$; and B. the amino acid sequence (SEQ ID NO: 8) of that conjugate.

DESCRIPTION OF ILLUSTRATIVE EMBODIMENTS

Figure 1:
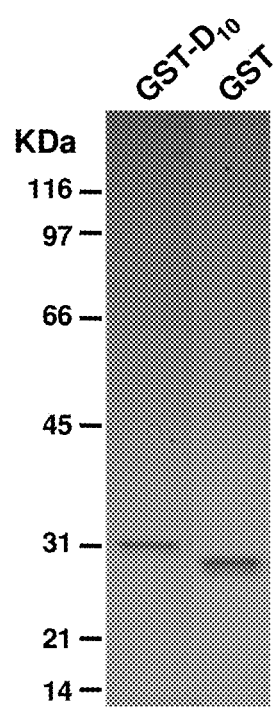
FIG. 1 presents the purity status of GST and GST-$D_{10}$ proteins on an SDS polyacrylamide gel after CL-4B chromatography.

The present invention showed that specific poly-aspartic peptides fused in frame to a protein, as exemplified herein by the gluthatione-S-transferase protein (GST), used as a reporter protein, by sPHEX and by sALP, can significantly increase the bone binding capacity of these proteins.

The present invention is illustrated in further details by the following non-limiting examples.

Table 1 presents the sequence of oligonucleotides used in Examples 1 to 7.

TABLE 1

| | SEQUENCE OF SYNTHETIC OLIGONUCLEOTIDES USED IN EXAMPLES 1 TO 7 | |
|---|---|---|
| $D_6$ | SEQ ID NO: 9. | 5'-GATCCGATGACGATGACGATGACGC-3' |
| | SEQ ID NO: 10. | 5'-GGCCGCGTCATCGTCATCGTCATCG-3' |
| $D_{10}$ | SEQ ID NO: 11. | 5'-GATCCGATGACGATGACGATGACGATGACGATGACGC-3' |
| | SEQ ID NO: 12. | 5'-GGCCGCGTCATCGTCATCGTCATCGTCATCGTCATCG-3' |
| $D_{16}$ | SEQ ID NO: 13. | 5'-GATCCGATGACGATGACGATGACGATGACGATGACGATGACGATGACGC-3' |
| | SEQ ID NO: 14. | 5'-GGCCGCGTCATCGTCATCGTCATCGTCATCGTCATCGTCATCGTCATCG-3' |
| hMEPE | SEQ ID NO: 15. | 5'-GATCCGATGACAGTAGTGAGTCATCTGACAGTGGCAGTTCAAGTGAGAGCGATGGTGACGC-3' |
| | SEQ ID NO: 16. | 5'-GGCCGCGTCACCATCGCTCTCACTTGAACTGCCACTGTCAGATGACTCACTACTGTCATCG-3' |
| hStatherin | SEQ ID NO: 17. | 5'-GATCCGATTCATCTGAAGAGAAATTTTTGCGTAGAATTGGAAGATTCGGTGC-3' |
| | SEQ ID NO: 18. | 5'-GGCCGCACCGAATCTTCCAATTCTACGCAAAAATTTCTCTTCAGATGAATCG-3' |
| hMGP | SEQ ID NO: 19. | 5'-GATCCTGTTATGAATCACATGAAAGCATGGAATCTTATGAACTTAATCCCTTCATTGC-3' |
| | SEQ ID NO: 20. | 5'-GGCCGCAATGAAGGGATTAAGTTCATAAGATTCCATGCTTTCATGTGATTCATAACAG-3' |
| hOsteopontin | SEQ ID NO: 21. | 5'-GATCCCAGAATGCTGTGTCCTCTGAAGAAACCAATGACTTTAAAGC-3' |
| | SEQ ID NO: 22. | 5'-GGCCGCTTTAAAGTCATTGGTTTCTTCAGAGGACACAGCATTCTGG-3' |
| hBSP2 | SEQ ID NO: 23. | 5'-GATCCGGCAGTAGTGACTCATCCGAAGAAAATGGAGATGACAGTTCAGAAGAGGAGGAGGAAGC-3' |
| | SEQ ID NO: 24. | 5'-GGCCGCTTCCTCCTCCTCTTCTGAACTGTCATCTCCATTTTCTTCGGATGAGTCACTACTGCCG-3' |
| hIGFBP5 | SEQ ID NO: 25. | 5'-GATCCCGCAAAGGATTCTACAAGAGAAAGCAGTGCAAACCTTCCCGTGGCCGCAAGCGTGC-3' |
| | SEQ ID NO: 26. | 5'-GGCCGCACGCTTGCGGCCACGGGAAGGTTTGCACTGCTTTCTCTTGTAGAATCCTTTGCGG-3' |
| M81736 CBS | SEQ ID NO: 27. | 5'-AGTCGGGATCCGGAACAAGCAGCGTGTTCTAC-3' |
| | SEQ ID NO: 28. | 5'-AGATCGCGGCCGCTCAATTGTGCACGGTGTGATTAAAGG-3' |
| $D_{10}$ | SEQ ID NO: 29. | 5'-CCGGAGATGACGATGACGATGACGATGACGATGACT-3' |
| | SEQ ID NO: 30. | 3'-TCTACTGCTACTGCTACTGCTACTGCTACTGAGGCC-5' |

Example 1

Bone Binding of GST-$D_6$, GST-$D_{10}$ and GST-$D_{16}$

Recombinant DNA technology was used to generate a plasmid containing a nucleic acid encoding GST followed in frame by a nucleic acid encoding a $D_6$, $D_{10}$ or $D_{16}$ acidic peptide. To obtain the GST-$D_6$, GST-$D_{10}$ and GST-$D_{16}$ conjugates, the oligonucleotide of SEQ ID NO:9 (see Table 1) was first mixed with the oligonucleotide of SEQ ID NO:10, oligonucleotide of SEQ ID NO:11 mixed with oligonucleotide of SEQ ID NO:12, and oligonucleotide of SEQ ID NO:13 mixed with oligonucleotide of SEQ ID NO:14. This procedure generated duplex oligonucleotides coding for $D_6$, $D_{10}$ and $D_{16}$, respectively, and having extremities compatible with cloning in the pGEX3T-4 plasmid (Pharmacia biotechnology) pre-digested with restriction endonucleases BamHI and NotI. pGEX3T-4 vectors were transformed into AP401 protease minus E. coli bacteria strain (lon::mini tetR ara-Δlac-pro nalA argEam rifR thil [F' pro AB lacIq Z M15]).

Positive bacterial colonies were used to seed a 10 ml pre-culture of double YT media and 100 mg/liter ampicilin. Bacteria were grown overnight at 37° C. in an orbital shaker set at 250 rpm. The pre-culture was added to 500 ml of fresh double YT ampicilin media in a 2 liters Erlenmeyer flask. Bacteria were let to grow at 37° C. under orbital shaking until a 595 nm optical density of 0.7 was reached. Protein expression was then induced by adding 500 µl of 0.1 M IPTG solution and the bacteria put back to incubation for 2 hours. Bacteria were spun down at 8000×g for 10 minutes at 4° C. The pellet was suspended in 25 ml of ice-cold PBS containing Complete-EDTA caplet protease inhibitor (Boehringer Mannheim) and frozen at −20° C.

Bacteria cells were thawed and disrupted on ice with 6 pulses of sonication every 50 seconds prior to centrifugation at 12000×g for 10 minutes at 4° C. Supernatant was mixed with 500 µl of GS-4B wet resin (Amersham Pharmacia Biotech) equilibrated with PBS. The resin was kept as a suspension during the overnight incubation at 4° C. The resin was rinsed with PBS until 280 nm optical density was below 0.01. Resin was then laid on an empty column and proteins eluted with 10 mM glutathione dissolved in PBS. The pooled elution fractions were dialyzed against 1 mM sodium $PO_4$ pH 7.4 and 150 mM NaCl. Dialyzed proteins were filtered in a sterile environment on 0.22 µm PES membrane and kept at 4° C. Typically 40 and 60 mg of pure proteins were recovered per liter of culture respectively. FIG. 1 shows an example of an SDS-PAGE analysis of the purified GST and GST-$D_{10}$. Purified proteins were iodinated using Iodo-Beads Iodination Reagent (Pierce).

GST and peptide-fused GST were dialyzed against PBS and concentration set to 2 mg/ml. Iodination reaction was initiated by adding 2 PBS-rinsed Iodo-Beads to 2 mCi of Na125I (100 µCi/µl, ICN) dissolved in 500 µl of PBS. Beads were incubated at room temperature for five minutes before adding 1 mg of dialyzed protein. The iodination reaction proceeded for 15 minutes before the bead was removed and rinsed in 500 ml of PBS. To the final 1.5 ml of iodinated protein solution, 15 µl of 6 mM NaI was added to dilute non-specific radioactivity. The mixture was then desalted using PD-10 gel filtration columns (Amersham Pharmacia Biotech) equilibrated with PBS. Proteins eluted in the void volume. They were concentrated and dialysed against the in vivo buffer (1 mM sodium PO4 pH 7.4 and 150 mM NaCl) using Centriprep-YM10™ cartridges (Amicon). Radioactivity was measured using a gamma radiation counter, protein concentration was assessed by the Bradford assay and $^{125}I$ chemical linkage to proteins was revealed by autoradiography of dried SDS-PAGE. Iodinated samples were kept at 4° C.

Bone Binding Ability of GST-Poly-Aspartic Peptides Fusion Proteins Compared to that of GST Alone The iodinated GST-fusion proteins were injected to mice under isoflurane anesthesia as an intravenous bolus through the subclavian vein. A dose of 1 mg of iodinated protein/per kg body weight was injected. The maximum dose volume was set at 10 ml/kg. Duration of treatment was sixty minutes. Ten and sixty minutes after injection, blood samples (0.1 to 0.2 ml) were collected via the subclavian vein under anesthesia into serum/gel clotting activator Microvette™ tubes (Sarstedt, #20.1291). At necropsy, blood samples were collected and animals were sacrificed by exsanguination from the heart under isoflurane anesthesia. Organs (kidneys, liver, femurs, tibias and thyroid) were collected, rinsed in saline 0.9% USP, blotted on gauze and transferred into gamma counter tubes. Serum samples and organs were weighted and radioactivity was measured.

Results were expressed as percentage of injected dose. Neither $D_{10}$-GST nor $D_{16}$-GST promoted binding to other organs than bone. This showed the specificity of these conjugates to bone (Data not shown).

Figure 2:
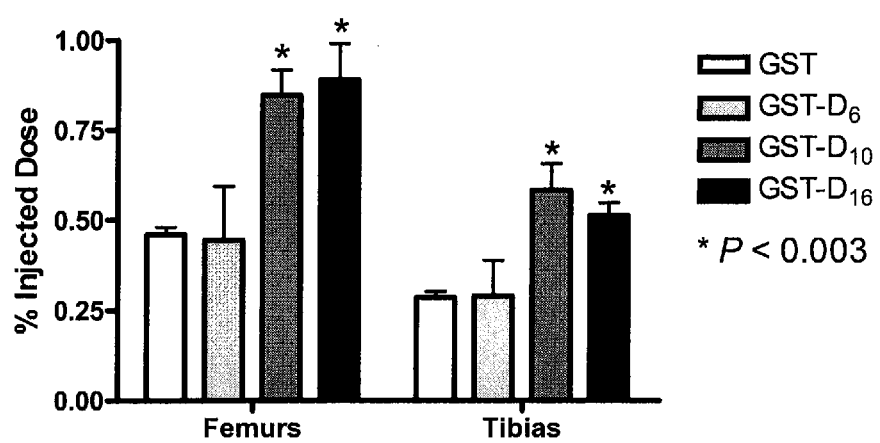
FIG. 2 shows the promotion of GST binding to bone by $D_6$, $D_{10}$ and $D_{16}$ peptide motifs through the percentage of the injected dose of recombinant GST found associated with specific tissues.

FIG. 2 shows that GST-$D_6$ fusion protein did not bind more to tibia or femur than GST alone. In contrast, $D_{10}$ and $D_{16}$ peptide motifs promoted GST binding to bones.

The fact that $D_6$, a peptide shown to successfully deliver small molecules to bone could not successfully deliver a protein, namely GST, to bone shows that it is not predictable whether a specific acidic peptide known to effectively deliver a small molecule to bone will also be effective in delivering a protein to bone.

Example 2

Binding Ability of GST Fused with Various Peptides

Human matrix extracellular phosphoglycoprotein (hMEPE) is a protein synthesized by osteoblasts that shows major similarities to a group of bone and teeth mineral matrix phosphor-glycoproteins, proteins known to naturally bind to bone matrix (8). Of particular importance, hMEPE presents at its carboxy-terminus a sequence of 18 amino acid residues (DDSSESSDSGSSSESDGD) (SEQ ID NO: 31) similar to acidic peptides found in dentin phosphorin and dentin sialophosphoprotein, both known to bind to bone matrix (8).

Human Statherin (hStatherin) is a protein synthesized by salivary glands, which similarly to histatin directly modulates hydroxyapatite nucleation and/or growth. Of particular importance, hStatherin presents a sequence of 15 amino acid residues at positions 20 to 34 (DSSEEKFLRRIGRFG) (SEQ ID NO: 32) that was shown to bind tightly to hydroxyapatite (9).

Human Matrix Gla Protein (hMGP) is a protein synthesized by vascular smooth muscle cells and chondrocytes that functions as an inhibitor of hydroxyapatite polymerization by binding to crystal nuclei. Of particular importance, hMGP presents at its amino-terminus a sequence of 17 amino acid residue at positions 19 to 35 of the open reading frame (CYESHESMESYELNPFI) (SEQ ID NO: 33) similar to phosphorylated gamma carboxyglutamic acidic peptides found in osteocalcin known to bind to bone matrix, and thought to promote binding to bone matrix (10).

Human osteopontin (hOPN) is a protein synthesized by osteoblasts that regulates hydroxyapatite crystal growth. This protein belongs to the bone sialophosphoprotein family. Of particular importance, hOPN presents a sequence of 13 amino acid residue (QNAVSSEETNDFK) (SEQ ID NO: 34) at positions 58 to 70 of the open reading frame. This sequence shows a high level of homology among mammal species. Secondary structure prediction makes this sequence appropriate to solvent exposure and this sequence was shown to be phosphorylated at its serine residues. This latter characteristic is thought to affect binding to bone matrix (11).

Human Bone Sialo-protein II (hBSP2) is a protein synthesized by osteoblasts that shows major similarities to a group of bone and teeth mineral matrix phospho-glycoproteins, proteins known to naturally bind to bone matrix. Of particular importance, hBSP2 presents at its amino-terminus a sequence of 18 amino acid residues at positions 62 to 79 of the open reading frame (GSSDSSEENGDDSSEEEE)

(SEQ ID NO: 35) similar to acidic peptides found in dentin phosphophoryn and MEPE, and thought to promote binding to bone matrix (8).

Human Insulin-like Growth Factor binding protein-5 (hIGFBP5) is synthesized by osteoblasts. This protein, similarly to proteins of the IGFBP family, is thought to regulate osteoblast function in the bone remodeling process. Of particular importance, hIGFBP5 presents a sequence of 18 amino acid residues at positions 221 to 238 of the open reading frame (RKGFYKRKQCKPSRGRKR) (SEQ ID NO: 36) that was shown to bind tightly to hydroxyapatite (12).

Staphylococcus aureus collagen adhesin (M81736) is a protein expressed at the surface of S. aureus that promotes bacteria binding to collagen matrix of mammalian bone and cartilageneous tissues. Such a binding was reported to be instrumental in the development of pathogenesis such as osteomyelitis and infectious arthritis. Of particular importance, the collagen binding domain (CBS) of this adhesin was reported to encompass 151 amino acid residues (G168 to N318) of the open reading frame of the protein (13, 14). The amino acid primary sequence being the following:

(SEQ ID NO: 37)
GTSSVFYYKTGDMLPEDTTHVRWFLNINNEKSYVSKDITIKDQIQGGQQL

DLSTLNINVTGTHSNYYSGQSAITDFEKAFPGSKITVDNTKNTIDVTIPQ

GYGSYNSFSINYKTKITNEQQKEFVNNSQAWYQEHGKEEVNGKSFNHTVH

N.

Plasmids containing the acidic peptide sequences derived from hMEPE, hStatherin, hMGP, hOPN, hBSP2, hIGFBP5 and CBS following GST in frame were constructed to determine whether they could promote bone targeting of a recombinant protein. Recombinant DNA technology as described in Example 1 was used to generate plasmids for hMEPE, hStatherin, hMGP, hOPN, hBSP2 and hIGFBP5 derived peptides. The oligonucleotide pairs identified in Table 1 for each of these peptides were mixed to obtain the corresponding GST-acidic peptide fusion protein. This procedure generated duplex oligonucleotides coding for these acidic peptides and having extremities compatible with cloning in the pGEX3T-4 (Pharmacia biotechnology) plasmid pre digested with restriction endonucleases BamHI and NotI.

A CBS-containing plasmid was constructed as follows. A synthetic gene corresponding to the CBS sequence was obtained from Bio S&T (Montreal) and inserted in plasmid pLIV Select. Oligonucleotides of SEQ ID NO: 27 and 28 were used as primers in PCR reactions with plasmid pLIV Select containing the CBS gene to amplify the CBS specific sequences. pGEX-4T-3 vectors were transformed into AP401 protease minus E. coli bacteria strain (lon::mini tetR ara-Δlac-pro nalA argEam rifR thil [F' pro AB lacIq Z M15]).

Protein production and purification, and pharmacodistribution of the iodinated fusion protein were performed as described in Example 1.

None of these GST-acidic peptides was shown to bind to bones (result not shown).

The fact that the peptide derived from statherin, a peptide shown to successfully deliver a small portion of osteopontin to bone, could not successfully deliver the GST protein to bone shows that it is not predictable whether a specific acidic peptide known to effectively deliver a small peptide to bone will also be effective in delivering a protein to bone.

Example 3

$D_{10}$ Increases sPHEX's Ability to Correct Alkaline Phosphatase Levels in Mice PHEX is a metallopeptidase that is widely believed to control the level of bone peptide factors involved in the regulation of mineralization and kidney phosphate homeostasis. PHEX is expressed at the surface of osteoblasts and osteocytes in contact with or imbedded in the bone matrix. This example provides data on the design, production and purification of an extended form of sPHEX containing at its N-terminus a sequence of 10 aspartic acid residues designed to anchor itself to the bone matrix.

$D_{10}$sPHEX Expression Vector

A BspEI endonuclease restriction site was inserted by site directed mutagenesis (QuickChange, Stratagene) into the pcDNA3-RSV-sPHEX-NEO vector (Boileau G. et al., Biochem. J. (2001) 355, 707-13) using the following oligonucleotide primers:

(SEQ ID NO: 38)
5'-CAGTCAAGGTCTCTTA<u>TCCGGA</u>AGTCTCCAAGCTAAACAGG-3'
and (SEQ ID NO: 39)
5'-CTGTTTAGCTTGGAGACT<u>TCCGGA</u>TAAGAGACCTTGACTGG-3'.

Figure 3:
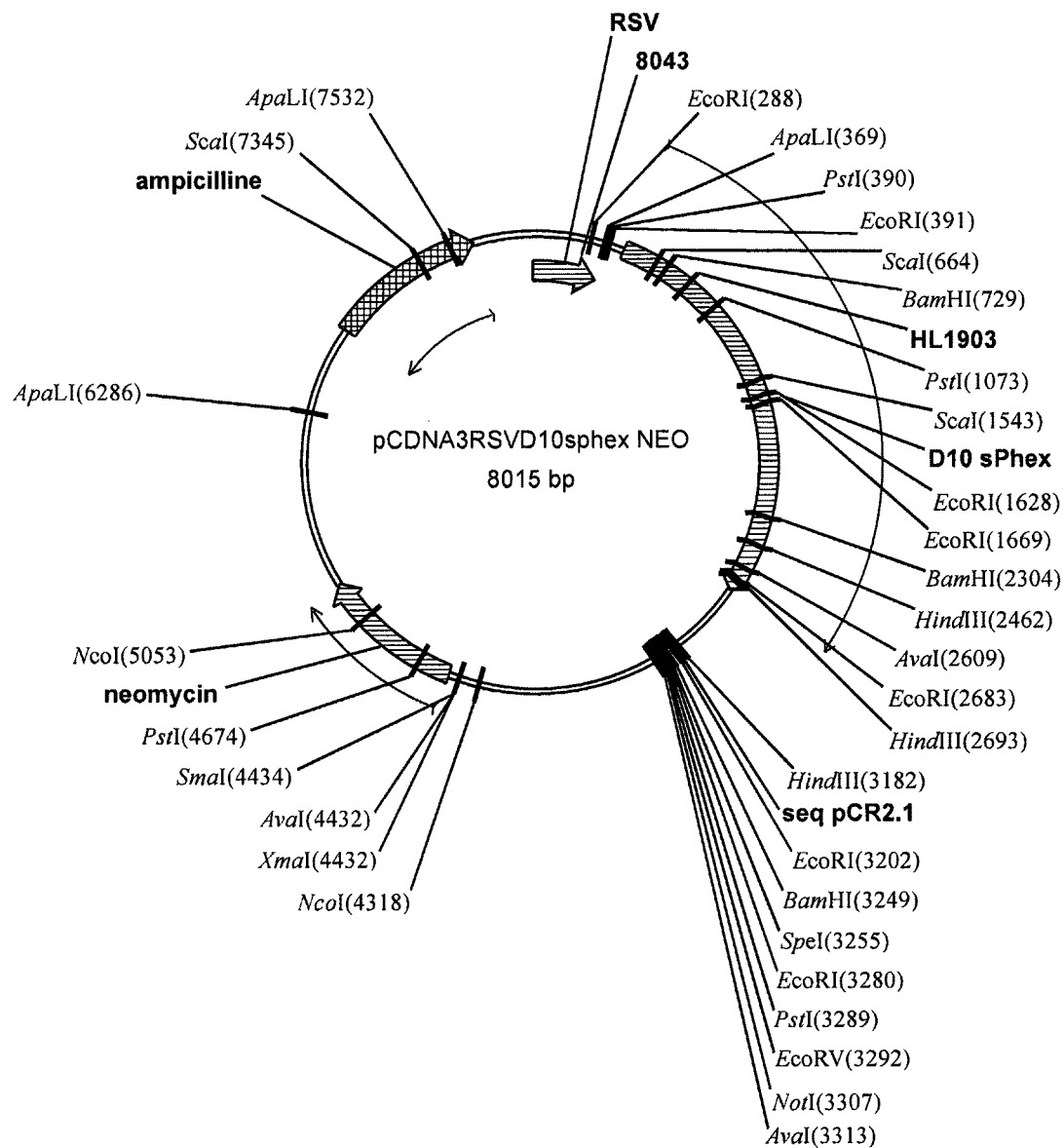
FIG. 3 provides a schematic representation of the plasmid pcDNA3-RSV-$D_{10}$sPHEX-NEO vector.

The hexamer BspEI sequence (underlined) was inserted in frame with and upstream of the sPHEX DNA sequence. This construct encodes a recombinant protein which is cleavable between the leucine and serine at positions 41 and 42, respectively in FIG. 8. It is constituted therefore of two exogenous amino acids, followed downstream by a deca-aspartate, which is in turn followed by two additional exogenous amino acids. These 4 exogenous amino acids derive from the cloning strategy used to produce the conjugate. These exogenous amino acids were shown not to defeat the enzymatic activity of the conjugate (See FIG. 12 showing the specific activity of this construct) but may be dispensed with. Downstream of these exogenous amino acids is an ectodomain fragment of the native PHEX starting therefore with the serine at position 46 of the sequence presented in FIG. 10. The modified pcDNA3-RSV-NEO vector was cleaved with BspEI and then digested with alkaline phosphatase to remove the 5' phosphate moieties. An oligonucleotide duplex coding for deca-aspartate: [5'-CCGGAGATGACGATGACGATGACGATGACGAT-GACT-3' (SEQ ID NO: 29) and 3'-TCTACTGCTACTGC-TACTGCTACTGCTACTGAGGCC-5' (SEQ ID NO: 30)] was first phosphorylated on its 5' ends with T4 polynucleotide kinase and ligated to the BspEI digested vector. This yielded the pcDNA3-RSV-$D_{10}$sPHEX-NEO vector (FIG. 3). This vector comprised the sequence presented in FIG. 7 which encodes the recombinant cleavable PHEX having the amino acid sequence presented in FIG. 8.

Expression of Recombinant $D_{10}$sPHEX

To induce the stable expression of the $D_{10}$sPHEX protein, the pcDNA3-RSV-$D_{10}$sPHEX-NEO vector was transfected in LLC-PK1 cells (Porcine Kidney cells; ATCC No. CRL-1392) using the Lipofectamine-Plus™ liposome transfection kit (Invitrogen). Transfected cells were selected by adding 400 μg/ml G-418 (Life Technologies) to the medium. Clones of G-418 resistant cells were screened for $D_{10}$sPHEX expression using the PHEX fluorescent enzymatic assay [Campos M. et al. Biochem. J. (2003) 373, 271-9]. The apparent molecular weight of the protein recovered in the spent medium was estimated by immunoblotting using a monoclonal antibody raised against a recombinant human PHEX fragment (K121-E294) as described previously (Ruchon A F et al. J. Bone Miner. Res. (2000) 15, 1440-1450). A G-418 resistant clone expressing 1 to 2 mg of D10sPHEX per liter was used for protein production. Cells were seeded in Cellstack-10™ (Corning) at a density of $7 \times 10^7$ in 1.75 liters of media (199 media, 6% FBS, 1 mM NaPyruvate, Penicillin $1 \times 10^5$ U/liter, Streptomycin 100 mg/liter and 1% G-418. $D_{10}$sPHEX expression was increased by incubating the cells in 1.75 liter of DMEM+10 mM sodium butyrate for four days at 37° C. and 5% $CO_2$ prior to harvest of the spent medium.

Purification and Characterization

Figure 5:
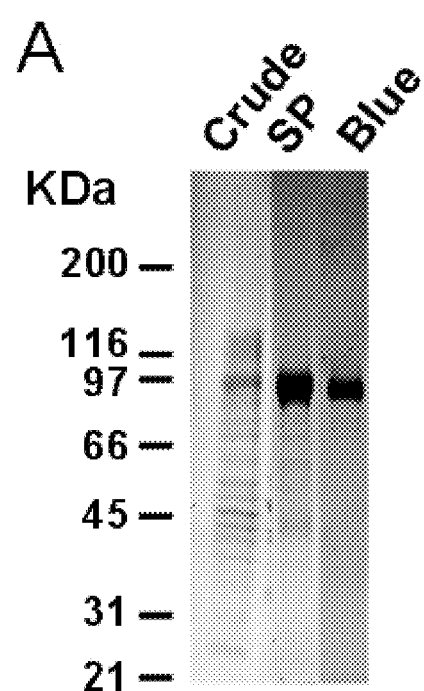
FIG. 5 presents a Sypro-Ruby™ stained SDS-PAGE analysis of the different fractions collected throughout $D_{10}$sPHEX purification procedure.

Cell supernatant was centrifuged at 500×g for 5 minutes at 4° C. and filtered on fiberglass (Fisher, APFC09050) and concentrated 10 to 40 times using an Ultrasette™ 30 tangential flow filtration device (Pall Canada). The pH of the solution was brought to 5.6 with 1M acetic acid before an overnight dialysis at 4° C. against 50 mM sodium acetate, 100 mM NaCl pH 5.6 (SP-buffer). The dialyzed supernatant was loaded, at a flow rate of 4 ml/min, on a 20 ml SulfoPropyl-Sepharose cation-exchange column (Amersham Pharmacia Biotech) previously equilibrated with SP-buffer. The column was washed with the same buffer at the same flow rate until 280 nm absorbance baseline was reached. Most of the contaminant proteins were then eluted with a 226 mM NaCl step in the SP buffer. D10sPHEX was then eluted with a 280 mM NaCl step (FIG. 4A). Fractions were analyzed by SDS-PAGE and with the PHEX enzymatic activity assay. Fractions containing sPHEX were pooled and extensively dialyzed against 20 mM MOPS pH 7, 250 mM NaCl prior to loading on a 5 ml Blue-Sepharose™ HP (Amersham Pharmacia) column at 5 ml/min. The column was rinsed, at the same flow rate with the same buffer and most of the D10sPHEX protein was recovered by increasing the NaCl concentration stepwise to 350 mM (FIG. 4B). Purity of the final fraction was greater than 95%. Alternatively, the Blue-Sepharose™ could be replaced by Heparin-Sepharose™ (Amersham Pharmacia) on which D10sPHEX binds tightly over a range of pH (5 to 8). D10sPHEX was eluted by using NaCl gradient. Purity was determined to be above 90%. D10sPHEX was concentrated and dialyzed against 1 mM sodium PO4 pH 7.4, 150 mM NaCl using Centriprep-50™ cartridges. Dialyzed sample was filtered in a sterile environment on 0.22 µm membrane. Purified D10sPHEX was shown to remain stable over months at 4° C. Protein concentrations were determined using the Bradford method (DC protein assay kit; Biorad) with bovine serum albumin (BSA) as a standard. Protein purity was assessed by Sypro-Ruby™ (Molecular Probes) staining of proteins resolved on SDS-PAGE 4-12% (FIG. 5). D10sPHEX enzymatic activity was determined using the fluorigenic substrate.

Effect of sPHEX and $D_{10}$-sPHEX Injections on Circulating Levels of Alkaline Phosphatase in Hyp Mice The X-linked Hyp mice harbors a large deletion in 3' region of the PHEX gene and is the murine homologue of human X-linked hypophosphatemia (XLH). These mice therefore represent a useful model to study the pathophysiology of XLH as well as a to test the efficacy of therapeutic agents in preclinical studies.

The potential therapeutic effect of $D_{10}$sPHEX and sPHEX was thus investigated with bolus intravenous injection to Hyp/Y mice over a 2 week period.

$D_{10}$sPHEX and sPHEX were dialyzed against vehicle and the solutions were filtered through 0.22 µm low binding protein filter. The solutions were aliquoted and re-assayed for enzymatic activity and concentration by fluorogenic enzymatic assay and Bradford method, respectively.

Each mouse was anesthetized with vaporized Isoflurane (2%) and $D_{10}$sPHEX, or sPHEX were injected as an intravenous bolus through the subclavian vein. The dose was 5 mg/kg of body weight for each group. The animals were treated once daily for 14 consecutive days. Blood samples (0.1-0.2 ml) were collected via the subclavian vein under anesthesia on study days-3 and +15 (before necropsy, 24 hours after last injection). Total Alkaline phosphatase (ALP) levels were assayed in diluted serum (30 µl of serum sample with 90 µl of 0.9% saline USP). Although, appropriate dosages for human patients are not proportional to those used in mice, these dosages are predictive of the dosages ranges that could be suitable in humans using published tables.

Figure 6:
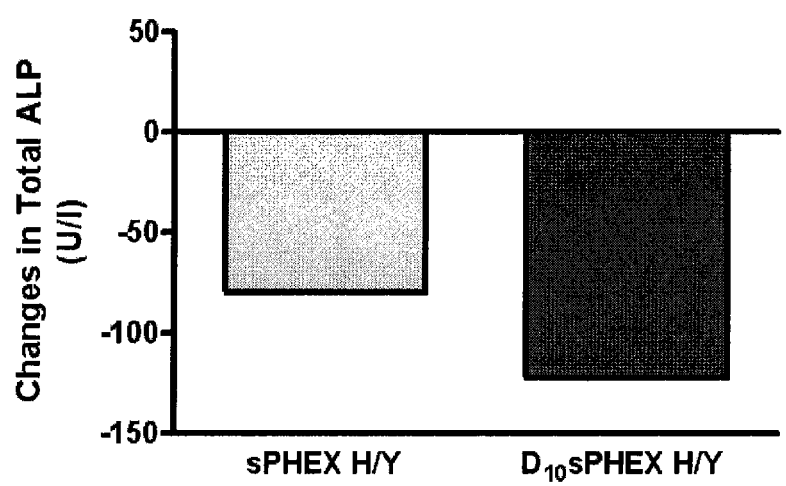
FIG. 6 shows the variation in serum alkaline phosphatase levels (ALP) observed in Hyp mice injected daily with i.v. doses of sPHEX and $D_{10}$-sPHEX for 14 days. U/l values represent the decrease observed between day-3 (corresponding in the graphic to 0 U/l) and day 15 of the injection regimen and are the mean of measures made on 6 animals.

As seen in FIG. 6 the $D_{10}$-extended form of sPHEX induced a larger decrease in alkaline phosphatase levels than the normal sPHEX form.

Example 4

$D_{10}$ Fusion to Recombinant GST Increases its Binding to the Mineral Phase of Bone In Vitro Fluorescein Labelling of Purified Proteins Recombinant purified proteins were labelled with fluorescein-isothiocyanate (FITC, Molecular Probes F143). Reaction was carried out by adding proteins to 10 mM sodium phosphate, 50 mM NaCl buffer pH 7 at a final protein concentration of 1 mg/ml. Labelling reaction was started by adding FITC dissolved in DMSO at a concentration of 20 mg/ml to reach 20:1 molar ratio with respect to the protein concentration. The mixture was left to react at room temperature for an hour. Labelled protein was separated from the free fluorescein on a PD-10™ column (Pharmacia) prior to dialysis in the binding buffer (1 mM sodium phosphate 150 mM NaCl, pH 7.4).

Preparation of the Mineral Phase of Bones

Long bones were dissected from a rat and crushed to powder in a liquid nitrogen cooled mortar. The powder was either kept at −80° C. or directly used. An aliquot of the powder (300 mg) was washed 3 times with 8 ml of PBS and 8 ml of 1 M HCl were added. The mixture was kept in suspension on a rotating mixer for 1 hour at room temperature. The insoluble fraction was spun down and the clear acidic supernatant collected. This acidic solution was stable at room temperature for at least two weeks.

Binding Reaction

Aliquots of 20 µl of the acidic bone extract were mixed with 2 µl of 10 M NaOH and the precipitate was pelleted 10,000×g for 3 minutes at room temperature. The pellet was rinsed twice by resuspending in 100 µl of binding buffer. The bone extract was then mixed with 100 µl of a solution containing 5 to 45 µg of fluorescein-labelled protein in the binding buffer to which phosphate was added to reach a final concentration of 80 mM. The samples were incubated for 30 minutes at room temperature on the rotating wheel to keep the mineral phase in suspension. The samples were then centrifuged for 3 minutes at room temperature. The pellet containing the bound protein was dissolved in 200 µl of 0.5 M EDTA pH 8. To estimate the amount of free protein present, 100 µl of 0.5 M EDTA pH 8 was added to the supernatant. Fluorescence of the different samples was measured on a 96 wells plate reader set at 494 nm for excitation and 516 nm for emission.

Results

Figure 9:
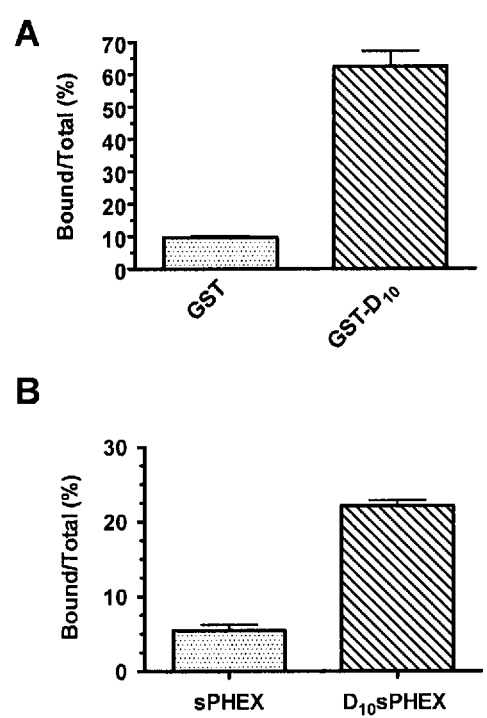
FIG. 9 compares the binding to the mineral phase of bone of proteins (A. GST B. sPHEX) with that of their decaaspartate fused counterparts.

Samples containing 50 µg of fluorescein-labelled GST and GST-$D_{10}$ were used in the binding assay described above. FIG. 9 A shows that fusion of the $D_{10}$ sequence to GST caused a 6-fold increase in binding to the mineral phase of bone.

Example 5

$D_{10}$ Fusion to sPHEX Increases its Binding to Bone

Using a procedure analogous to that described in Example 4 above, samples containing 50 µg of fluorescein-labelled sPHEX and $D_{10}$sPHEX were used in a binding assay. FIG. 9 B shows that fusion of the $D_{10}$ sequence to sPHEX caused a 4.3 increase in binding to the mineral phase of bone.

In contrast, $D_6$-sPHEX was constructed and tested after in vivo injection in animals (as described in Example 1 above) and did not promote binding of recombinant proteins to bone (Data not shown).

Example 6

$D_{10}$ Fusion to a Soluble Form of Alkaline Phosphatase Increases its Targeting to the Mineral Phase of Bone Construction of Expression Vectors Encoding Human Recombinant Soluble Phosphatase Alkaline, sALP and sALP-$D_{30}$ The human full length cDNA encoding tissue non-specific alkaline phosphatase (ALP) was obtained from bone marrow polyA RNA (Clonetech) by RT-PCR. Briefly, 20 ng of polyA was reverse transcribed with SuperscriptII™ and an oligo $dT_{12-18}$ using the First Strand Synthesis System (Invitrogen). An aliquot representing $\frac{1}{20}^{th}$ of the RT step was used directly in a PCR reaction with ALP specific oligos (forward 5'-gataaagcaggtcttggggtgcacc-3' (SEQ ID NO: 40); reverse 5'-gttggcatctgtcacgggcttgtgg-3' (SEQ ID NO: 41)) and the Expand High Fidelity Enzyme Kit™ (Roche). The resulting ALP specific product (1644 bp) was separated on and purified from an agarose gel (1%) using the Qiaquick Gel Extraction Kit™ (QIAGEN). The ALP cDNA was then ligated into the pCR4-blunt-TOPO™ vector (Invitrogen), transformed into Top10™ bacteria (Invitrogen), and a positive clone identified by colony PCR. The identity of the cDNA was verified by automated DNA sequencing.

Secreted forms of ALP (sALP) having the GPI anchor signal removed were constructed by PCR using Expand High Fidelity Kit™. They comprised residues 1-502 followed by either a stop codon (sALP) or a deca aspartate targeting motif and a stop codon (sALP-D10). In both cases the forward primer (5'-tggatccacc<u>atg</u>atttcaccattcttagtac-3' (SEQ ID NO: 42)) covered the initiator methionine (underlined) and included a BamHI site (italicized). The reverse primers (sALP: 5'-ttctaga<u>cta</u>cgagctggcaggagcacagtggccg-3' (SEQ ID NO: 43); sALP-D10 5'-ttctaga<u>ctagtcgtcatcatcgtcatcatcgtcgtcatccgagaggcaggagcacagtggccg</u>-3' (SEQ ID NO: 44) contained a stop codon (underlined) and an XbaI site (italicized). The PCR products were digested with BamHI and XbaI and cloned into the pCDNA3.1-RSV that had been pre-digested with the same enzymes. Plasmid DNA was sequenced.

ALP Fluorescent Enzymatic Assay

Enzymatic activity of sALP and sALP-$D_{10}$ was assayed using 4 methylumbelliferyl phosphate (MUP, Molecular Probes, M8425) as a fluorigenic substrate according to Gee K R et al. (Anal. Biochem. 273, 41-48 (1999)) Typically, the assay was carried out at 37° C. in 96-well plates in a final volume of 200 µl with 10 µM of MUP. Readings were recorded using a Spectramax Gemini™ (Molecular Devices) plate reader every minute for 30 minutes at 450 nm upon excitation at 360 nm. Emission wavelength cut-off was set at 435 nm. ALP initial speed rate was estimated by linear regression fitting (with $r^2$ equal or greater than 0.98).

Expression of Recombinant sALP and sALP-$D_{10}$ Proteins

In order to determine whether the recombinant sALP and sALP-$D_{10}$ proteins were secreted, each construct (pcDNA3-RSV-sALP-NEO and pcDNA3-RSV-sALP-$D_{10}$-NEO) was transiently transfected in HEK-293S cells (Human Embryonic Kidney cells; ATCC No. CRL-1392) using the Lipofectamine-Plus liposome transfection kit™ (Invitrogen). HEK-293S cells were also mock-transfected as a negative control. The day after transfection, cells were incubated for 24 h in serum-free DMEM. The conditioned media were collected and centrifuged at 14000 RPM for 5 min at 4° C. to remove dead cells and debris. The supernatants were assayed for sALP or sALP-$D_{10}$ enzymatic activity and expression using the ALP fluorescent enzymatic assay and Western blotting respectively. For Western blotting, the spent media were precipitated for 1 h on ice with trichloroacetic acid (final concentration 10% (v/v)). The precipitated proteins were spun down at 14000 RPM for 20 min at 4° C., washed once with chilled acetone, dried, and resuspended in 60 µl 1× Laemmli sample buffer with DTT and boiled for 5 min.

To evaluate the intracellular content of sALP and sALP-$D_{10}$ the cells were washed 3 times with PBS and lysed with 200 µl Tris-HCl 50 mM (pH 8) containing 150 mM NaCl and 1% NP-40 on ice for 20 min. The lysates were spun down and the supernatant was assayed for sALP or sALP-$D_{10}$ enzymatic activity and expression using the ALP fluorescent enzymatic assay and Western blotting, respectively. For Western blotting, 50 µl aliquots were mixed with 10 µl 6× Laemmli sample buffer with DTT and boiled for 5 min.

Samples were loaded on a Novex Precast™ 4-12% Tris-Glycine polyacrylamide gel (Invitrogen) and transferred onto 0.45 µm nitrocellulose (Protran, Schleicher&Schuell, Keene, N.H.) with Tris-glycine containing 10% methanol. The membrane was stained with Ponceau red and blocked for 1 h at room temperature with PBS containing 0.05% Tween 20™ (PBST) and 5% dried milk). The membrane was then sequentially incubated at room temperature with the anti-hBAP antibody (mAb 4B-78, Developmental Studies Hybridoma Bank) (1:1000 in PBST with 5% dried milk) and a rabbit anti-mouse IgG coupled to horseradish peroxidase (Sigma) (1:12000 in PBST with 5% dried milk). The signal was developed with the Western Lightning Chemiluminescence Reagent Plus™ (PerkinElmer).

Figure 13:
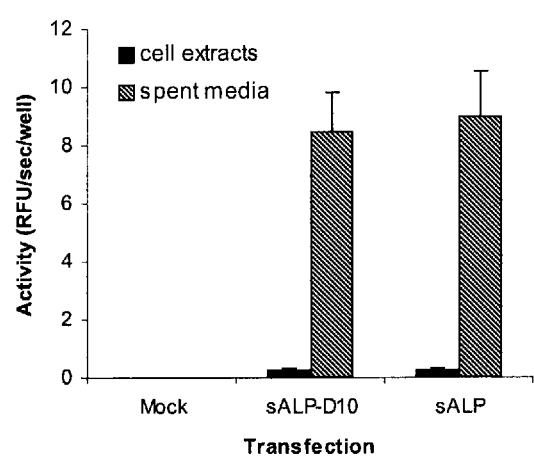
FIG. 13 graphically illustrates through fluorimetric measurement of the alkaline phosphatase activity in the soluble cell extract and spent medium of HEK293 transiently transfected with expression vectors encoding sALP-$D_{10}$ and sALP.
Figure 14:
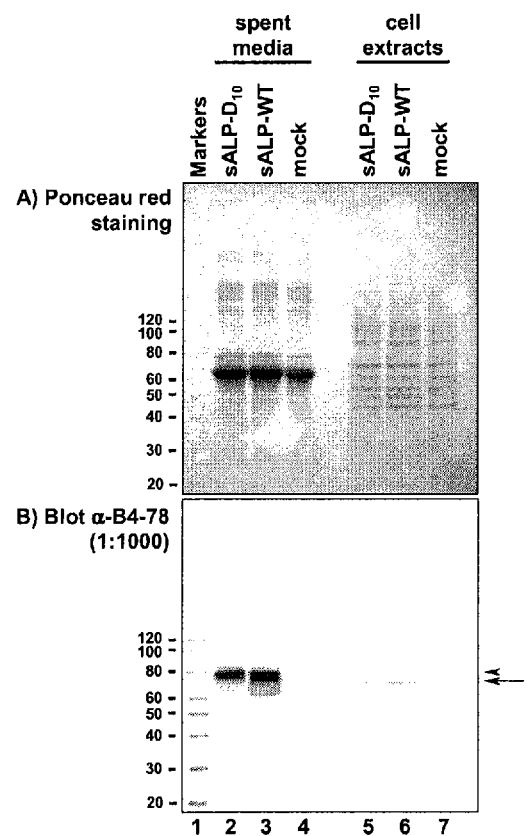
FIG. 14 graphically illustrates the detection of sALP and sALP-$D_{10}$ by Western blotting with the specific B4-78 antibody in the spent media and cell extract of HEK-293 after transient transfection. (Panel A: Ponceau red staining; Panel B: Blot a-B4-78). Shown on the left are the sizes of the molecular weight markers.
Figure 15:
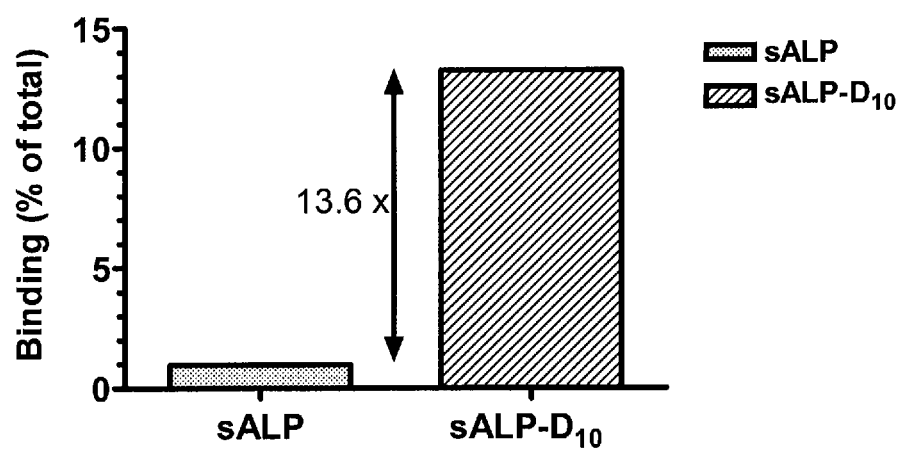
FIG. 15 graphically shows the binding to bone mineral phase of a deca-aspartate fused to secreted alkaline phosphatase.
Figure 18:
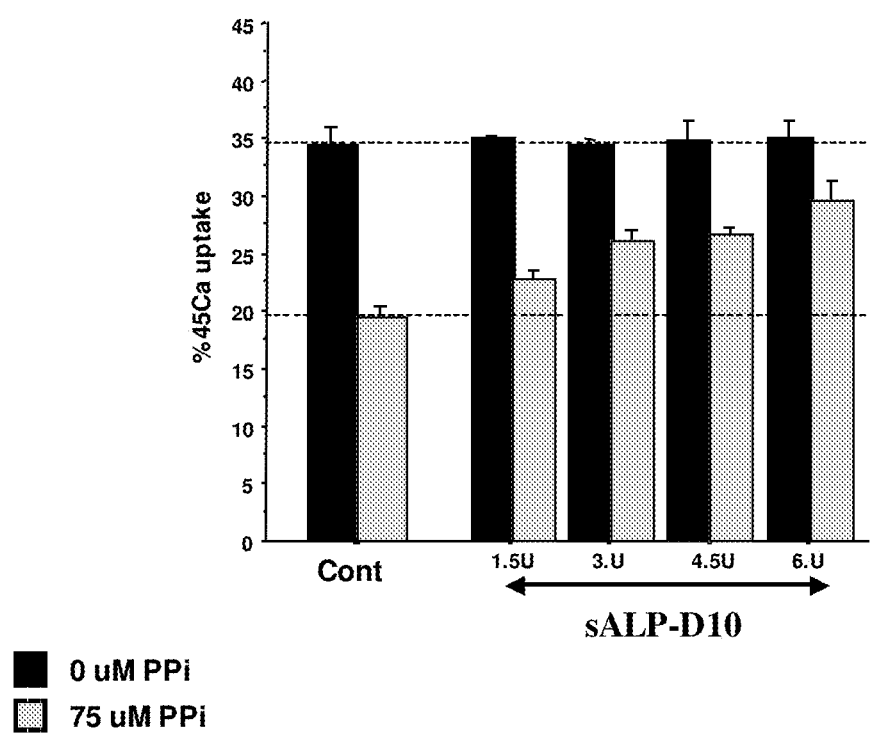
FIG. 18 graphically shows the effect of sALP-D10 on PPi-mediated mineralization inhibition.

The ALP enzymatic activity measured in the conditioned media of HEK293 after transient transfection was very high and of similar magnitude for pcDNA3-RSV-sALP-NEO (sALP) and pcDNA3-RSV-sALP-$D_{10}$-NEO (sALP-$D_{10}$) (FIG. 13). This activity was specific to the plasmid DNA transfected as it was undetectable in mock-transfected cells (mock). The relative activity measured in the media was 35-times greater than that measured in the cell extracts thus attesting to the secretory nature of sALP and sALP-$D_{10}$. Accordingly, for both sALP and sALP-$D_{10}$, immunoblotting using a monoclonal antibody raised against recombinant tissue non-specific human alkaline phosphatase (mAb 4B-78, Developmental Studies Hybridoma Bank) revealed a much stronger signal in the conditioned media than in the cell extracts (FIG. 14B, compare lanes 2, 3 vs. 5, 6). No signal was visualized in the mock-transfected samples (FIG. 14B, lanes 4 and 7). The signal appearing in the mock-transfected cells consists of BSA trace. The apparent molecular weight of the protein detected was estimated to be 70 kDa in the cell extracts (arrow) and slightly higher in the conditioned media (arrowhead). Ponceau red staining of the membrane was performed to monitor the uniform loading of samples (FIG. 14A).

Generation of HEK293 Cells Constitutively Secreting sALP and sALP-$D_{10}$

To induce the stable expression of the sALP and sALP-$D_{10}$ proteins, the pcDNA3-RSV-sALP-NEO and pcDNA3-RSV-sALP-$D_{10}$-NEO vectors was transfected separately in HEK-293S cells using the Lipofectamine-Plus liposome transfection Kit™ (Invitrogen). Transfected cells were selected by adding 800 μg/ml G418 (Life Technologies) to the medium. For each transfection a pool of G-418 resistant cells were analyzed for sALP or sALP-$D_{10}$ expression in the spent culture media using the ALP fluorescent enzymatic assay. The conditioned media collected from the stable cell lines were used for the binding assay study on the bone mineral.

Binding to Reconstituted Mineral Phase of Bone

Aliquots of 20 μl of the acidic bone extract were mixed with 2 μl of 10 M NaOH and the precipitate was pelleted at 10,000×g for 3 minutes at room temperature. The pellet was rinsed twice in 100 μl of buffer (1 mM sodium phosphate pH 7.4+150 mM NaCl). The resultant mineral phase of bone (equivalent to 0.37 mg of dried powder) was then mixed with 100 μl of a solution containing sALP or sALP-$D_{10}$ proteins in the binding buffer (80 mM sodium phosphate pH 7.4+150 mM NaCl). The samples were incubated for 30 minutes at room temperature on the rotating wheel to keep the mineral phase in suspension. The samples were then centrifuged for 3 minutes at room temperature. The pellet containing the bound protein was mixed with 180 μl of the ALP enzymatic assay buffer containing 0.1% BSA and the reaction initiated by adding 20 μl of 100 μM MUP. To allow for more homogeneous assay, conditions the 96 wells plate was shaken for 10 seconds every minute for the duration of the assay.

Enzymatic activity retained on reconstituted mineral bone phase was compared to the equivalent enzymatic activity added in the binding assay. Values of 0.98% and 13.3% of total protein activity bound to the bone mineral phase were calculated for sALP and sALP-$D_{10}$ respectively. A binding difference of more than 13 times in favour of sALP-$D_{10}$ suggests that the C-terminal fused deca-aspartate sequence directly targets sALP to the mineral phase of bone. Furthermore, the fact that it was possible to measure directly ALP activity bound to the mineral phase of bone indicates that the enzyme is bound in a catalytically competent form to hydroxyapatite crystals.

Such fusion protein can be targeted directly to bones where the accumulation of PPi inhibits skeletal mineralization.

Example 7

ALP-$D_{10}$ Decreases Inhibitory Effect of Pyrophosphate on Bone Mineralization UMR106 cells were grown to confluence. They were then cultured for a further 7 days in media containing 10 mM β-glycerophosphate to induce mineralization. Throughout this 7-day culture period, cells were treated with or without 75 μM pyrophosphate (PPi), a mineralization inhibitor and an alkaline phosphatase substrate. To assess the ability of alkaline phosphatase to rescue the PPi-induced mineralization inhibition, cells treated with or without PPi were cultured with varying concentrations of semi-purified sALP-$D_{10}$ produced from HEK293, human embryonic kidney cells. Mineralization was assessed by $^{45}$Ca uptake. Parameters used for this experiment are presented in table 2 below.

TABLE 2

PARAMETERS USED IN ALP-$D_{10}$ ON PPI-INDUCED MINERALIZATION INHIBITION

| ALP | [ALP] (Units/well) | μl ALP/well | β-GP (mM) | PPi (μM) |
|---|---|---|---|---|
| — | 0 | 0 | 10 | 0 |
| — | 0 | 0 | 10 | 75 |
| sALP-$D_{10}$ | 1.5 | 0.5 | 10 | 0 |
| sALP-$D_{10}$ | 1.5 | 0.5 | 10 | 75 |
| sALP-$D_{10}$ | 3 | 1.0 | 10 | 0 |
| sALP-$D_{10}$ | 3 | 1.0 | 10 | 75 |
| sALP-$D_{10}$ | 4.5 | 1.5 | 10 | 0 |
| sALP-$D_{10}$ | 4.5 | 1.5 | 10 | 75 |
| sALP-$D_{10}$ | 6 | 2 | 10 | 0 |
| sALP-$D_{10}$ | 6 | 2 | 10 | 75 |

7-days of treatment with PPi resulted in a 43% decrease in mineralization. Co-treatment of cultures with sALP-$D_{10}$ resulted in a dose-responsive rescue of this mineralization inhibition. Treatment with 1.5 units of sALP-$D_{10}$ resulted in a 30% decrease, 3 and 4.5 units a 24% decrease and 6 units resulted in a 15% decrease in mineralization, corresponding to a 65% rescue of PPi-induced mineralization inhibition.

These results show that the treatment of mineralizing osteoblast with sALP-$D_{10}$ dose-responsively rescues mineralization inhibition induced by PPi.

The above Examples shows that a poly-aspartate fusion to recombinant proteins increases their binding to the mineral phase of bone or to bone tissue and increases the ability of the protein to perform its biological activity as compared to when it is administered alone.

Although the present invention has been described hereinabove by way of preferred embodiments thereof, it can be modified, without departing from the spirit and nature of the subject invention as defined in the appended claims.

REFERENCES

1—Weinberg, J M (2003) An overview of infliximab, etanercept, efalizumab, and alefacept as biologic therapy for psoriasis. Clin Ther 25: 2487-2505.
2—Whyte M P, Valdes R Jr, Ryan L M, McAlister W H (1982) Infantile hypophosphatasia: enzyme replacement therapy by intravenous infusion of alkaline phosphatase-rich plasma from patients with Paget bone disease. J Pediatr 101: 379-386.
3—Whyte M P, Kurtzberg J, McAlister W H, Mumm S, Podgornik M N, Coburn S, Ryan L M, Miller C R, Gottesman G S, Smith A K, Douville J, Waters-Pick B, Armstrong R D, Martin P L (2003) Marrow cell transplantation for infantile hypophosphatasia. J Bone Miner Res 18: 624-636.
4—Fujisaki J, Tokunaga Y, Takahashi T, Shimojo F, Kimura S, Hata T (1997) Osteotropic drug delivery system (ODDS) based on biphosphonic prodrugs. IV: Effects of osteotropic estradiol on bone mineral density and uterine weight in ovariectomized rats. J Drug Targeting 5: 129-138.

5—Uludag H, Gao T, Wohl G R, Kantoci D, Zernicke R F (2000) Bone affinity of a biphosphonate-conjugated protein in vivo. Biotechnol Prog 16: 1115-1118.

6—Sekido T, Sakura N, Higashi Y, Miya K, Nitta Y, Nomura M, Sawanishi H, Morito K, Masamune Y, Kasugai S, Yokogawa K, Miyamoto K-I (2001) Novel drug delivery system to bone using acidic oligopeptides: pharmacokinetic characteristics and pharmacological potential. J Drug Targeting 9: 111-121.

7—Hunter G K, Kyle C L, Goldberg H A (1994) Modulation of crystal formation by bone phosphoproteins: structural specificity of the osteopontin-mediated inhibition of hydroxyapatite formation. Biochem J 300: 723-728.

8—Rowe P S N, de Zoysa P A, Dong R, Wang H R, White K E, Econs M J, Oudet C L (2000) MEPE, a new gene expressed in bone marrow and tumors causing osteomalacia. Genomics 67: 54-68.

9—Gilbert M, Shaw W J, Long J R, Nelson K, Drobny G P, Giachelli C M, Stayton P S (2000) Chimeric peptides of statherin and osteopontin that bind hydroxyapatite and mediate cell adhesion. J Biol Chem 275: 16213-16218.

10-Young M F, Kerr J M, Ibaraki K, Heegaard A M, Robey P G (1992) Structure, expression, and regulation of the major noncollagenous matrix proteins of bones. Clin Orthop 281: 275-294.

11-Salih E, Ashkar S, Gerstenfeld F C, Glimcher M J (1997) Identification of the phosphorylated sites of metabollicaly 32P-labeled osteopontin from cultured chicken osteoblasts. J Biol Chem 272: 13966-13973.

12-Campbell P G, Andress D L (1997) Insulin-like growth factor (IGF)-binding protein-5-(201-218) region regulates hydroxyapatite and IGF-I binding. Am J Physiol 273: E1005-E1013.

13-Patti J M, House-Pompeo K, Boles J O, Garza N, Gurusiddappa S, Hook M (1995) Critical residues in the ligand-binding site of the *Staphylococcus aureus* collagen-binding adhesin (MSCRAMM). J Biol Chem 270: 12005-12011.

14-Symersky J, Patti J M, Carson M, House-Pompeo K, Teale M, Moore D, Jin L, Schneider A, DeLucas L J, Hook M, Narayana S V (1997) Structure of the collagen-binding domain from a *Staphylococcus aureus* adhesin. Nat Struct Biol 4: 833-838.

---

What is claimed is:

1. A bone delivery conjugate comprising a structure selected from the group consisting of:
   A) X-$D_n$-Y-sALP-Z; and
   B) Z-sALP-Y-$D_n$-X,
   wherein X is absent or is an amino acid sequence of at least one amino acid;
   Y is absent or is an amino acid sequence of at least one amino acid;
   Z is absent or is an amino acid sequence of at least one amino acid;
   $D_n$ is a poly aspartate wherein n=10 to 16;
   said sALP is a soluble tissue non-specific alkaline phosphatase; and
   said bone delivery conjugate is catalytically competent to improve skeletal mineralization in bone.

2. The bone delivery conjugate of claim 1, wherein said structure is: Z-sALP-Y-$D_n$-X.

3. The bone delivery conjugate of claim 2, wherein Y is an amino acid sequence of at least one amino acid and X and Z are absent.

4. The bone delivery conjugate of claim 3, wherein n=10.

5. The bone delivery conjugate of claim 2, wherein said sALP is a secreted soluble form of said alkaline phosphatase.

6. The bone delivery conjugate of claim 2, wherein said bone delivery conjugate is encoded by a nucleic acid molecule which hybridizes under high stringency conditions to a nucleic acid molecule having a nucleic acid sequence completely complementary to SEQ ID NO: 7.

7. The bone delivery conjugate of claim 6, wherein said high stringency conditions comprise pre-hybridization and hybridization in 6×SSC, 5×Denhardt's reagent, 0.5% SDS and 100 mg/ml of denatured fragmented salmon sperm DNA at 68° C.; and washes in 2×SSC and 0.5% SDS at room temperature for 10 minutes; in 2×SSC and 0.1% SDS at room temperature for 10 minutes; and in 0.1×SSC and 0.5% SDS at 65° C. three times for five minutes.

8. The bone delivery conjugate of claim 7, wherein Y is an amino acid sequence of at least one amino acid and X and Z are absent, and wherein n=10.

9. A bone delivery composition comprising a pharmaceutically acceptable carrier and a bone delivery conjugate comprising a structure selected from the group consisting of:
   A) X-$D_n$-Y-sALP-Z; and
   B) Z-sALP-Y-$D_n$-X,
   wherein X is absent or is an amino acid sequence of at least one amino acid;
   Y is absent or is an amino acid sequence of at least one amino acid;
   Z is absent or is an amino acid sequence of at least one amino acid;

$D_n$ is a poly aspartate wherein n=10 to 16;
said sALP is a soluble tissue non-specific alkaline phosphatase; and
said bone delivery conjugate is catalytically competent to improve skeletal mineralization in bone.

10. The bone delivery composition of claim 9, wherein said structure is: Z-sALP-Y-$D_n$-X.

11. The bone delivery composition of claim 10, wherein said bone delivery conjugate is encoded by a nucleic acid molecule which hybridizes under high stringency conditions to a nucleic acid molecule having a nucleic acid sequence completely complementary to SEQ ID NO: 7, wherein said high stringency conditions comprise pre-hybridization and hybridization in 6×SSC, 5×Denhardt's reagent, 0.5% SDS and 100 mg/ml of denatured fragmented salmon sperm DNA at 68° C.; and washes in 2×SSC and 0.5% SDS at room temperature for 10 minutes; in 2×SSC and 0.1% SDS at room temperature for 10 minutes; and in 0.1×SSC and 0.5% SDS at 65° C. three times for five minutes.

12. The bone delivery composition of claim 11, wherein Y is an amino acid sequence of at least one amino acid and X and Z are absent, and wherein n=10.

13. A method of delivering a protein to bone tissue of a mammal comprising administering to said mammal an effective amount of a bone delivery conjugate comprising a structure selected from the group consisting of:
A) X-$D_n$-Y-sALP-Z; and
B) Z-sALP-Y-$D_n$-X,
wherein X is absent or is an amino acid sequence of at least one amino acid;
Y is absent or is an amino acid sequence of at least one amino acid;
Z is absent or is an amino acid sequence of at least one amino acid;
$D_n$ is a poly aspartate wherein n=10 to 16;
said sALP is a soluble tissue non-specific alkaline phosphatase; and
said bone delivery conjugate is catalytically competent to improve skeletal mineralization in bone.

14. The method of claim 13,
wherein said structure is: Z-sALP-Y-$D_n$-X;
said bone delivery conjugate is encoded by a nucleic acid molecule which hybridizes under high stringency conditions to a nucleic acid molecule having a nucleic acid sequence completely complementary to SEQ ID NO: 7;
said high stringency conditions comprise pre-hybridization and hybridization in 6×SSC, 5×Denhardt's reagent, 0.5% SDS and 100 mg/ml of denatured fragmented salmon sperm DNA at 68° C.; and washes in 2×SSC and 0.5% SDS at room temperature for 10 minutes; in 2×SSC and 0.1% SDS at room temperature for 10 minutes; and in 0.1×SSC and 0.5% SDS at 65° C. three times for five minutes;
Y is an amino acid sequence of at least one amino acid and X and Z are absent; and n=10.

15. The method of claim 13, wherein said mammal is human.

16. The method of claim 15, wherein said effective amount is 1 to 10 milligrams per kilogram of body weight.

17. The method of claim 16, wherein said effective amount is administered to said human more than once at an interval ranging from daily to weekly.

18. The method of claim 15, wherein said effective amount is about 1 milligram per kilogram of body weight.

19. A method of treating a condition or disease related to a bone defect characterized by a lack of or an insufficient amount of functional alkaline phosphatase comprising administering to a mammal in need thereof an effective amount of a bone delivery conjugate comprising a structure selected from the group consisting of:
A) X-D-Y-sALP-Z; and
B) Z-sALP-Y-D-X,
wherein X is absent or is an amino acid sequence of at least one amino acid;
Y is absent or is an amino acid sequence of at least one amino acid;
Z is absent or is an amino acid sequence of at least one amino acid;
$D_n$ is a poly aspartate wherein n=10 to 16;
said sALP is a soluble tissue non-specific alkaline phosphatase; and
said bone delivery conjugate is catalytically competent to improve skeletal mineralization in bone,
wherein the conjugate is in a pharmaceutically acceptable carrier.

20. The method of claim 19, wherein said condition or disease is hypophosphatasia.

21. The method of claim 19, wherein said mammal is human.

22. The method of claim 21, wherein said effective amount is 1 to 10 milligrams per kilogram of body weight.

23. The method of claim 22, wherein said effective amount is administered to said human more than once at an interval ranging from daily to weekly.

24. The method of claim 21, wherein said effective amount is about 1 milligram per kilogram of body weight.

25. The bone delivery conjugate of claim 1, wherein said sALP is capable of catalyzing the cleavage of inorganic pyrophosphate (PPi).

26. The bone delivery composition of claim 10, wherein Y is an amino acid sequence of at least one amino acid and X and Z are absent.

27. The bone delivery composition of claim 26, wherein n=10.

28. The bone delivery composition of claim 10, wherein said sALP is a secreted soluble form of said alkaline phosphatase.

29. The bone delivery composition of claim 9, wherein said sALP is capable of catalyzing the cleavage of inorganic pyrophosphate (PPi).

30. The method of claim 19, wherein said structure is: Z-sALP-Y-$D_n$-X.

31. The method of claim 30, wherein Y is an amino acid sequence of at least one amino acid and X and Z are absent.

32. The method of claim 31, wherein n=10.

33. The method of claim 30, wherein said sALP is a secreted soluble form of said alkaline phosphatase.

34. The method of claim 30, wherein said bone delivery conjugate is encoded by a nucleic acid molecule which hybridizes under high stringency conditions to a nucleic acid molecule having a nucleic acid sequence completely complementary to SEQ ID NO: 7, wherein said high stringency conditions comprise pre-hybridization and hybridization in 6×SSC, 5×Denhardt's reagent, 0.5% SDS and 100 mg/ml of denatured fragmented salmon sperm DNA at 68° C.; and washes in 2×SSC and 0.5% SDS at room temperature for 10 minutes; in 2×SSC and 0.1% SDS at room temperature for 10 minutes; and in 0.1×SSC and 0.5% SDS at 65° C. three times for five minutes.

35. The method of claim 34, wherein Y is an amino acid sequence of at least one amino acid and X and Z are absent, and wherein n=10.

36. The method of claim 19, wherein said sALP is capable of catalyzing the cleavage of inorganic pyrophosphate (PPi).

37. The conjugate of claim 1, wherein said composition is formulated for intravenous injection.

38. The composition of claim 9, wherein said composition is formulated for parenteral administration.

39. The composition of claim 9, wherein said composition is formulated for intravenous injection.

40. The method of claim 13, wherein said conjugate is formulated for intravenous injection.

41. The method of claim 19, wherein said conjugate is formulated for parenteral administration.

42. The method of claim 19, wherein said conjugate is formulated for intravenous injection.

43. The conjugate of claim 1, wherein said sALP is a human tissue non-specific alkaline phosphatase.

44. The conjugate of claim 1, wherein Y lacks a transamination site.

45. The composition of claim 9, wherein said sALP is a human tissue non-specific alkaline phosphatase.

46. The composition of claim 9, wherein Y lacks a transamination site.

47. The composition of claim 9, wherein said composition is formulated to provide 0.001 milligrams (mg) to 500 mg per kilogram (kg) of body weight per day of said conjugate.

48. The method of claim 13, wherein said sALP is a human tissue non-specific alkaline phosphatase.

49. The method of claim 19, wherein said sALP is a human tissue non-specific alkaline phosphatase.

\* \* \* \* \*

UNITED STATES PATENT AND TRADEMARK OFFICE
CERTIFICATE OF CORRECTION

PATENT NO. : 10,000,532 B2
APPLICATION NO. : 12/638527
DATED : June 19, 2018
INVENTOR(S) : Philippe Crine et al.

Page 1 of 1

It is certified that error appears in the above-identified patent and that said Letters Patent is hereby corrected as shown below:

In the Claims

Column 62, Line 5, in Claim 19, replace "B) Z-sALP-Y-D-X" with --B) Z-sALP-Y-$D_n$-X--.

Signed and Sealed this
Twenty-eighth Day of May, 2019

Andrei Iancu
*Director of the United States Patent and Trademark Office*